(12) United States Patent
Chobanian et al.

(10) Patent No.: US 10,000,484 B2
(45) Date of Patent: Jun. 19, 2018

(54) INHIBITORS OF THE RENAL OUTER MEDULLARY POTASSIM CHANNEL

(71) Applicants: MERCK SHARP & DOHME CORP., Rahway, NJ (US); Harry Chobanian, Kenilworth, NJ (US); Barbara Pio, Kenilworth, NJ (US); Yan Guo, Kenilworth, NJ (US); Fa-Xiang Ding, Kenilworth, NJ (US); Shuzhi Dong, Kenilworth, NJ (US); Shawn P. Walsh, Kenilworth, NJ (US); Jinlong Jiang, Kenilworth, NJ (US); Dooseop Kim, Seoul (KR)

(72) Inventors: Harry Chobanian, Kenilworth, NJ (US); Barbara Pio, Kenilworth, NJ (US); Yan Guo, Kenilworth, NJ (US); Fa-Xiang Ding, Kenilworth, NJ (US); Shuzhi Dong, Kenilworth, NJ (US); Shawn P. Walsh, Kenilworth, NJ (US); Jinlong Jiang, Kenilworth, NJ (US); Dooseop Kim, Seoul (KR)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days. days.

(21) Appl. No.: 15/101,467

(22) PCT Filed: Dec. 16, 2014

(86) PCT No.: PCT/US2014/070441
§ 371 (c)(1),
(2) Date: Jun. 3, 2016

(87) PCT Pub. No.: WO2015/095097
PCT Pub. Date: Jun. 25, 2015

(65) Prior Publication Data
US 2016/0304515 A1   Oct. 20, 2016

Related U.S. Application Data

(60) Provisional application No. 61/917,564, filed on Dec. 18, 2013.

(51) Int. Cl.
| | |
|---|---|
| A61K 31/4355 | (2006.01) |
| A61K 31/437 | (2006.01) |
| A61K 31/4985 | (2006.01) |
| A61K 31/519 | (2006.01) |
| A61K 31/55 | (2006.01) |
| C07D 471/04 | (2006.01) |
| C07D 487/04 | (2006.01) |
| C07D 498/04 | (2006.01) |
| A61K 31/401 | (2006.01) |
| A61K 31/4178 | (2006.01) |

(Continued)

(52) U.S. Cl.
CPC ......... *C07D 471/04* (2013.01); *A61K 31/401* (2013.01); *A61K 31/4178* (2013.01); *A61K 31/424* (2013.01); *A61K 31/437* (2013.01); *A61K 31/4422* (2013.01); *A61K 31/496* (2013.01); *A61K 31/4965* (2013.01); *A61K 31/4985* (2013.01); *A61K 31/519* (2013.01); *A61K 31/55* (2013.01); *A61K 31/585* (2013.01); *A61K 45/06* (2013.01); *C07D 487/04* (2013.01); *C07D 498/04* (2013.01)

(58) Field of Classification Search
CPC .............. A61K 31/4355; A61K 31/437; A61K 31/4985; A61K 31/519; A61K 31/55; C07D 471/04; C07D 487/04; C07D 498/04
USPC ............ 514/215, 249, 264.1, 302, 303, 307; 540/580; 544/279, 349, 350; 546/116, 546/119, 148
See application file for complete search history.

(56) References Cited

U.S. PATENT DOCUMENTS

2010/0324054 A1   12/2010   Biftu et al.

FOREIGN PATENT DOCUMENTS

| WO | 2012058134 A1 | 5/2012 |
| WO | 2013066714 A1 | 5/2013 |

(Continued)

OTHER PUBLICATIONS

Bhave,G., Development of a selective small-molecule inhibitor Kir1.1, the renal outer medullary potassium channel, Mol. Pharmacol., 2011, 42-50, 79.

(Continued)

*Primary Examiner* — Brenda L Coleman
(74) *Attorney, Agent, or Firm* — Sarah Hooson; Catherine D. Fitch

(57) ABSTRACT

The present invention provides compounds of Formula (I) (Formula (I)) including pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention.

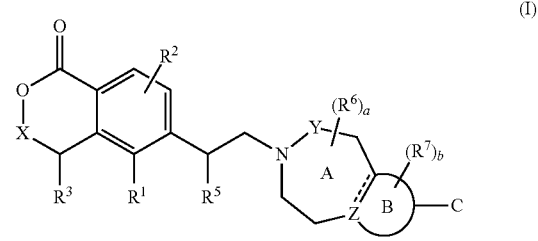

(I)

(Continued)

9 Claims, No Drawings

(51) Int. Cl.
A61K 31/424 (2006.01)
A61K 31/4422 (2006.01)
A61K 31/496 (2006.01)
A61K 31/4965 (2006.01)
A61K 31/585 (2006.01)
A61K 45/06 (2006.01)

(56) References Cited

FOREIGN PATENT DOCUMENTS

WO 2013066718 A2 5/2013
WO 2014126944 A2 8/2014

OTHER PUBLICATIONS

Fringuelli, F. et al., A Simple Procedure for the Synthesis of Labile Aryl Oxiranes by Epoxidation, Organic Preparations and Procedures Int., 1989, p. 757-761, vol. 21, No. 6.
Hebert, S. C. et al., Molecular Diversity and Regulation of Renal Potassium Channels, Physiol Rev., 2005, p. 319-371, vol. 85.
Ho, K. et al., Cloning and expression of an inwardly rectifying ATP-regulated potassium channel, Nature, 1993, p. 31-38, vol. 362.
International Preliminary Report on Patentability for PCT/US2014/070441 dated Jun. 21, 2016, 8 pages.
International Search Report PCT/US14/70441 dated Mar. 16, 2015; 11 pages.
Ji, W. et al., Rare independent mutations in renal salt handling genes contribute to blood pressure variation, Nature Genetics, 2008, p. 592-599, vol. 40, No. 5.
Lewis, L. M., High-throughput screening reveals a small-molecule inhibitor of the Renal Outer Medullary Potassium Channel and Kir7.1, Mol. Pharncol., 2009, 1094-1103, 76.
Lifton, R. P. et al., Molecular Mechanisms of Human Hypertension, Cell, 2001, p. 545-556, vol. 104.
Lorenz, J. N. et al., Impaired Renal NaCl Absorption inMic Lacking the ROMK Potassium Cannel, a Model for Type II Bartter's Syndrome, The Journal of Biological Chemistry, 2002, p. 37871-37880, vol. 277, No. 40.
Lu, M. et al., Absence of Small Conductance K+ Channel (SK) Activity in Apical Membranes of Thick Ascending Limb and Cortical Collectiong Duct in ROMK (Bartter's) Knockout Mice, The Journal of Biological Chemistry, 2002, p. 37881-37887, vol. 277, No. 40.
Molander, G. A. et al., Stereoselective Suzuki-Miyaura Cross-Coupling Reactions of Potassium Alkenyltrifluoroborates with Alkenyl Bromides, J. Org. Chem, 2005, p. 3950-3956, vol. 70.
Molander, G. A. et al., Suzuki-Miyaura Cross-Coupling Reactions of Potassium Vinyltrifluoroborate with Aryl and Heteroaryl Electrophiles, J. Org. Chem, 2006, p. 9861-9686, vol. 71.
Nguyen, TT et al., Characterization of a Druggable Binding site in the Renal Outer Medullary Potassium Channel, The FASEB Journal, Apr. 2012, 867.7, 26.
Nomura, Y. et al., Synthesis and Structure-Activity Relationships of 2-(4-Benzhydryl-1-piperazinyl)-1-phenylethanols as New Calcium Blockers, Chem. Phar. Bull, 1995, p. 241-246, vol. 43, No. 2.
Reinalter, S. C. et al., Pharmacotyping of hypokalaemic salt-losing tubular disorders, Acta Physiol Scand, 2004, p. 513-521, vol. 181.
Shuck, M. E. et al., Cloning and Characterization of Multiple Forms of the Human Kidney ROM-K Potassium Channel, The Journal of Biological Chemistry, 1994, p. 24261-24270, vol. 269, No. 39.
Tobin, M. D. et al., Common Variants in Genes Underlying Monogenic Hypertension and Hypotension and Blood Pressure in the General Population, Hypertension, 2008, p. 1658-1664, vol. 51. No. 6.
Wang, W. et al., Renal potassium channesl: recent developments, Current Opinion in Nephrology and Hypertension, 2004, p. 549-555, vol. 13, No. 5.

INHIBITORS OF THE RENAL OUTER MEDULLARY POTASSIM CHANNEL

CROSS-REFERENCE TO RELATED APPLICATIONS

This application is a U.S. National Phase application under 35 U.S.C. § 371 of PCT Application PCT/US14/070441, filed Dec. 16, 2014, which claims priority from and the benefit of US Provisional Application U.S. Ser. No. 61/917,564 filed Dec. 18, 2013.

BACKGROUND OF THE INVENTION

The Renal Outer Medullary Potassium (ROMK) channel (Kir1.1) (see e.g., H o, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

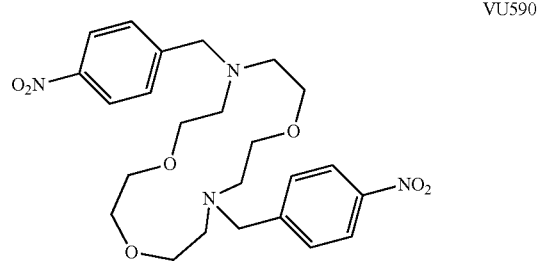

VU590

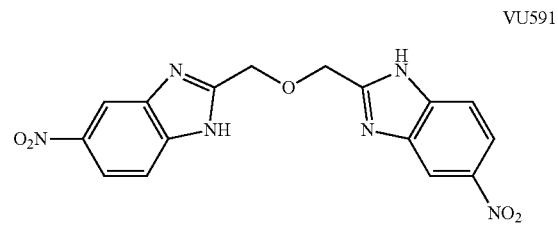

VU591

Patent application publication number WO2010/129379, published Nov. 11, 2010 having common representative Merck Sharp & Dohme Corp., (also published as US2010/0286123 on same date), describes ROMK inhibitors having the generic formula:

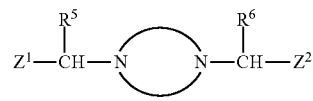

and, e.g., an embodiment

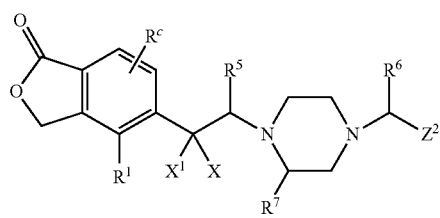

wherein $R^5$ and $R^6$ are independently —H, —$C_{1-6}$ alkyl, —$C_{3-6}$ cycloalkyl, —$CF_3$, —$CHF_2$, —$CH_2F$ or —$CH_2OH$; X is —H, —OH, —$OC_{1-3}$alkyl, —F, oxo, $NH_2$ or —$CH_3$; and $X^1$ is —H or —$CH_3$.

Patent application publication number WO2012/058134, published May 3, 2012, having common representative Merck Sharp & Dohme Corp., describes ROMK inhibitors having the generic formula:

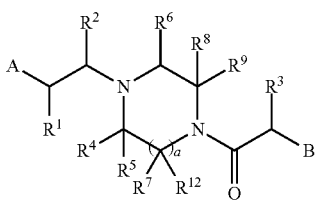

wherein A and B are mono and/or bicyclic aromatic groups; $R^2$ is —H, —$C_{1-6}$ alkyl, —$C_{3-6}$ cycloalkyl, $CF_3$, —$CH_2OH$, or —$CO_2R$, or $R^2$ can be joined to $R^1$ or $R^{10a}$ to form a ring; $R^3$ is —H, —$C_{1-6}$ alkyl, —$C_{3-6}$ cycloalkyl, —OH, —F, —$OC_{1-3}$ alkyl, or —$CH_2OH$, or $R^3$ can be joined to $R^{10b}$ to form a ring.

Patent application publication number WO2012/058116, published May 3, 2012, having common representative Merck Sharp & Dohme Corp., describes ROMK inhibitors having the generic formula:

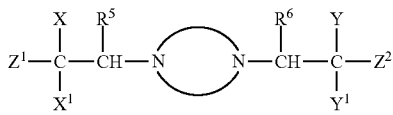

and, e.g., an embodiment

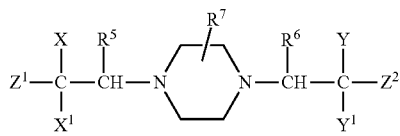

wherein $R^5$ and $R^6$ are independently —H, —$C_{1-6}$ alkyl or —C(O)$OC_{1-3}$alkyl; and X, $X^1$, Y and $Y^1$ are independently —H or —$C_{1-6}$alkyl; or $Y^1$ can be joined together with $Z^2$ to form a fused ring system.

However, continuing discovery of selective small molecule inhibitors of ROMK is still needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

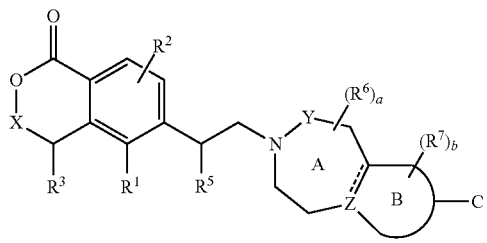

and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention is directed to compounds having structural Formula I:

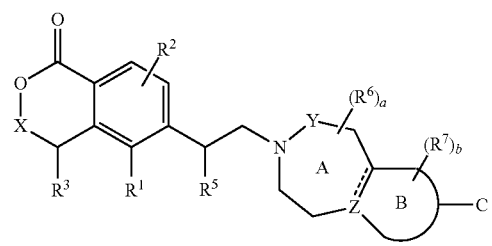

or a pharmaceutically acceptable salt thereof. In the compounds of Formula 1,

X is $CHR^4$ or a bond;

$R^1$ and $R^2$ are each independently of one another H, —OH, halogen, —$C_{1-4}$alkyl optionally substituted with 1-9 halogens, —$C_{3-4}$cycloalkyl, or —$OC_{1-4}$alkyl optionally substituted with 1-9 halogens;

$R^3$ is H or —$C_{1-4}$alkyl;

$R^4$ is H, —$C_{1-4}$alkyl, or —$OC_{1-4}$alkyl;

$R^5$ is —H, —OH, oxo, fluoro or —$C_{1-4}$alkyl which is optionally substituted with 1-9 halogens;

Y is —$CH_2$— or a bond;

The dashed line between rings A and B represents an optional double bond where rings A and B are fused;

A is a 6 or 7-membered heterocyclic ring having 1 or 2-N-atoms and optionally 1 double bond;

Z is a nitrogen atom or a carbon atom, where the carbon atom is unsubstituted when the A and B rings are fused by a double bond, or the carbon atom is substituted with —H when the A and B rings are fused by a single bond;

$R^6$ represents optional substituent groups on ring A which are each independently selected from the group consisting of —$C_{1-3}$alkyl optionally substituted with 1-7 halogens, and —$OC_{1-3}$alkyl optionally substituted with 1-7 halogens;

$R^7$ represents optional substituent groups on ring B which are each independently selected from the group consisting of -halogen, —$C_{1-3}$alkyl optionally substituted with 1-7 halogens, and —$OC_{1-3}$alkyl optionally substituted with 1-7 halogens;

a and b are each independently 0 or an integer from 1-3;

B is a 5- or 6-membered heterocyclic, heteroaromatic or phenyl ring fused to ring A, wherein ring B optionally comprises 1-3 heteroatoms selected from O and N, including Z if Z is N, and wherein ring B optionally comprises one oxo group, and optionally comprises 1-3 double bonds including the optional double bond between rings A and B;

C is a cyclic or bicyclic group selected from
  (a) Phenyl substituted with one group —CN or -tetrazole and optionally with 1-3 groups independently selected from halogen, —$C_{1-3}$alkyl optionally substituted with 1-7 halogens, and —$OC_{1-3}$alkyl optionally substituted with 1-7 halogens;
  (b) Pyridyl, pyrimidyl, pyrazinyl, pyridazolyl or thiazolyl substituted with one group —CN or -tetrazole, and optionally substituted with 1-3 groups independently selected from halogen, —$C_{1-3}$alkyl optionally substituted with 1-7 halogens, and —$OC_{1-3}$alkyl optionally substituted with 1-7 halogens;
  (c)

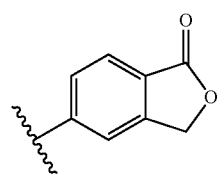 [SMILES: *c1ccc2c(c1)COC2=O]

which is optionally substituted with 1-3 groups independently selected from halogen, —$C_{1-3}$alkyl optionally substituted with 1-7 halogens, and —$OC_{1-3}$alkyl optionally substituted with 1-7 halogens;
  (d)

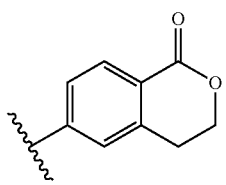 [SMILES: *c1ccc2c(c1)CCOC2=O]

which is optionally substituted with 1-3 groups independently selected from halogen, —$C_{1-3}$alkyl optionally substituted with 1-7 halogens, and —$OC_{1-3}$alkyl optionally substituted with 1-7 halogens; and
  (e)

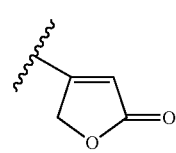 [SMILES: *C1=CC(=O)OC1]

optionally substituted with 1-2 groups selected from —$CH_3$, —$OCH_3$, and halogen.

In many embodiments, the compound is also defined by Formula II with the substituent definitions presented above, as well as the definitions presented hereafter. The definitions also apply to pharmaceutically acceptable salts of the compound of Formula I or II.

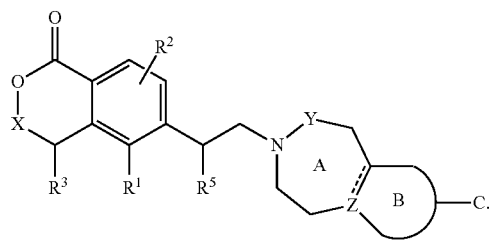

II

In many embodiments, $R^1$ and $R^2$ are each independently H, F, —$C_{1-2}$alkyl optionally substituted with 1-5 F, or —$OC_{1-2}$alkyl optionally substituted with 1-5 F.

In many embodiments, $R^3$ is H or —$C_{1-2}$alkyl.

In many embodiments, $R^4$ is H or —$CH_3$.

In many embodiments, $R^5$ is —H, —OH, F or —$CH_3$.

In many embodiments, C is a cyclic or bicyclic group selected from
  (a) Phenyl substituted with one group —CN or -tetrazole, and optionally with 1-2 groups independently selected from —$CH_3$, —$OCH_3$, and halogen;
  (b) Pyridyl substituted with one group —CN or -tetrazole and optionally with 1-2 groups independently selected from —$CH_3$, —$OCH_3$, and halogen;
  (c)

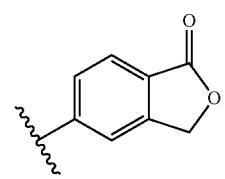 [SMILES: *c1ccc2c(c1)COC2=O]

optionally substituted on the phenyl ring with 1-2 groups selected from —$CH_3$, —$OCH_3$, and halogen;
  (d)

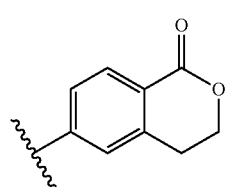 [SMILES: *c1ccc2c(c1)CCOC2=O]

optionally substituted on the lactone ring with 1-2 groups selected from —$CH_3$, —$OCH_3$, and halogen; and (e)

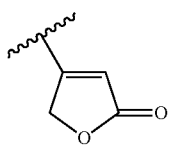 [SMILES: *C1=CC(=O)OC1]

optionally substituted with 1-2 groups selected from —CH₃, —OCH₃, and halogen.

In many embodiments, $R^1$ and $R^3$ are each H or —CH₃.
In many embodiments, $R^2$ is H.
In many embodiments, $R^4$ is H or —CH₃.
In many embodiments, $R^5$ is —H or —OH.
In many embodiments, C is a cyclic or bicyclic group selected from
(a) Phenyl substituted with one group —CN or -tetrazole, and optionally with 1-2 groups independently selected from —CH₃, —OCH₃, and halogen;
(b) Pyridyl substituted with one group —CN, and optionally with 1-2 groups independently selected from —CH₃, —OCH₃, and halogen;
(c)

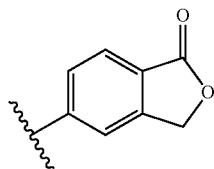 [SMILES: *c1ccc2c(c1)COC2=O]

optionally substituted on the phenyl ring with one group selected from —CH₃, —OCH₃, and halogen;
(d)

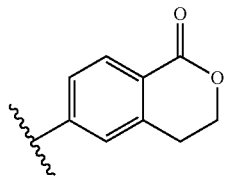 [SMILES: *c1ccc2c(c1)CCOC2=O]

optionally substituted on the lactone ring with one group —CH₃; and
(e)

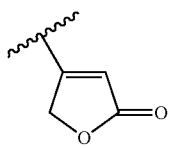 [SMILES: *C1=CC(=O)OC1]

optionally substituted with one group —CH₃.

In many embodiments, Ring B is selected from phenyl, pyrimidine, pyrazole, imidazole, imidazoline, 1,2,4-triazole, 1,2,4-triazolone, 1,3-oxazole, oxazolidinone, pyrrolidine, pyridine, pyrazine, pyridazine, piperidine, piperazine, isoxazole, and pyrrolidinone optionally having a double bond.

In many embodiments, Ring B is selected from phenyl, pyrimidine, pyrazole, imidazole, 1,2,4-triazole, 1,2,4-triazolone, 1,3-oxazole, oxazolidinone, pyrrolidine, and pyrrolidinone optionally having a double bond.

The substituent groups as defined above can be combined independently of one another to create additional embodiments.

All structural Formulas, embodiments and classes thereof described herein include the pharmaceutically acceptable salts of the compounds defined therein.

As used herein except as noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me). "Cycloalkyl" is a cyclized alkyl ring having the indicated number of carbon atoms. Examples of cycloalkyl include cyclopropyl, cyclobutyl, cyclopentyl and cyclohexyl.

"Halo" means —F, —Cl, —Br, or —I. Fluoro or chloro are preferred.

Unless expressly depicted or described otherwise, variables depicted in a structural formula with a "floating" bond, such as $R^2$ and $R^7$, are permitted on any carbon atom or heteroatom that can be substituted in the ring to which the variable is attached. When a moiety is noted as being "optionally substituted" in Formula I or any embodiment thereof, it means that Formula I or the embodiment thereof encompasses compounds that contain the noted substituent (or substituents) on the moiety and compounds that do not contain the noted substituent (or substituents) on the moiety. Reference to the compounds of Formula I herein encompasses those compounds and all embodiments and classes thereof. Reference to the compounds of this invention as those of a specific formula or embodiment or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of claim 1 in a therapeutically effective amount to a patient in need of diueresis, natriuresis or both. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, postoperative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 µM or less, preferably 1 µM or less, and more preferably 0.25 µM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g., olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, eplerenone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104, 869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063, 208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885, 292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S), 5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

EXAMPLES

Several methods for preparing the compounds of this invention are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products.

General Schemes

Compound IA, which is substituted at the benzylic position with an —OH group, can be prepared following the sequence detailed in Scheme 1. Coupling of epoxide 1 to fused piperidine 2 at elevated temperatures leads to the formation of alcohols IA (Nomura, Y. et al. Chemical & Pharmaceutical Bulletin, 1995, 43(2), 241-6). The reaction can be carried out with conventional heating, or by heating using a microwave apparatus. A number of solvents can be used in this reaction, for example, ethanol and 2-propanol. Spirocyclic amines may be free bases, or they may be salts, in which case a base such as triethylamine or N,N'-diisopropylethylamine may be added. Note that when enantiopure chiral epoxides are employed (such as (R)-1 in Scheme 1), epoxide opening occurs with retention of stereochemistry in the benzylic position and individual isomer (R)-IA may be obtained (and if the (S)-epoxide is employed the alcohol produced will have the opposite stereochemistry to that shown). Alternatively, chiral HPLC separation of enantiomers or diastereomers of IA may be performed to provide single enantiomers or diastereomers.

SCHEME 1

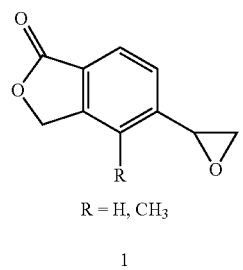

R = H, CH₃

1

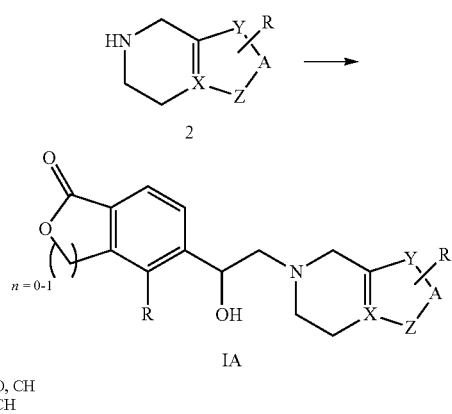

IA

Y = N, O, CH
X = N, CH
A = N, CH
Z = N, CH

Compounds of formula IB can be prepared by the sequence detailed in Scheme 2. Aldehydes 3 may be used in reductive alkylation reactions of fused piperidine amines 2 to afford ROMK inhibitors of the formula IB by using various reductive amination conditions (for example using sodium cyanoborohydride, sodium triacetoxy borohydride, or titanium tetra-isopropoxide, followed by sodium borohydride or sodium cyanoborohydride).

SCHEME 2

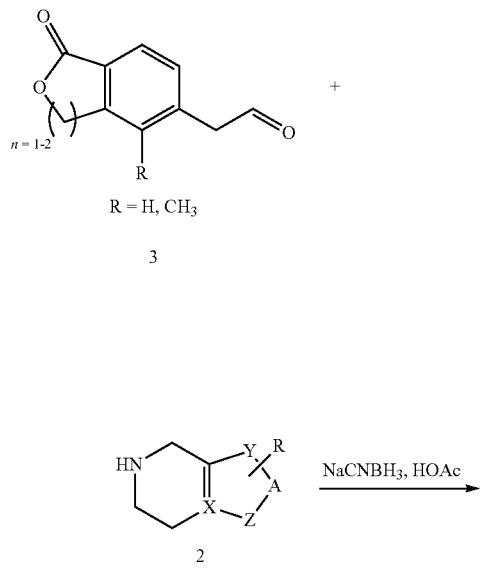

-continued

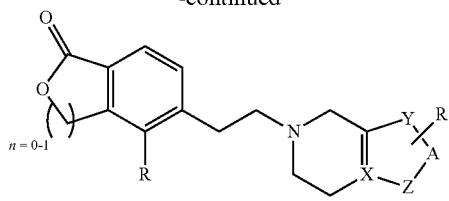

IB

Y = N, O, CH
X = N, CH
A = N, CH
Z = N, CH

The epoxides 1 (and single enatiomers (R)-1 and (S)-1) can be prepared following the method detailed in Scheme 3. Treatment of 4 (where X is chloride, bromide, iodide, or trifluoromethane sulfonate) with commercially available potassium vinyl trifluoroborate (Molander, G.; Luciana, A. Journal of Organic Chemistry, 2005, 70(10), 3950-3956) under palladium catalyzed coupling conditions with an appropriate phosphine ligand gives rise to styrene 5 (Molander, G.; Brown, A. Journal of Organic Chemistry, 2006, 71(26), 9681-9686). Alternatively, other methods may be employed, for example, using vinylstannane reagents and palladium catalysis. The resulting styrenes 5 can be converted to the corresponding epoxides 1 under various epoxidation conditions, for example, with m-CPBA (Fringuelli, F. et al. Organic Preparations and Procedures International, 1989, 21(6), 757-761). The racemic epoxide 1 can be resolved under chiral HPLC chromatography conditions to afford its enantiomers, which can be used in place of 1 according to Scheme 1.

SCHEME 3

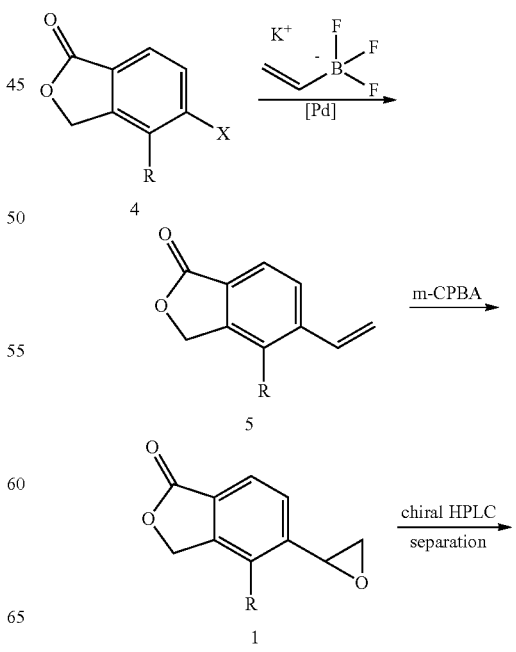

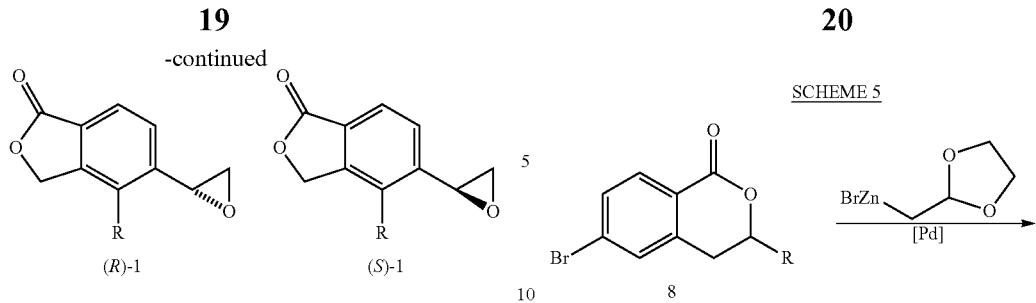

Aldehydes 3A may be prepared in numerous ways, with two approaches described in Scheme 4. Treatment of 4 (where X is bromide, iodide, or trifluoromethane sulfonate) with bromo(1,3-dioxolan-2-ylmethyl)zinc in the presence of an appropriate palladium catalyst and ligand, such as palladium(II) acetate and tri-t-butylphosphine-BF4 complex, provides the corresponding aryl 1,3-dioxolan-2-ylmethyl derivative 6. Then the aldehydes 3A may be obtained by treatment with HCl in the presence of water and an organic solvent. Alternatively, reaction of 4 (where X is bromide, iodide, or trifluoromethane sulfonate) with allyltributylstannane in the presence of palladium catalyst affords the allyl product 7. Oxidation, for example with ozone, followed by dimethyl sulfide, provides aldehydes 3A.

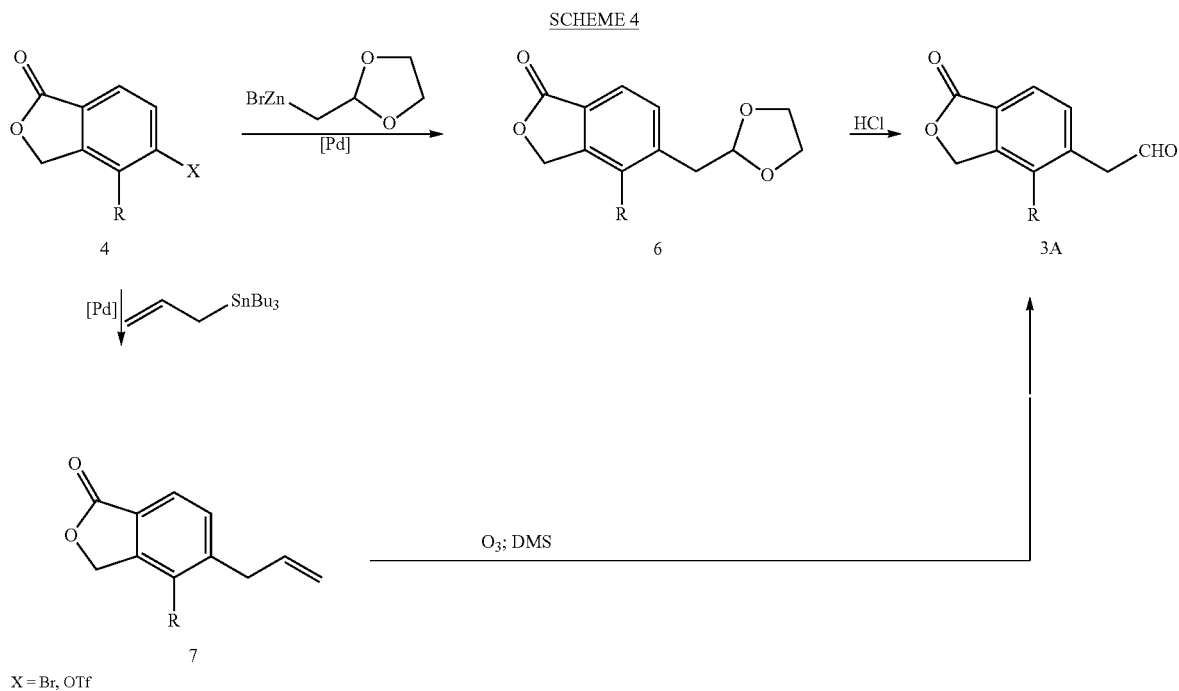

Aldehydes 10 may be prepared in numerous ways, with one approach described in Scheme 5. Treatment of 8 (where X is bromide, iodide, or trifluoromethane sulfonate) with bromo(1,3-dioxolan-2-ylmethyl)zinc in the presence of an appropriate palladium catalyst and ligand, such as palladium (II) acetate and tri-t-butylphosphine-BF$_4$ complex, provides the corresponding aryl 1,3-dioxolan-2-ylmethyl derivative 9. Then the aldehydes 10 may be obtained by treatment with HCl in the presence of water and an organic solvent.

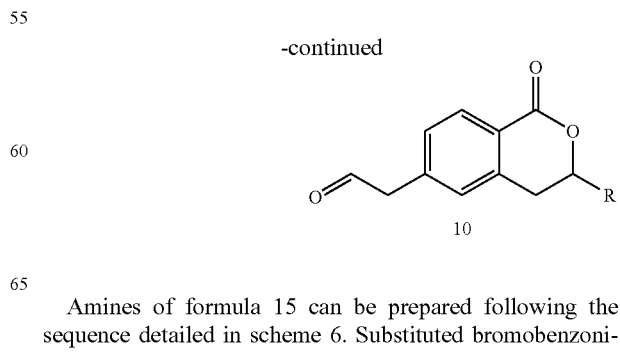

Amines of formula 15 can be prepared following the sequence detailed in scheme 6. Substituted bromobenzonitrile 11 can be converted to corresponding benzimidamide 12 by treating with ammonium chloride and AlCl$_3$ which is then converted to fused pyrimidine-piperidine core 13 by treating with (E)-tert-butyl 3-((dimethylamino)methylene)-4-oxopiperidine-1-carboxylate. Conversion of bromo compound 13 to cyano 14 can be achieved by treatment with zinc cyanide and Pd$_2$(dba)$_3$. Free amine 15 may be obtained by treatment with TFA.

SCHEME 6

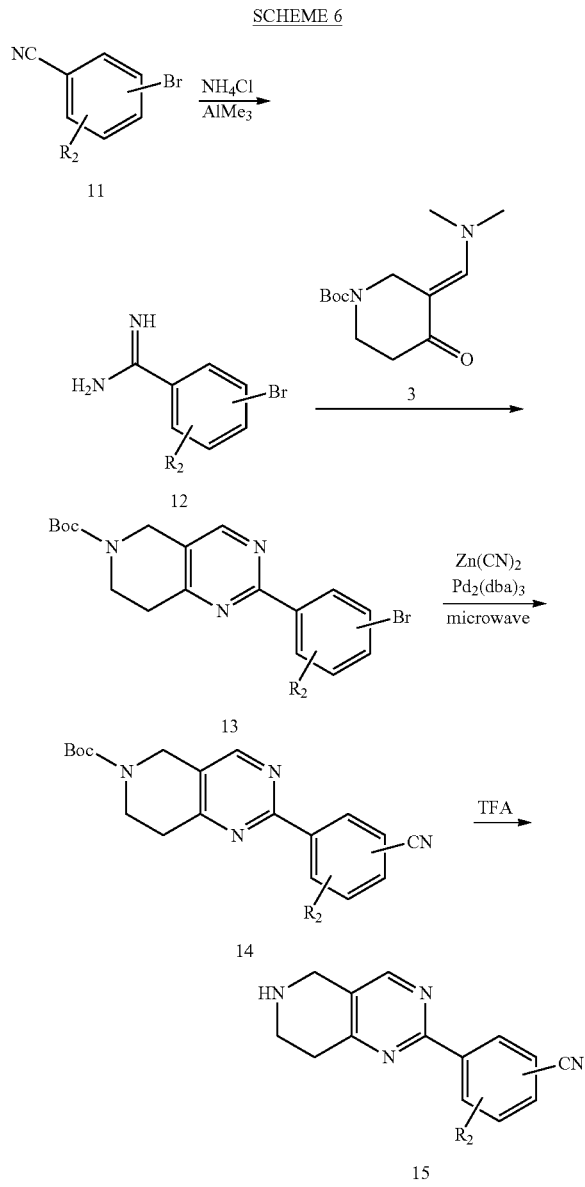

General Procedures:

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-LC/MS).

Typically the analytical LC-LC/MS system used consisted of a Waters ZQ platform with electrospray ionization in positive ion detection mode with an Agilent 1100 series HPLC with autosampler. The column was usually a Water Xterra LC/MS C18, 3.0×50 mm, 5 µm. The flow rate was 1 mL/min, and the injection volume was 10 µL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-LC/MS System Consisting of: Waters ZQ single quad LC/MS system with Electrospray Ionization, Waters 2525 Gradient Pump, Waters 2767 Injector/Collector, Waters 996 PDA Detector, the LC/MS Conditions of: 150-750 amu, Positive Electrospray, Collection Triggered by LC/MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TLC/MS) was used as internal reference in CD$_3$Cl solutions, and residual CH$_3$OH peak or TLC/MS was used as internal reference in CD$_3$OD solutions. Coupling constants (J) were reported in hertz (Hz). Chiral analytical chromatography was performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systeLC/MS. Chiral preparative chromatography was conducted on one of Chiralpak AS, Chiralpak AD, Chiralcel OD, Chiralcel IA, or Chiralcel OJ columns (20×250 mm) (Daicel Chemical Industries, Ltd.) with desired isocratic solvent systeLC/MS identified on chiral analytical chromatography or by supercritical fluid (SFC) conditions.

Abbreviations and tradenames used herein include: Celite® diatomaceous earth; —C(O)CH$_3$ (Ac); acetic acid (AcOH; HOAc); —OC(O)CH$_3$ (OAc); aqueous (aq); benzyloxycarbonyl (Cbz); 1,1'-Carbonyldiimidazole (CDI); dibenzylideneacetone (dba); N,N-diisopropylethylamine (DIPEA); N; N-dimethylformamide (DMF); dimethylsulfide (DLC/MS); 1,2-dichloroethane (DCE); 1-chloroethylchloroformate (ACE-Cl); 1,1'-bis(diphenylphosphino)ferrocene (dppf, DPPF); ethyl acetate (EtOAc); diethyl ether (ether or Et$_2$O); petroleum ether (PE); gram(s) (g); hexane (Hex); hour(s) (h or hr); hexamethylphosphoramide (HMPA); high pressure liquid chromatography (HPLC); 1-hydroxybenzotriazole (HOBT); 2-propanol (IPA); lithium diisopropylamide (LDA); mass spectrum (LC/MS or LC/MS); microliter(s) (µL); milligram(s) (mg); milliliter(s) (mL); millimole (mmol); minute(s) (min); methyl t-butylether (MTBE); medium pressure liquid chromatography (MPLC); N-methylmorpholine-N-oxide (NMO); phenyl (Ph); tetrakis(triphenylphosphine)palladium (Pd(PPh₃)₄); tris(dibenzylidineacetone)dipalladium (Pd₂(dba)₃); retention time (R$_t$); room temperature (rt or RT); saturated aqueous sodium chloride solution (brine); SolkaFloc® cellulose fiber filter aid; N,N,N',N'-Tetramethylethylenediamine (TMEDA); triethylamine (TEA); trifluoroacetic acid (TFA); tetrahydrofuran (THF); flash chromatography (FC); liquid chromatography (LC); liquid chromatography-mass spectrometry (LCLC/MS, LC/LC/MS or LC-LC/MS); supercritical fluid chromatography (SFC); t-butyloxycarbonyl (Boc or BOC); Diethylaminosulfur trifluoride (DAST); Diethylaminodifluorosulfinium tetrafluoroborate (Xtal-Fluor-E); dichloromethane (DCM); dimethylacetamide (DMA; DMAC); dimethylsulfoxide (DLC/MSO); 1,3-Bis(diphenylphosphino)propane (DPPP); 4,5-Bis(diphenylphosphino)-9,9-dimethylxanthene (Xantphos); acetic acid (HOAc); 3-chloroperoxybenzoic acid (m-CPBA); methyl (Me); methanol (MeOH); N-bromosuccinimide (NBS); N-chlorosuccinimide (NCS); thin layer chromatography (TLC).

The following are representative procedures for the preparation of the compounds used in the following Examples, or which can be substituted for the compounds used in the following Examples which may not be commercially available.

Intermediate 1

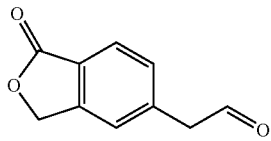 [SMILES: O=CCc1ccc2c(c1)COC2=O]

(1-Oxo-1,3-dihydro-2-benzofuran-5-yl)acetaldehyde

Step A: 5-(1,3-Dioxolan-2-ylmethyl)-2-benzofuran-1(3H)-one

A three-neck 5 L round bottomed flask equipped with a stir bar, firestone valve, thermocouple, condenser and heating mantle was charged with tri-t-butyl phosphonium tetrafluoroborate (500 mg, 1.72 mmol), palladium (II) acetate (250 mg, 1.1 mmol) and 5-bromo-2-benzofuran-1(3H)-one (100 g, 470 mmol). DMF (1.88 L) was added to the flask, and the mixture was degassed three times by alternating vacuum and nitrogen purge. Commercially available bromo (1,3-dioxolan-2-ylmethyl)zinc solution (1.03 L, 516 mmol) was added via cannula and the mixture was again degassed three times. The mixture was then heated at 85° C. for 5 h. Analysis by HPLC-LC/MS indicated the reaction was not complete. The mixture was stirred at 85° C. for 5 more h. The mixture was then allowed to return to rt for 16 h. 2-MethylTHF (2 L) and brine were added, and the mixture was stirred for 5 min. The layers were separated and the aqueous layer was extracted again with 2-methylTHF. The organic layers were combined, washed three times with brine (4 L each), dried over MgSO₄, filtered, and concentrated. The crude product was purified by flash chromatography (1.5 kg silica cartridge), eluting with 0-20% ethyl acetate in dichloromethane to afford 5-(1,3-dioxolan-2-ylmethyl)-2-benzofuran-1(3H)-one. LC/MS (IE, m/z): 221 [M+1]⁺.

Step B: (1-Oxo-1,3-dihydro-2-benzofuran-5-yl)acetaldehyde 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.14 L, 2.29 mol) was added and the resulting mixture was heated at 40° C. for 8 h. Then the mixture was stirred 16 h at rt. The mixture was extracted three times with 2 L of ethyl acetate. The combined organic layers were concentrated to give (1-oxo-1,3-dihydro-2-benzofuran-5-yl)acetaldehyde. LC/MS (IE, m/z): 177 (M+1)⁺.

Intermediate 2

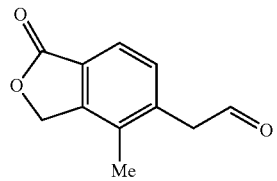 [SMILES: Cc1c(CC=O)ccc2c1COC2=O]

(4-Methyl-1-oxo-1,3-dihydro-2-benzofuran-5-yl)acetaldehyde

Step A: (3-Bromo-2-methylphenyl)methanol

To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1 N HCl, sodium carbonate, and brine. The organic layer was dried over sodium sulfate and concentrated. (3-bromo-2-methylphenyl)methanol.

Step B: 5-Bromo-4-methyl-2-benzofuran-1(3H)-one

To a flask charged with (3-bromo-2-methylphenyl)methanol (6.0 g, 30 mmol) was added a 1 M TFA solution of Thallium Trifluoroacetate (16.2 g, 29.8 mmol). The mixture was stirred at RT 16 h. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at rt. Analysis by LC showed a big product spot within 2 h. To this solution was added ethyl acetate to precipitate the salts. The black solution was filtered through a Celite® pad, washed with EtOAc, adsorbed onto silica and purified by silica gel chromatography. 5-bromo-4-methyl-2-benzofuran-1(3H)-one. $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

Step C: 4-Methyl-5-prop-2-en-1-yl-2-benzofuran-1 (3H)-one

To a flask charged with 5-bromo-4-methyl-2-benzofuran-1(3H)-one (320 mg, 1.409 mmol) and a stir bar was added allyl tri-n-butyltin (0.655 mL, 2.11 mmol), Pd(PPh$_3$)$_4$ (244 mg, 0.211 mmol), lithium chloride (179 mg, 4.23 mmol), and toluene (15 mL). The reaction was purged with nitrogen 2 times then was heated at reflux for 4 h. The product was separated by silica gel chromatography to give 4-methyl-5-prop-2-en-1-yl-2-benzofuran-1 (3H)-one.

Step D: (4-Methyl-1-oxo-1,3-dihydro-2-benzofuran-5-yl)acetaldehyde

A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DLC/MS (0.870 mL, 11.7 mmol). The reaction was allowed to warm up to RT. The crude product was purified by flash chromatography to afford the title compound. $^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

Intermediate 3

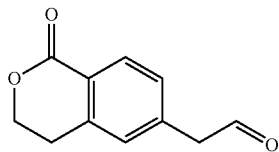 [SMILES: O=CCc1ccc2c(c1)CCOC2=O]

2-(1-oxoisochroman-6-yl)acetaldehyde

Step A: 6-(1,3-dioxolan-2-ylmethyl)-3,4-dihydro-1H-isochromen-1-one 6-bromo-3,4-dihydro-1H-isochromen-1-one (10 g, 44 mmol) was combined with tri-t-butyl phosphonium tetrafluoroborate (256 mg, 0.881 mmol), palladium (II) acetate (99 mg, 0.44 mmol) and commercially available bromo(1,3-dioxolan-2-ylmethyl)zinc solution (0.5 M, 97 mL, 48 mmol) in DMF (100 mL) and the mixture was degassed 3 times by alternating vacuum and nitrogen purge. The mixture was then heated at 85° C. for 6 h, then was stirred at rt for 16 h. Ethyl acetate and ether were added and the mixture was washed with water. The aqueous layer was extracted with ethyl acetate, the organic layers were combined and washed twice with water and once with brine. The organic layer was dried over MgSO$_4$, filtered and concentrated. The crude product was purified by MPLC (silica) eluting with ethyl acetate in hexanes to afford the title compound. LCLC/MS: m/z 235 (M+1)$^+$.

Step B: (1-oxo-3,4-dihydro-1H-isochromen-6-yl)acetaldehyde 6-(1,3-Dioxolan-2-ylmethyl)-3,4-dihydro-1H-isochromen-1-one (4.42 g, 18.9 mmol) was dissolved in dioxane (25 mL) and treated with 3 M HCl (40 mL). The reaction mixture was stirred at rt overnight, then was warmed to 50° C. for 2 h to drive the reaction to completion. However this led to increased side product production based on LCLC/MS. Ethyl acetate was added and the layers were separated. The aqueous layer was extracted again with ethyl acetate and the combined organic layers were washed with brine and dried over MgSO$_4$ to afford the title compound. LCLC/MS: m/z 191 (M+1)$^+$.

Intermediate 4

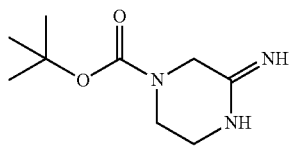

tert-butyl-3-amino-5,6-dihydropyrazine-1(2H)-carboxylate

Step A: tert-butyl 3-ethoxy-5,6-dihydropyrazine-1 (2H)-carboxylate

To a solution of tert-butyl 3-oxopiperazine-1-carboxylate (2.0 g, 9.99 mmol) in DCM (20 ml) was added triethyloxonium tetrafluoroborate (2.01 g, 10.99 mmol) and stirred at rt. The mixture was partitioned between EtOAc and aq NaHCO$_3$ (sat'd) and aqueous layer was extracted with EtOAc (3×). Combined organic layer was washed with brine, dried over MgSO$_4$, filtered, concentrated to give the title product as viscous oil. LC/MS: [M−$^{56+H}$]=173.3

Step B: tert-butyl-3-amino-5,6-dihydropyrazine-1 (2H)-carboxylate

To tert-butyl 3-ethoxy-5,6-dihydropyrazine-1(2H)-carboxylate in a RB-flask (100 ml) was added 7N NH$_3$ in MeOH (20 ml) at rt and the mixture was stirred at rt for 18 h. The reaction mixture was concentrated after 18 hr to give the title compound as a viscous oil. LC/MS: [M+H]$^+$=200.2

Intermediate 5

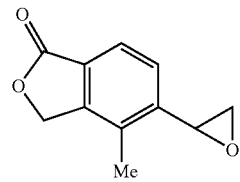 [SMILES: Cc1c(C2CO2)ccc2c1COC2=O]

4-methyl-5-oxiran-2-yl-2-benzofuran-1(3H)-one

Step A: 5-ethenyl-4-methyl-2-benzofuran-1 (3H)-one

5-Bromo-4-methyl-2-benzofuran-1 (3H)-one (598 mg, 4.47 mmol), potassium vinyl trifluoroborate (507 mg, 2.23 mmmol), PdCl$_2$(dppf)-CH$_2$Cl$_2$ Adduct (182 mg, 0.223 mmmol) and TEA (0.622 mL, 4.47 mmol) were added to 10 mL ethanol in a 20 mL microwave tube. The tube was sealed and degassed, then heated to 140° C. for 20 min. Analysis by LC-LC/MS showed product peak. The reaction mixture was diluted with ethyl acetate, washed with brine twice, dried and evaporated to dryness. The crude product was purified by MPLC chromatography using a 120 g Redi-sep column and 0-80% ETOAC/Hexane solvent system to yield 5-ethenyl-4-methyl-2-benzofuran-1(3H)-one. $^1$H-NMR (500 MHz, CDCl$_3$): δ ppm 7.76 (d, J=8 Hz, 1H), 7.03 (dd, J=11, 17 Hz, 1H), 5.84 (d, J=17 Hz, 1H), 5.55 (d, J=11 Hz, 1H), 5.29 (s, 2H), 2.34 (s, 3H); LC-LC/MS: M+1=175;

Step B: 4-methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT 16 h. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC chromatography through 120 g Redi-sep column eluting with 0-80% EtOAc/hexane solvent system to yield target 4-methyl-5-oxiran-2-yl-2-benzofuran-1(3H)-one. $^1$H-NMR (500 MHz, CDCl$_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H). LC-LC/MS: M+1=191.

Intermediates 5A and 5B (Method 1)

5A: 4-methyl-5-[(2S)-oxiran-2-yl]-2-benzofuran-1(3H)-one

5B: 4-methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO2, flow rate 200 mL/min, 100 bar, 25° C. 500 ul Injections were spaced every 2.12 mins. The fast epoxide (4-methyl-5-[(2R)-oxiran-2-yl]-2-benzofuran-1(3H)-one, 4B) eluted first, and the slow epoxide (4-methyl-5-[(2S)-oxiran-2-yl]-2-benzofuran-1 (3H)-one, 4A) eluted second.

Alternatively, the resolution could also be achieved using a mobile phase of 8% MeOH/98% CO$_2$ with a flow rate of 100 mL/min. In that case the sample was prepared by dissolving in methanol, 20 mg/mL, and using a 1 mL volume per injection. After separation, the fractions were dried off via rotary evaporator at bath temperature 40° C.

The absolute stereochemistry of each enantiomer was inferred based on the X-ray crystal structure determination of a final compound made with 4B and by Mosher ester and Trost ester HNMR analysis of esters made starting from 4B. Both epoxide isomers find utility in the present invention.

Intermediate 6

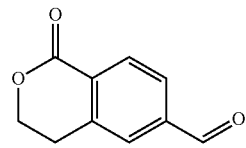 [SMILES: O=Cc1ccc2c(c1)CCOC2=O]

2-(1-oxoisochroman-6-yl)acetaldehyde

Step A: 6-bromoisochroman-1-one

LDA (11.63 ml, 17.44 mmol) was dissolved in THF (50 ml) and cooled to −78° C., 4-bromo-2-methylbenzoic acid (1.0 g, 4.65 mmol) in THF (10 ml) was added to the mixture and the mixture was stirred for 10 minutes at −70° C. This was followed by the addition of paraformaldehyde (559 mg, 18.60 mmol), and the resulting mixture was stirred at rt for 4 h. The reaction mixture was poured into 1N HCl (aq.) and extracted with ether (2×). Combined organic layers were washed with brine, dried over anhydrous MgSO$_4$, filtered, concentrated and purified by silica gel column chromatography (112 g, Analogix column) using (0-100)% ethyl acetate/hexanes as mobile phase to get the title product. from a 115 g. Analogixcolumn. LC/MS: [M+H]$^+$=229

Step B: 6-((1,3-dioxolan-2-yl)methyl)isochroman-1-one 6-bromo-3,4-dihydro-1H-isochromen-1-one (10 g, 44 mmol) was combined with tri-t-butyl phosphonium tetrafluoroborate (256 mg, 0.881 mmol), palladium (II) acetate (99 mg, 0.44 mmol) and commercially available bromo(1,3-dioxolan-2-ylmethyl)zinc solution (0.5 M, 97 mL, 48 mmol) in DMF (100 mL) and the mixture was degassed 3 times by alternating vacuum and nitrogen purge. The mixture was then heated at 85° C. for 6 h, then was stirred at rt for 16 h. Ethyl acetate and ether were added and the mixture was washed with water. The aqueous layer was extracted with ethyl acetate, the organic layers were combined and washed twice with water and once with brine. The organic layer was dried over MgSO$_4$, filtered and concentrated. The crude product was purified by MPLC (silica) eluting with ethyl acetate in hexanes to afford the title compound. LC/MS: [M+H]$^+$=235

Step C: (1-oxo-3,4-dihydro-1H-isochromen-6-yl)acetaldehyde 6-(1,3-Dioxolan-2-ylmethyl)-3,4-dihydro-1H-isochromen-1-one (4.42 g, 18.9 mmol) was dissolved in dioxane (25 mL) and treated with 3 M HCl (40 mL). The reaction mixture was stirred at rt over night, then was warmed to 50° C. for 2 h to drive the reaction to completion. (However this led to increased side product production based on LCLC/MS). Ethyl acetate was added and the layers were separated. The aqueous layer was extracted again with ethyl acetate and the combined organic layers were washed with brine and dried over MgSO$_4$ to afford the title compound. LC/MS: [M+H]$^+$=191.

Intermediate 7

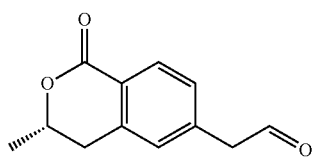

(S)-2-(3-methyl-1-oxoisochroman-6-yl)acetaldehyde

Step A: 6-bromo-3-methylisochroman-1-one

A solution of diisopropylamine (13 ml, 93 mmol) in THF (155 ml) at −78° C. was treated with n-BuLi (1.6 M in Hexanes: 58 ml, 93 mmol) over a period of 15 minutes using a syringe pump. In a separate flask, a solution of 2-methyl-4-bromobenzoic acid (10 g, 46 mmol) and HMPA (8.3 ml, 46 mmol) in THF (155 ml) was cooled to −78° C. Methyl Lithium (29 ml, 46 mmol) was added slowly via syringe to the cooled solution in order to make the lithio carboxylate. The resulting solution was stirred for 10 minutes and then transferred via cannula to the LDA solution at −78° C. The resulting bright red solution was stirred at −78° C. for an additional 1 hour before being quenched with anhydrous acetaldehyde (7.9 ml, 140 mmol) (color changed from red to orange to clear yellow) and the reaction was then taken out of the dry ice acetone bath and allowed to stir for an additional 1 hour. The flask containing the reaction mixture was then resubmerged in the dry ice acetone bath before it was quenched with 4 M HCl in Dioxane (50 mL) followed by 25 mL of MeOH. The reaction was stirred at room temp for an additional 1 hour. The crude reaction was partitioned b/w 200 mL EtOAc and 200 mL water. The organic layer was washed with water, brine, dried with mag. sulfate, filtered and concentrated. Purification via MPLC (30-70% DCM/hexanes) yielded 6-bromo-3-methyl-3,4-dihydro-1H-isochromen-1-one as an off white solid. $^1$H NMR (500 MHz; CDCl$_3$): 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H). LC-LC/MS (IE, m/z): 241 [M+1]$^+$.

Chiral separation of racemic 6-bromo-3-methyl-3,4-dihydro-1H-isochromen-1-one was achieved using ChiralPak AS 4.6×250 mm 10 u column, eluting with 60% IPA/Heptane. The faster eluting isomer was identified as the S-isomer. (3S)-6-Bromo-3-methyl-3,4-dihydro-1H-isochromen-1-one. $^1$H NMR (500 MHz, CDCl$_3$): 7.98 (d, J=8.2 Hz, 1H), 7.56 (dd, J:=1.5, 8.2 Hz, 1H), 7.45 (s, 1H), 4.71 (m, 1H), 2.94 (m, 2H), 1.55 (d, J=6.3 Hz, 3H). LC-LC/MS (IE, m/z): 241 [M+1]$^+$.

Step B: (R)-6-((1,3-dioxolan-2-yl)methyl)-3-methylisochroman-1-one

A sealed tube was charged with 6-bromo-3-methylisochroman-1-one (35 mg, 0.145 mmol), ((1,3-dioxolan-2-yl)methyl)zinc(II) bromide (0.29 ml, 0.006 mmol), palladium acetate (1.304 mg, 5.81 µmol) and butylphosphonium tetrafluoroborate (3.37 mg, 0.012 mmol), DMF (0.58 ml) and sealed. The tube was evacuated and refilled with nitrogen and heated to 110° C. in the microwave for 75 minutes. The reaction mixture was diluted with EtOAc, filtered, concentrated and purified via MPLC using (20-50)% Ethyl acetate/ Hexane as mobile phase to afford the title product as a clear oil which solidified on standing. LC/MS: [M+H]$^+$=249

Step C: (R)-2-(3-methyl-1-oxoisochroman-6-yl)acetaldehyde

A 1:1 solution of dioxane: 3N HCl was added to a flask containing (3R)-6-(1,3-dioxolan-2-ylmethyl)-3-methyl-3,4-dihydro-1H-isochromen-1-one (782 mg, 3.15 mmol). The reaction was then stirred at room temp 16 h. The crude reaction mixture was then partitioned between water and DCM. The organic layer was washed with saturated sodium bicarbonate solution, followed by brine. The organic layer was then dried with mag. sulfate, filtered and concentrated to afford [(3R)-3-methyl-1-oxo-3,4-dihydro-1H-isochromen-6-yl]acetaldehyde. LC/MS: [M+H]$^+$=205.3

Intermediate 8

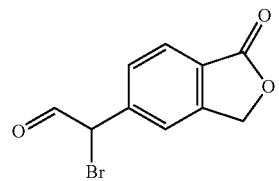 [SMILES: O=CC(Br)c1ccc2c(c1)COC2=O]

2-bromo-2-(1-oxo-1,3-dihydroisobenzofuran-5-yl)acetaldehyde

Step A: 2-bromo-2-(1-oxo-1,3-dihydroisobenzofuran-5-yl)acetaldehyde

To a solution of 1-Oxo-1,3-dihydro-2-benzofuran-5-yl)acetaldehyde (Intermediate 1) (795 mg, 4.51 mmol) in THF (28.4 ml) was added phenyltrimethylammonium tribromide (2.2 g, 5.85 mmol) at rt. The reaction mixture was then cooled to 0° C. in an ice bath and stirred for 3 min. The mixture was filtered, concentrated and purified by silica gel column chromatography using (0-100)% MeOH/DCM as mobile phase to give the title compound as yellow viscous oil.

Intermediate 9

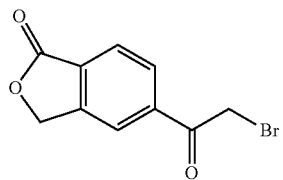 [SMILES: O=C(CBr)c1ccc2c(c1)COC2=O]

5-(-2-bromoacetyl)isobenzofuran-1(3H)-one

Step A: 5-acetylisobenzofuran-1(3H)-one

To a mixture of 5-bromoisobenzofuran-1(3H)-one (2.0 g, 9.39 mmol), butyl vinyl ether (4.70 g, 46.9 mmol), 1,3-bis(diphenylphosphino)propane (194 mg, 0.469 mmol), palladium acetate (105 mg, 0.469 mmol) and 1-butyl-3-methylimidazolium tetrafluoroborate (1.061 g, 4.69 mmol) in DLC/MSO (9.39 ml) was added diisopropylamine (1.606 ml, 11.27 mmol) in a microwave vial. The reaction mixture was degassed with argon and stirred at 115° C. for 18 h. The mixture was partitioned between EtOAc and H$_2$O. After separation of layers, the aqueous layer was extracted with EtOAc (3×) and combined organic layers were washed with brine, dried over anhydrous MgSO$_4$, and filtered, concentrated. The residue was then dissolved in MeOH/DLC/MSO (50 ml/10 ml), 3N HCl (40 ml) was added and the resulting mixture was stirred at rt for 3 h. After concentration the residue was partitioned between DCM and water and after separation of layers the aqueous layer was extracted with DCM (3×). The combined organic layers were washed with brine, dried over anhydrous MgSO$_4$, filtered, concentrated and purified by silica gel column chromatography using (0-100)% EtOAc/Hexanes as mobile phase to get the title compound as yellow solid. LC/MS: [M+H]$^+$=177.3

Step B: 5-(-2-bromoacetyl)isobenzofuran-1(3H)-one

To a solution of 5-acetylisobenzofuran-1(3H)-one (2.93 g, 16.67 mmol) in THF (83 ml) was added copper(II) bromide (4.10 g, 18.34 mmol) at rt and the resulting mixture was stirred at rt for 18 h. The mixture was partitioned between EtOAc and H$_2$O and after separation of layers the aqueous layer was extracted with EtOAc (3×). The combined organic layers were washed with brine, dried over anhydrous MgSO$_4$ and filtered. Concentration of the filtrate gave the crude product which was purified by silica gel column chromatography using (0-60)% EtOAc/Hexanes as mobile phase and the pure title compound was isolated as a pale yellow solid. LC/MS: [M+H]$^+$=255-257

Intermediate 10

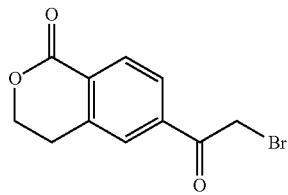 [SMILES: O=C(CBr)c1ccc2c(c1)CCOC2=O]

6-(2-bromoacetyl)isochroman-1-one

Step A: 6-bromoisochroman-1-one

LDA (11.63 ml, 17.44 mmol) was dissolved in THF (50 ml) and cooled to at −78° C., 4-bromo-2-methylbenzoic acid (1.0 g, 4.65 mmol) in THF (10 ml) was added stirred for 10 mins. This was followed by the addition of paraformaldehyde (559 mg, 18.60 mmol) and the resulting mixture was stirred at rt for 4 h. The reaction mixture was poured into 1N HCl and extracted with ether (2×). Combined organic layers were washed with brine, dried over anhydrous MgSO$_4$, filtered, concentrated and purified by silica gel column chromatography (115 g, Analogix column) eluting with (0-100)% Ethyl acetate/Hexanes to get the title product. LC/MS: [M+H]$^+$=229.

Step B: 6-acetylisochroman-1-one

To a mixture of 6-bromoisochroman-1-one (1 g, 4.40 mmol), Butyl vinyl ether (2.83 ml, 22.02 mmol), 1,3-bis (diphenylphosphino)propane (0.091 g, 0.220 mmol), Palladium acetate (0.049 g, 0.220 mmol) and 1-butyl-3-methylimidazolium tetrafluoroborate (0.498 g, 2.202 mmol) in DLC/MSO (4.40 ml) was added diisopropylamine (0.753 ml, 5.29 mmol) in a microwave vial and the reaction mixture was degassed with argon and stirred at 115° C. for 18 h. The mixture was partitioned between EtOAc and water and the aqueous layer was extracted with EtOAc (3×). The combined organic layers were washed with brine, dried over anhydrous MgSO4, filtered and concentrated. The residue was then dissolved in MeOH/DLC/MSO (50 ml/10 ml), 3N HCl (40 ml) was added to that and the resulting mixture was stirred at rt for 3 h. After concentration the residue was partitioned between DCM and water and the aqueous layer was extracted with DCM (3×). The combined organic phase was washed with brine, dried over anhydrous MgSO$_4$, and filtered, concentrated which was followed by purification by silica gel column chromatography using (0-60)% EtOAc/Hexanes as mobile phase to give the title compound as yellow solid. LC/MS: [M+H]$^+$=191.2

Step C: 6-(2-bromoacetyl)isochroman-1-one 6-(1,3-Dioxolan-2-ylmethyl)-3,4-dihydro-1H-isochromen-1-one (4.42 g, 18.9 mmol) was dissolved in dioxane (25 mL) and treated with 3 M HCl (40 mL). The reaction mixture was stirred at rt overnight and then was warmed to 50° C. for 2 h to drive the reaction to completion (however this led to increased side product production based on LCLC/MS). Ethyl acetate was added and the layers were separated. The aqueous layer was extracted again with ethyl acetate and the combined organic layers were washed with brine, dried over MgSO$_4$, filtered, concentrated to afford the title compound. LC/MS: [M+H]=269.1

Intermediate 11

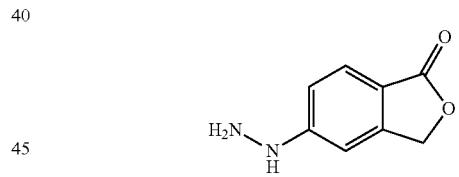

5-hydrazinylisobenzofuran-1(3H)-one

Step A: 5-hydrazinylisobenzofuran-1(3H)-one 5-aminophthalide (1.5 g, 10.06 mmol) was dissolved in concentrated HCl (10 ml) and cooled to −10° C. and was stirred vigorously while adding a solution of sodium nitrite (530 mg, 7.68 mmol) in Water (10 ml) dropwise over a period of 1 h. A cold solution of tin(II) chloride (6.9 g, 36.4 mmol) in conc. HCl (9 ml) was added slowly, making sure the temp never rose above −5° C. (NaCl was added to the ice bath to maintain the temp). The reaction mixture was then brought to a pH 14 using 5N NaOH and then diluted with chloroform. After separation of layers, the aqueous layer was extracted with chloroform (2×), combined organic phase was washed with brine, dried over anhydrous MgSO$_4$, filtered and concentrated to get the title product as yellow powder which was used for next step without purification. LC/MS: [M+H]$^+$=165.2

Intermediate 12

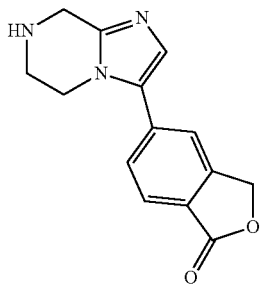 [SMILES: O=C1OCc2cc(-c3cnc4n3CCNC4)ccc21]

5-(5,6,7,8-tetrahydroimidazo[1,2-a]pyrazin-3-yl) isobenzofuran-1 (3H)-one

Step A: tert-butyl-3-(1-oxo-1,3-dihydroisobenzofuran-5-yl)-5,6-dihydroimidazo[1,2-α]pyrazine-7(8H)-carboxylate To a solution of tert-butyl-3-amino-5,6-dihydropyrazine-1(2H)-carboxylate (220 mg, 1.106 mmol) in 2-propanol (5 ml) at rt was added 2-bromo-2-(1-oxo-1,3-dihydroisobenzofuran-5-yl)acetaldehyde (235 mg, 0.921 mmol), and the solution was microwaved for 30 mins at 100° C. The reaction mixture was partitioned between EtOAc and aqueous NaHCO$_3$ (saturated) and after separation of layers, the aqueous layer was extracted with EtOAc (2×). The combined organic phase was washed with brine, dried over anhydrous MgSO$_4$, filtered, concentrated and purified by preparative TLC using 10% MeOH/DCM as mobile phase to give the title compound as yellow solid. LC/MS: [M+H]$^+$=356.3

Step B: 5-(5,6,7,8-tetrahydroimidazo[1,2-a]pyrazin-3-yl)isobenzofuran-1 (3H)-one tert-butyl-3-(1-oxo-1,3-dihydroisobenzofuran-5-yl)-5,6-dihydroimidazo[1,2-α]pyrazine-7(8H)-carboxylate (47.8 mg, 0.135 mmol) was dissolved in HCl, 4M in 1,4-dioxane, (10 ml, 40.0 mmol) at rt and stirred for 2 h. A few drops of MeOH was added to help with solubility. The mixture was then concentrated to give the title compound as a solid which was used for the next step without further purification. LC/MS: [M+H]$^+$=256.3

Intermediate 13

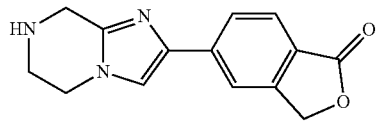 [SMILES: O=C1OCc2cc(-c3cn4c(n3)CNCC4)ccc21]

5-(5,6,7,8-tetrahydroimidazo[1,2-a]pyrazin-2-yl) isobenzofuran-1 (3H)-one

Step A: tert-butyl-2-(1-oxo-1,3-dihydroisobenzofuran-5-yl)-5,6-dihydroimidazo[1,2-α]pyrazine-7(8H)-carboxylate To a solution of tert-butyl-3-amino-5,6-dihydropyrazine-1(2H)-carboxylate (220 mg, 1.106 mmol) in 2-propanol (5 ml) at rt was added 2-bromo-2-(1-oxo-1,3-dihydroisobenzofuran-5-yl)acetaldehyde (235 mg, 0.921 mmol). The reaction was microwaved for 30 mins at 100° C. The reaction mixture was partitioned between EtOAc and aqueous NaHCO$_3$ (saturated) and after separation of layers, the aqueous layer was extracted with EtOAc (2×). The combined organic phase was washed with brine, dried over anhydrous MgSO$_4$, filtered, concentrated and purified by preparative TLC using 10% MeOH/DCM as mobile phase to give the title compound as yellow solid. LC/MS: [M+H]$^+$=356.3

Step B: 5-(5,6,7,8-tetrahydroimidazo[1,2-a]pyrazin-2-yl)isobenzofuran-1(3H)-one tert-butyl-2-(1-oxo-1,3-dihydroisobenzofuran-5-yl)-5,6-dihydroimidazo[1,2-α]pyrazine-7(8H)-carboxylate (56.8 mg, 0.160 mmol) was dissolved in HCl, 4M in 1,4-dioxane (10 ml, 40.0 mmol) at rt. A few drops of MeOH was added to help with solubility. The reaction mixture was stirred at rt for 2 h. The mixture was then concentrated to give the title product as a tan powder which was used for the next reaction without purification. LC/MS: [M+H]$^+$=256.3

Intermediate 14

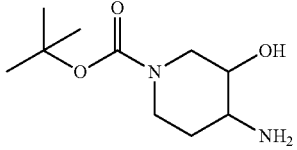

tert-butyl 4-amino-3-hydroxypiperidine-1-carboxylate

Step A: tert-butyl 7-oxa-3-azabicyclo[4.1.0]heptane-3-carboxylate

To a solution of tert-butyl 5,6-dihydropyridine-1(2H)-carboxylate (0.3627 g, 1.979 mmol) in CH$_2$Cl$_2$ (5 ml) at 0° C. was added a solution of mCPBA (0.53 g, 3.07 mmol) in CH$_2$Cl$_2$ (5 ml). The resulting reaction mixture was allowed to warm to rt and stirred over the weekend. The reaction was partitioned between EtOAc and 5% Na$_2$S$_2$O$_3$. After separation of layers, the organic layer was washed with sat. NaHCO$_3$, brine, dried over anhydrous MgSO$_4$, filtered and concentrated to give the title compound as colorless oil.

Step B: tert-butyl 4-azido-3-hydroxypiperidine-1-carboxylate

To a solution of tert-butyl 7-oxa-3-azabicyclo[4.1.0]heptane-3-carboxylate (9.71 g, 48.7 mmol) in EtOH/water (210 ml/70 ml) was added sodium azide (7.92 g, 122 mmol) followed by ammonium chloride (5.21 g, 97 mmol), and the resulting mixture was heated at 70° C. for 18 h. The reaction mixture was concentrated and partitioned between EtOAc and brine. After separation of layers, the aqueous layer was extracted with EtOAc (3×), the combined organic layer was washed with brine and dried over MgSO$_4$, filtered, concentrated and purified by silica gel column chromatography using (0-50)% EtOAc/Hexane as eluent to get the title product.

Step C: tert-butyl 4-amino-3-hydroxypiperidine-1-carboxylate

To a solution of tert-butyl 4-azido-3-hydroxypiperidine-1-carboxylate (1 g, 4.13 mmol) in MeOH (20.64 ml) was added palladium (10 wt. %) (100 mg, 4.13 mmol) at rt. A hydrogen balloon was attached to the flask and the reaction was stirred at rt 16 h. The reaction mixture was filtered over celite to remove palladium and the filtrate was concentration gave the title product as a clear viscous oil, which was directly used in the next step without further purification.

Intermediate 15

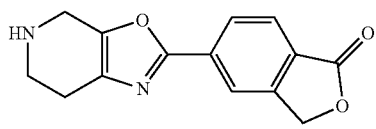 [SMILES: O=C1OCc2cc(-c3nc4c(o3)CNCC4)ccc21]

5-(4,5,6,7-tetrahydrooxazolo[5,4-c]pyridin-2-yl)isobenzofuran-1(3H)-one

Step A: tert-butyl 3-hydroxy-4-(1-oxo-1,3-dihydroisobenzofuran-5-carboxamido)piperidine-1-carboxylate To a solution of 5-carboxyphthalide (60 mg, 0.337 mmol), tert-butyl 4-amino-3-hydroxypiperidine-1-carboxylate (72.8 mg, 0.337 mmol), HOBT (61.9 mg, 0.404 mmol), and EDC (97 mg, 0.505 mmol) in DCM (1684 μl) was added N-methylmorpholine (74.1 μl, 0.674 mmol) at rt and the reaction mixture was stirred at rt 16 h. The mixture was concentrated and the residue was purified by preparative TLC using 10% MeOH/DCM as mobile phase to give the title compound as white solid. LC/MS: [M+H]$^+$=377.1

Step B: tert-butyl 3-oxo-4-(1-oxo-1,3-dihydroisobenzofuran-5-carboxamido)piperidine-1-carboxylate To a solution of tert-butyl 3-hydroxy-4-(1-oxo-1,3-dihydroisobenzofuran-5-carboxamido)piperidine-1-carboxylate (396 mg, 1.052 mmol) in DCM (10 ml) was added Dess-MartinPeriodinane (535 mg, 1.262 mmol) and the resulting mixture was stirred vigorously at rt for 50 minutes. The reaction mixture was diluted with 10% Na$_2$S$_2$O$_3$, solid NaHCO$_3$ was added and the resulting mixture was stirred for 20 mins at rt. After separation of layers, the aqueous layer was extracted with DCM (2×), combined organic layers were washed with brine, dried over anhydrous Na$_2$SO$_4$, and concentrated to give the crude aldehyde, the title compound, as solid which was used without further purification.

Step C: tert-butyl 2-(1-oxo-1,3-dihydroisobenzofuran-5-yl)-6,7-dihydrooxazolo[5,4-c]pyridine-5(4H)-carboxylate To a solution of tert-butyl 3-oxo-4-(1-oxo-1,3-dihydroisobenzofuran-5-carboxamido)piperidine-1-carboxylate (362 mg, 0.967 mmol) in THF (10 ml) was added Burgess reagent (346 mg, 1.45 mmol) at rt and the mixture was refluxed for 16 h. The mixture was partitioned between EtOAc and aq NaHCO$_3$ (sat'd) and aqueous layer was extracted with EtOAc (3×). Combined organic layer was washed with brine, dried over MgSO$_4$, filtered, concentrated followed by purification by silica gel column chromatography using (0-100)% EtOAc/Hexanes to gave the title product as solid. LC/MS: [M+H]$^+$=357.1

Step D: 5-(4,5,6,7-tetrahydrooxazolo[5,4-c]pyridin-2-yl)isobenzofuran-1(3H)-one tert-butyl 2-(1-oxo-1,3-dihydroisobenzofuran-5-yl)-6,7-dihydrooxazolo[5,4-c]pyridine-5 (4H)-carboxylate (80 mg, 0.221 mmol) was dissolved in 4N-HCl in 1,4-dioxane (4 ml) at rt and stirred for 1 hr. The reaction mixture was concentrated to get 2-(1-oxo-1,3-dihydroisobenzofuran-5-yl)-4,5,6,7-tetrahydrooxazolo[5,4-c]pyridin-5-ium chloride as solid.

Intermediate 16

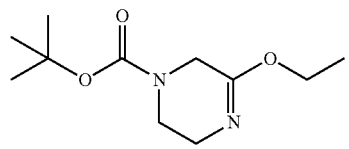 [SMILES: CCOC1=NCCN(C(=O)OC(C)(C)C)C1]

Step A: tert-butyl 3-ethoxy-5,6-dihydropyrazine-1 (2H)-carboxylate

To a solution of tert-butyl 3-oxopiperazine-1-carboxylate (2.0 g, 9.99 mmol) in DCM (20 ml) was added triethyloxonium tetrafluoroborate (2.087 g, 10.99 mmol) at rt. The mixture was partitioned between EtOAc and aq. NaHCO$_3$ (sat'd) and after separation of layers, the aqueous layer was extracted with EtOAc (3×). Combined organic layer was washed with brine, dried over MgSO$_4$ and concentrated to give the title compound as viscous oil. LC/MS: [M+H]$^+$=229.4

Intermediate 17

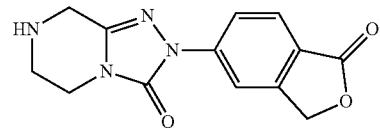 [SMILES: O=C1OCc2cc(-n3nc4n(c3=O)CCNC4)ccc21]

2-(1-oxo-1,3-dihydroisobenzofuran-5-yl)-5,6,7,8-tetrahydro-[1,2,4]triazolo[4,3-a]pyrazin-3(2H)-one

Step A: tert-butyl 3-(2-(1-oxo-1,3-dihydroisobenzofuran-5-yl)hydrazinyl)-5,6-dihydropyrazine-1(2H)-carboxylate To tert-butyl 3-ethoxy-5,6-dihydropyrazine-1(2H)-carboxylate (220 mg, 1.340 mmol) in DLC/MSO (7 ml) was added 5-hydrazinylisobenzofuran-1(3H)-one (306 mg, 1.340 mmol) at rt and the mixture was heated at 100° C. for 18 h. The reaction mixture was partitioned between EtOAc and aqueous NaHCO$_3$ (saturated) and the aqueous layer was extracted with EtOAc (2×). The combined organic phase was washed with brine, dried over anhydrous MgSO$_4$, filtered and concentrated to give the title product as orange/brown viscous oil. The crude was used in the next step without further purification. LC/MS: [M+H]⁺=347.1

Step B: 2-(1-oxo-1,3-dihydroisobenzofuran-5-yl)-5,6,7,8-tetrahydro-[1,2,4]triazolo[4,3-a]pyrazin-3(2H)-one To tert-butyl 3-(2-(1-oxo-1,3-dihydroisobenzofuran-5-yl) hydrazinyl)-5,6-dihydropyrazine-1(2H)-carboxylate (397 mg, 1.146 mmol) in THF (5731 μl) was added CDI (204 mg, 1.261 mmol) at rt and the mixture was refluxed 16 h. The mixture was partitioned between EtOAc and NaHCO₃ and the aqueous layer was extracted with EtOAc (2×). Combined organic phase was washed with brine, dried over anhydrous MgSO₄, and filtered. Concentration of the filtrate was followed by purification by chromatography using a Biotage system using (0-100)% EtOAc/Hexanes as solvent system to give the boc intermediate as a pale yellow powder. The boc intermediate (40 mg, 0.107 mmol) was then dissolved in 4 M HCl in 1,4-dioxane (5 ml). A few drops of MeOH were added for solubility. The solution was stirred at rt 16 h and then concentrated gave the title compound as a pale yellow powder. LC/MS: [M+H]⁺=273.2

Intermediate 18

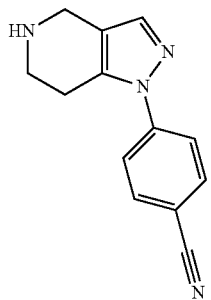 [SMILES: N#Cc1ccc(-n2ncc3c2CCNC3)cc1]

4-(4,5,6,7-tetrahydro-1H-pyrazolo[4,3-c]pyridin-1-yl)benzonitrile

Step A: tert-butyl 1-(4-cyanophenyl)-6,7-dihydro-1H-pyrazolo[4,3-c]pyridine-5(4H)-carboxylate To a solution of (Z)-tert-butyl 3-((dimethylamino)methylene)-4-oxopiperidine-1-carboxylate (1.0 g, 3.93 mmol) in EtOH (10 ml) was added 2-(4-cyanophenyl)hydrazin-1-ium chloride (667 mg, 3.93 mmol) followed by sodium carbonate (833 mg, 7.86 mmol) and the resulting mixture was refluxed for 16 h. The mixture was partitioned between EtOAc and water and aqueous layer was extracted with EtOAc (3×). Combined organic layer was washed with brine, dried over MgSO₄ and filtered. Concentration of filtrate gave dark solid which was purified by silica gel column chromatography using (0-100)% EtOAc/Hexanes as solvent system to give the title product. LC/MS: [M+H]⁺=325.3

Step B: 4-(4,5,6,7-tetrahydro-1H-pyrazolo[4,3-c]pyridin-1-yl)benzonitrile tert-butyl 1-(4-cyanophenyl)-6,7-dihydro-1H-pyrazolo[4,3-c]pyridine-5(4H)-carboxylate (230 mg, 0.709 mmol) was dissolved in 1.25 N HCl in MeOH (5 ml) and stirred at rt for 4 h. The reaction mixture was then concentrated to give the title product as solid. LC/MS: [M+H]⁺=225.3

Intermediate 19

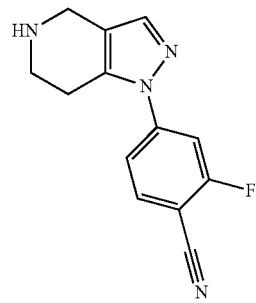 [SMILES: N#Cc1ccc(-n2ncc3c2CCNC3)cc1F]

2-fluoro-4-(4,5,6,7-tetrahydro-1H-pyrazolo[4,3-c]pyridin-1-yl)benzonitrile

The title compound was prepared in an analogous fashion to that described for 1-(4-cyanophenyl)-4,5,6,7-tetrahydro-1H-pyrazolo[4,3-c]pyridine-2,5-diium chloride, except in Step A, where 2-fluoro-4-hydrazinylbenzonitrile was used in the place of 2-(4-cyanophenyl)hydrazin-1-ium chloride.

Intermediate 20

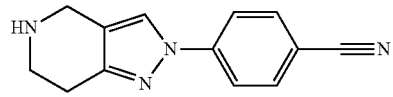

4-(4,5,6,7-tetrahydro-2H-pyrazolo[4,3-c]pyridin-2-yl)benzonitrile

Step A: tert-butyl 2-(4-cyanophenyl)-6,7-dihydro-2H-pyrazolo[4,3-c]pyridine-5(4H)-carboxylate To a solution of (Z)-tert-butyl 3-((dimethylamino)methylene)-4-oxopiperidine-1-carboxylate (1.0 g, 3.93 mmol) in EtOH (10 ml) was added 2-(4-cyanophenyl)hydrazin-1-ium chloride (667 mg, 3.93 mmol) followed by sodium carbonate (833 mg, 7.86 mmol) and the resulting mixture was refluxed for 16 h. The mixture was partitioned between EtOAc and water and the aqueous layer was extracted with EtOAc (3×). Combined organic layer was washed with brine, dried over MgSO₄ and filtered. Concentration of filtrate gave dark solid which was purified by silica gel column chromatography using (0-100)% EtOAc/Hexanes as solvent system to give the title product. LC/MS: [M+H]⁺=325.3

Step B: 4-(4,5,6,7-tetrahydro-2H-pyrazolo[4,3-c]pyridin-2-yl)benzonitrile tert-butyl 2-(4-cyanophenyl)-6,7-dihydro-2H-pyrazolo[4,3-c]pyridine-5(4H)-carboxylate (78 mg, 0.240 mmol) was dissolved in 1.25 N HCl in MeOH (5 ml) and stirred at rt for 4 h. The reaction mixture was then concentrated to give the title product as solid. LC/MS: [M+H]⁺=225.3

Intermediate 21

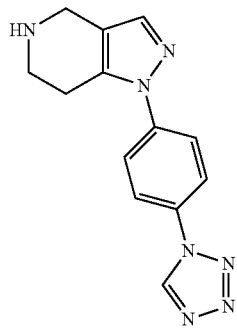 [SMILES: c1cc(-n2ncc3c2CCNC3)ccc1-n1cnnn1]

1-(4-(1H-tetrazol-yl)phenyl)-4,5,6,7-tetrahydro-1H-pyrazolo[4,3-c]pyridine

Step A: tert-butyl 1-(4-nitrophenyl)-6,7-dihydro-1H-pyrazolo[4,3-c]pyridine-5(4H)-carboxylate To a solution of (Z)-tert-butyl 3-((dimethylamino)methylene)-4-oxopiperidine-1-carboxylate (2.0 g, 7.86 mmol) in EtOH (10 ml) was added (4-nitrophenyl)hydrazine (1.204 g, 7.86 mmol) followed by sodium carbonate (1.67 g, 15.73 mmol) and refluxed for 16 h. The mixture was partitioned between EtOAc and water and the layers were separated. Aqueous layer was extracted with EtOAc (3×) and combined organic layer was washed with brine, dried over MgSO₄, filtered, concentrated and purified by silica gel column chromatography using (0-100)% EtOAc/Hexanes as mobile phase to get the title product as solid. LC/MS: [M+H]⁺=345.3

Step B: tert-butyl 1-(4-aminophenyl)-6,7-dihydro-1H-pyrazolo[4,3-c]pyridine-5(4H)-carboxylate To a solution of tert-butyl 1-(4-nitrophenyl)-6,7-dihydro-1H-pyrazolo[4,3-c]pyridine-5(4H)-carboxylate (206 mg, 0.598 mmol) in MeOH (7 ml) was added Pd/C (50 mg). The mixture was stirred in a flask equipped with a balloon filled with an atmosphere of H₂ for 16 h. The reaction mixtured was filtered through celite, then concentrated to get the title compound as solid. LC/MS: [M+H]⁺=315.3

Step C: tert-butyl 1-(4-(1H-tetrazol-1-yl)phenyl)-6,7-dihydro-1H-pyrazolo[4,3-c]pyridine-5(4H)-carboxylate To a solution of tert-butyl 1-(4-aminophenyl)-6,7-dihydro-1H-pyrazolo[4,3-c]pyridine-5(4H)-carboxylate (158 mg, 0.503 mmol) in AcOH (5 ml) was added triethyl orthoformate (0.167 ml, 1.005 mmol) followed by sodium azide (65.3 mg, 1.005 mmol). The mixture was stirred at 80° C. for 4 h. Slight brown solution was partitioned between water and EtOAc and aqueous layer was extracted with EtOAc (3×). Combined organic layer was washed with brine, dried over MgSO₄, filtered and concentrated to get the title compound as solid. LC/MS: [M+H]⁺=368.3

Step D: 1-(4-(1H-tetrazol-1-yl)phenyl)-4,5,6,7-tetrahydro-1H-pyrazolo[4,3-c]pyridine To a solution of tert-butyl 1-(4-(1H-tetrazol-1-yl)phenyl)-6,7-dihydro-1H-pyrazolo[4,3-c]pyridine-5(4H)-carboxylate (159 mg, 0.433 mmol) in MeOH (4 ml) was added 4 M HCl solution in 1,4-dioxane (4 ml) and was stirred at rt for 4 h. The reaction mixture was concentrated to get the title product as solid. LC/MS: [M+H]⁺=268.3

Intermediate 22

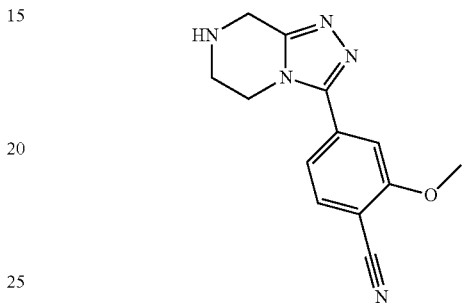

2-methoxy-4-(5,6,7,8-tetrahydro-[1,2,4]triazolo[4,3-a]pyrazin-3-yl)benzonitrile

Step A: tert-butyl 2-(4-bromo-3-methoxybenzoyl)hydrazinecarboxylate

To a mixture of 4-bromo-3-methoxybenzoic acid (1 g, 4.33 mmol), ((1H-benzo[d][1,2,3]triazol-1-yl)oxy)tri(pyrrolidin-1-yl)phosphonium hexafluorophosphate(V) (2.478 g, 4.76 mmol) and N-ethyl-N-isopropylpropan-2-amine (0.91 ml, 5.19 mmol) in DMF (10 ml) was added tert-butyl hydrazinecarboxylate (0.572 g, 4.33 mmol) at rt and stirred for 18 h. After concentration, the residue was partitioned between EtOAc and NaHCO₃ (sat'd) and aqueous layer was extracted with EtOAc (2×). Combined organic phase was washed with brine, dried over MgSO₄, filtered, concentrated and purified by biotage eluting with (0-100)% EtOAc/hexanes to give the title product as white solid. LC/MS: [M+Na]⁺=368.8

Step B: 4-bromo-3-methoxybenzohydrazide hydrochloride

To a solution of tert-butyl 2-(4-bromo-3-methoxybenzoyl)hydrazinecarboxylate (1.07 g, 3.10 mmol) in MeOH (5 ml) was added 4 N—HCl in 1,4-dioxane (10 ml) at rt and the resulting mixture was stirred at rt for 18 h. After concentration the residue was partitioned between EtOAc and NaHCO₃ (sat'd) and the aqueous layer was extracted with EtOAc (2×). Combined organic phase was washed with brine, dried over MgSO₄, filtered and concentrated to give the title compound as solid. LC/MS: [M+H]⁺=246.9

Step C: tert-butyl 3-(4-bromo-3-methoxyphenyl)-5,6-dihydro-[1,2,4]triazolo[4,3-a]pyrazine-7(8H)-carboxylate To a solution of tert-butyl 3-ethoxy-5,6-dihydropyrazine-1 (2H)-carboxylate (705 mg, 3.09 mmol) and 4-bromo- 3-methoxybenzohydrazide hydrochloride (870 mg, 3.09 mmol) in 2-propanol (10 ml) was added N-ethyl-N-isopropylpropan-2-amine (0.54 ml, 3.09 mmol) at rt and the resulting mixture was refluxed for 18 h. After concentration the residue was partitioned between EtOAc and aq NaHCO$_3$ (sat'd) and aqueous layer was extracted with EtOAc (3×). Combined organic layer was washed with brine, dried over MgSO$_4$, filtered, concentrated and purified by biotage (0-10)% MeOH/DCM to give the title compound as solid. LC/MS: [M+H]$^+$=409.2

Step D: tert-butyl 3-(4-cyano-3-methoxyphenyl)-5,6-dihydro-[1,2,4]triazolo[4,3-a]pyrazine-7(8H)-carboxylate To a solution of tert-butyl 3-(4-bromo-3-methoxyphenyl)-5,6-dihydro-[1,2,4]triazolo[4,3-a]pyrazine-7(8H)-carboxylate (580 mg, 1.417 mmol) in DMF (4 ml) were added Zinc cyanide (0.45 ml, 7.09 mmol), Pd$_2$dba$_3$ (130 mg, 0.142 mmol) and DPPF (79 mg, 0.142 mmol) sequentially and microwaved at 100° C. for 1 h. The mixture was partitioned between EtOAc and aq NaHCO$_3$ (sat'd) and aqueous layer was extracted with EtOAc (3×). Combined organic layer was washed with brine, dried over MgSO$_4$, filtered, concentrated and purified by silica gel column chromatography using (0-10)% MeOH/DCM as solvent system and the title product was isolated as solid. LC/MS: [M+H]$^+$=356.3

Step E: 2-methoxy-4-(5,6,7,8-tetrahydro-[1,2,4]triazolo[4,3-a]pyrazin-3-yl)benzonitrile To a solution of tert-butyl 3-(4-cyano-3-methoxyphenyl)-5,6-dihydro-[1,2,4]triazolo[4,3-a]pyrazine-7(8H)-carboxylate (170 mg, 0.478 mmol) in MeOH (4 ml) was added 4 M HCl solution in 1,4-dioxane (4 ml) and was stirred at rt for 4 h. The reaction mixture was concentrated to get the title product as solid. LC/MS: [M+H]$^+$=256.3

Intermediate 23

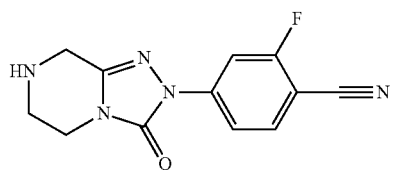 [SMILES: N#Cc1ccc(-n2nc3n(c2=O)CCNC3)cc1F]

2-fluoro-4-(3-oxo-5,6,7,8-tetrahydro-[1,2,4]triazolo[4,3-a]pyrazin-2(3H)-yl)benzonitrile Step A: tert-butyl 3-(2-(4-cyano-3-fluorophenyl)hydrazinyl)-5,6-dihydropyrazine-1(2H)-carboxylate To a solution of tert-butyl 3-ethoxy-5,6-dihydropyrazine-1(2H)-carboxylate (500 mg, 3.31 mmol) in DLC/MSO (16 ml) was added 2-fluoro-4-hydrazinylbenzonitrile (755 mg, 3.31 mmol) at rt and the resulting mixture was stirred at 100° C. for 18 h. The reaction mixture was partitioned between EtOAc and aqueous NaHCO$_3$ (saturated) and the aqueous layer was extracted with EtOAc (2×). The combined organic phase was washed with brine, dried over anhydrous MgSO4, and filtered. Concentration of the filtrate gave the title product as brown viscous oil which was used in the next step without further purification. LC/MS: [M+H]$^+$=334.3

Step B: 2-fluoro-4-(3-oxo-5,6,7,8-tetrahydro-[1,2,4]triazolo[4,3-a]pyrazin-2(3H)-yl)benzonitrile To tert-butyl 3-(2-(4-cyano-3-fluorophenyl)hydrazinyl)-5,6-dihydropyrazine-1(2H)-carboxylate (532 mg, 1.596 mmol) in THF (7979 µl) was added CDI (285 mg, 1.755 mmol) at rt and the mixture was refluxed 16 h. The mixture was partitioned between EtOAc and NaHCO$_3$ (saturated) and the aqueous layer was extracted with EtOAc (2×). The combined organic phase was washed with brine, dried over anhydrous MgSO$_4$ and filtered. Concentration of the filtrate was followed by purification using a Biotage system using (0-60)% EtOAc/Hexanes as solvent system to give the title compound as yellow solid.

The boc intermediate was then dissolved in 4 M HCl in 1,4-dioxane (20 ml), few drops of MeOH were added for solubility. The solution was stirred at rt 16 h. The reaction was then concentrated to give the title compound as yellow powder. LC/MS: [M+H]$^+$=260.1

Intermediate 24

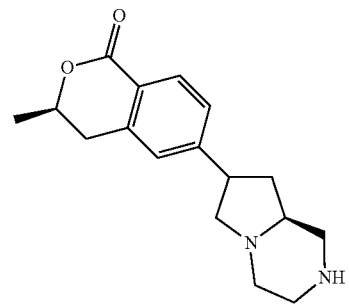 [SMILES: C[C@@H]1Cc2cc(C3C[C@H]4CNCCN4C3)ccc2C(=O)O1]

(3R)-3-methyl-6-((8aS)-octahydropyrrolo[1,2-a]pyrazin-7-yl)isochroman-1-one

Step A: (2S,4R)-1-(tert-butoxycarbonyl)-4-hydroxypyrrolidine-2-carboxylic acid

To the solution of L-hydroxyproline (12.41 g, 95 mmol) in dioxane (150 mL) and NaOH (189 ml, 189 mmol) at 0° C. was added di-tert-butyl dicarbonate (23.07 ml, 99 mmol) in dioxane (20 mL) dropwise. The resulting mixture was stirred at 0° C. for 30 min and warmed to rt for 2 h. After removing the volatiles, the alkaline phase was extracted with diethyl ether before was neutralized to pH 4. The aqueous was extracted with 30% IPA/Chloroform six times. The combined 30% IPA/chloroform phase was dried over Na$_2$SO$_4$, concentrated to give (2S,4R)-1-(tert-butoxycarbonyl)-4-hydroxypyrrolidine-2-carboxylic acid. LC/MS: [M+Na]$^+$=254.14.

Step B: (2S,4R)-tert-butyl 2-(benzyl(2-ethoxy-2-oxoethyl)carbamoyl)-4-hydroxypyrrolidine-1-carboxylate To the solution of (2S,4R)-1-(tert-butoxycarbonyl)-4-hydroxypyrrolidine-2-carboxylic acid (11 g, 47.6 mmol) and N-benzylglycine ethyl ester (10.11 g, 52.3 mmol) in DCM (300 mL) was added EDC (11.85 g, 61.8 mmol) and HOBT (0.728 g, 4.76 mmol), and TEA (13.26 ml, 95 mmol). The resulting solution was stirred at rt for 3 h. The solution was partitioned between DCM and water. The water phase was extracted with DCM. The combined DCM phase was dried Na$_2$SO$_4$, concentrated and the residue was purified on Biotage using EtOAc/hexane as eluting solvents to give (2S,4R)-tert-butyl 2-(benzyl(2-ethoxy-2-oxoethyl)carbamoyl)-4-hydroxypyrrolidine-1-carboxylate. LC/MS: [M+Na]$^+$=429.0.

Step C: (7R,8aS)-2-benzyl-7-hydroxyhexahydropyrrolo[1,2-a]pyrazine-1,4-dione

To the solution of (2S,4R)-tert-butyl 2-(benzyl(2-ethoxy-2-oxoethyl)carbamoyl)-4-hydroxypyrrolidine-1-carboxylate (12.6 g, 31.0 mmol) in DCM (30 mL) was added TFA (23.88 ml, 310 mmol) and the resulting solution was stirred at rt for 2 h. After removing the volatile, the residue was dissolved in THF (200 mL) and treated with sat. NaHCO$_3$ until pH=8. The resulting mixture was stirred at rt for 1 h. The mixture was extracted with EtOAc, dried over Na$_2$SO$_4$, concentrated to give (7R,8aS)-2-benzyl-7-hydroxyhexahydropyrrolo[1,2-a]pyrazine-1,4-dione LC/MS: [M+H]$^+$=261.1.

Step D: (7R,8aS)-2-benzyloctahydropyrrolo[1,2-a]pyrazin-7-ol

To the solution of (7R,8aS)-2-benzyl-7-hydroxyhexahydropyrrolo[1,2-a]pyrazine-1,4-dione (7 g, 26.9 mmol) in THF (200 mL) was added LiAlH$_4$ (4.08 g, 108 mmol) by portions slowly under N$_2$. The resulting mixture was heated at reflux for 3 h. The reaction was quenched by addition of water dropwise at 0° C. followed by 5 N NaOH (10 mL). The slurry was stirred at 0° C. until white solid appeared. The mixture was filtered and washed with excess of DCM. The combined the mixture was dried over Na$_2$SO$_4$, concentrated to give (7R,8aS)-2-benzyloctahydropyrrolo[1,2-a]pyrazin-7-ol. LC/MS: [M+H]$^+$=233.2.

Step E: (7R,8aS)-octahydropyrrolo[1,2-a]pyrazin-7-ol

To the solution of (7R,8aS)-2-benzyloctahydropyrrolo[1,2-a]pyrazin-7-ol (6.25 g, 26.9 mmol) in AcOH (30 mL) was added palladium hydroxide on carbon (1.889 g, 2.69 mmol) and the resulting mixture was subjected to hydrogenation at 40 Psi for 22 h. After filtration through celite under N$_2$, the filtrate was concentrated to give (7R,8aS)-octahydropyrrolo[1,2-a]pyrazin-7-ol. LC/MS: [M+H]$^+$=143.2.

Step F: (7R,8aS)-tert-butyl 7-hydroxyhexahydropyrrolo[1,2-a]pyrazine-2(1H)-carboxylate To the solution of (7R,8aS)-octahydropyrrolo[1,2-a]pyrazin-7-ol (3.83 g, 26.9 mmol) in dioxane (100 mL) was added NaOH (269 ml, 269 mmol) and BOC$_2$O (6.25 ml, 26.9 mmol) in dioxane (10 mL) dropwise. The resulting solution was stirred at rt 16 h. After removing the volatile, the alkaline phase was extracted with 30% IPA/Chloroform (6×160 mL). The combined organic phase was dried over Na$_2$SO$_4$, concentrated and the residue was purified on Biotage using MeOH/DCM as eluting solvents to give over 10-10CV to give (7R,8aS)-tert-butyl 7-hydroxyhexahydropyrrolo[1,2-a]pyrazine-2(1H)-carboxylate LC/MS: [M−56+1]+=143.3; [M−100+1]$^+$=187.3

Step G: (S)-tert-butyl 7-oxohexahydropyrrolo[1,2-a]pyrazine-2(1H)-carboxylate

To the solution of oxalyl chloride (8.20 ml, 16.41 mmol) in CH$_2$Cl$_2$ (25 ml) at −78° C. was added DLC/MSO (1.830 ml, 25.8 mmol) dropwise, the resulting solution was stirred at −78° C. for 10 min before (7R,8aS)-tert-butyl 7-hydroxyhexahydropyrrolo[1,2-a]pyrazine-2(1H)-carboxylate (2.84 g, 11.72 mmol) in DCM (20 mL) was added dropwise −78° C. The resulting solution was stirred at −78° C. for 5 min before TEA (8.17 ml, 58.6 mmol) was added dropwise. The resulting solution was stirred at −78° C. for additional 1 h before warmed to 0° C. for 30 min. The reaction was quenched by water, extracted with DCM three times (3×100 mL). The combined DCM phase was dried over Na$_2$SO$_4$, concentrated and the resulting residue was purified on Biotage using EtOAc/hexane to give (S)-tert-butyl 7-oxohexahydropyrrolo[1,2-a]pyrazine-2(1H)-carboxylate. LC/MS: [M−56+1]$^+$=141.22; [M−100+1]$^+$=185.21.

Step H: (S)-tert-butyl 7-(((trifluoromethyl)sulfonyl)oxy)-3,4,8,8a-tetrahydropyrrolo[1,2-a]pyrazine-2(1H)-carboxylate To the solution of (S)-tert-butyl 7-oxohexahydropyrrolo[1,2-a]pyrazine-2(1H)-carboxylate (0.78 g, 3.25 mmol) in THF (10 ml) was added potassium hexamethyldisilazide (3.90 ml, 3.90 mmol) at −78° C. dropwise. The resulting solution was aged at −78° C. for 2 h before addition of N-phenylbis(trifluoromethanesulfonimide) (1.392 g, 3.90 mmol) in THF (2 mL) dropwise. The resulting solution was stirred at −78° C. for 2 h before warming up to 0° C. for 2 h. The reaction was quenched by addition of water, the solution was diluted in EtOAc, washed with NaHCO$_3$ solution, dried over Na$_2$SO$_4$, concentrated and the residue was purified on Biotage (40+S, pre-basified by Et$_3$N/DCM) using EtOAc/hexane as eluting solvents to give (S)-tert-butyl 7-(((trifluoromethyl)sulfonyl)oxy)-3,4,8,8a-tetrahydropyrrolo[1,2-a]pyrazine-2(1H)-carboxylate. LC/MS: [M−56+1]+=317.0; [M−100+1]−273.0.

Step H: (S)-tert-butyl 7-((R)-3-methyl-1-oxoisochroman-6-yl)-3,4,8,8a-tetrahydropyrrolo[1,2-a]pyrazine-2(1H)-carboxylate The mixture of (S)-tert-butyl 7-(((trifluoromethyl)sulfonyl)oxy)-3,4,8,8a-tetrahydropyrrolo[1,2-a]pyrazine-2(1H)-carboxylate (201 mg, 0.698 mmol), (R)-3-methyl-6-(4,4,5,5-tetramethyl-1,3,2-dioxaborolan-2-yl)isochroman-1-one (200 mg, 0.537 mmol), sodium carbonate (1.611 ml, 1.611 mmol), and Tetrakis(triphenylphosphine)palladium (62.1 mg, 0.054 mmol) in dioxane (2 ml) was flushed with N$_2$ and then heated at 150° C. at microwave for 30 min. The mixture was filtered through celite, washed with MeOH, the filtrate was concentrated and the residue was partitioned between DCM and water. The pH of aqueous phase was adjusted by 1 N HCl to 3-4. After removing the volatile, the aqueous phase was frozen and lyophized. To the lyophized solid mixture was added DIEA (0.281 ml, 1.611 mmol), EDC (154 mg, 0.806 mmol) and DMAP (3.28 mg, 0.027 mmol) in CH$_2$Cl$_2$ (40 ml) and the resulting mixture was stirred at rt for 4 h. Additional DIEA (0.281 ml, 1.611 mmol), EDC (154 mg, 0.806 mmol), and DMAP (3.28 mg, 0.027 mmol) was added and the resulting mixture was stirred at rt 16 h. The organic phase was washed with sat. NaHCO$_3$, the aqueous phase was extracted with DCM. The combined DCM phase was dried over Na$_2$SO$_4$, concentrated and the residue was purified on Biotage using EtOAc/hexane as eluting solvents to give (S)-tert-butyl 7-((R)-3-methyl-1-oxoisochroman-6-yl)-3,4,8,8a-tetrahydropyrrolo[1,2-a]pyrazine-2(1H)-carboxylate. LC/MS: [M+1]$^+$=385.1.

Step I: (8aS)-tert-butyl 7-((R)-3-methyl-1-oxoisochroman-6-yl)hexahydropyrrolo[1,2-a]pyrazine-2 (1H)-carboxylate To the solution of (S)-tert-butyl 7-((R)-3-methyl-1-oxoisochroman-6-yl)-3,4,8,8a-tetrahydropyrrolo[1,2-a]pyrazine-2(1H)-carboxylate (62 mg, 0.161 mmol) in MeOH (10 ml) was added 10% Pd/C (34.3 mg, 0.032 mmol) and the resulting mixture was subjected to hydrogenation via balloon at rt for 2 h. After filtration through celite under N$_2$, the filtrate was concentrated to give (8aS)-tert-butyl 7-((R)-3-methyl-1-oxoisochroman-6-yl)hexahydropyrrolo[1,2-a] pyrazine-2(1H)-carboxylate. LC/MS: [M+1]$^+$=387.1

Step J: (3R)-3-methyl-6-((8aS)-octahydropyrrolo[1,2-a]pyrazin-7-yl)isochroman-1-one To the solution of (8aS)-tert-butyl 7-((R)-3-methyl-1-oxoisochroman-6-yl)hexahydropyrrolo[1,2-a]pyrazine-2 (1H)-carboxylate (62.2 mg, 0.161 mmol) in CH$_2$Cl$_2$ (1 ml) was added TFA (1.861 ml, 24.15 mmol) at rt for 1 h. After removing the volatile, the residue was partitioned between DCM and 1 N NaOH, the alkaline phase was extracted with DCM three times, the combined DCM phase was dried over Na$_2$SO$_4$, and concentrated to give (3R)-3-methyl-6-((8aS)-octahydropyrrolo[1,2-a]pyrazin-7-yl)isochroman-1-one. LC/MS: [M+1]$^+$=287.2.

Intermediate 25

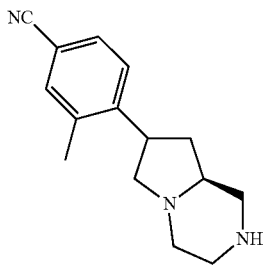 [SMILES: Cc1cc(C#N)ccc1C1C[C@H]2CNCCN2C1]

3-methyl-4-((8aS)-octahydropyrrolo[1,2-a]pyrazin-7-yl)benzonitrile

Step A: (S)-tert-butyl 7-(4-cyano-2-methylphenyl)-3,4,8,8a-tetrahydropyrrolo[1,2-a]pyrazine-2(1H)-carboxylate The solution of (S)-tert-butyl 7-((((trifluoromethyl)sulfonyl)oxy)-3,4,8,8a-tetrahydropyrrolo[1,2-a]pyrazine-2(1H)-carboxylate (227 mg, 0.610 mmol), 2-methyl-4-cyanophenylboronic acid (118 mg, 0.732 mmol), Tetrakis(triphenylphosphine)palladium (70.4 mg, 0.061 mmol) and 1N Na$_2$CO$_3$ solution (1829 μl, 1.829 mmol) in dioxane (4 mL) was heated at 140° C. at microwave for 20 min. After removing the volatile, the residue was purified on Biotage using EtOAc/hexane as eluting solvents to give over 10-10CV to give (S)-tert-butyl 7-(4-cyano-2-methylphenyl)-3,4,8,8a-tetrahydropyrrolo[1,2-a]pyrazine-2(1H)-carboxylate. LC/MS: [M+1]$^+$=340.1.

Step B: (8aS)-tert-butyl 7-(4-cyano-2-methylphenyl) hexahydropyrrolo[1,2-a]pyrazine-2(1H)-carboxylate To the solution of (S)-tert-butyl 7-(4-cyano-2-methylphenyl)-3,4,8,8a-tetrahydropyrrolo[1,2-a]pyrazine-2(1H)-carboxylate (142 mg, 0.418 mmol) in MeOH (20 mL) was added 10% Pd/C (445 mg, 0.418 mmol) and the resulting mixture was subjected to hydrogenation at rt for 1 h. After filtration through celite under N$_2$, the filtrate was concentrated and the residue was purified on TLC using EtOAc/hexane as developing solvents to give (8aS)-tert-butyl 7-(4-cyano-2-methylphenyl)hexahydropyrrolo[1,2-a]pyrazine-2 (1H)-carboxylate. LC/MS: [M+1]$^+$=342.1.

Step C: 3-methyl-4-((8aS)-octahydropyrrolo[1,2-a]pyrazin-7-yl)benzonitrile

To the solution of (8aS)-tert-butyl 7-(4-cyano-2-methylphenyl)hexahydropyrrolo[1,2-a]pyrazine-2(1H)-carboxylate (65 mg, 0.190 mmol) in DCM (1 mL) was added TFA (2 mL, 26.0 mmol) at rt for 1 h. After removing the volatile, the residue was partitioned between DCM and 1 N NaOH, the alkaline phase was extracted with DCM, 30% IPA/chloroform, the combined organic phase was dried over Na$_2$SO$_4$, and concentrated to give 3-methyl-4-((8aS)-octahydropyrrolo[1,2-a]pyrazin-7-yl)benzonitrile. LC/MS: [M+1]$^+$=242.2.

Intermediate 26

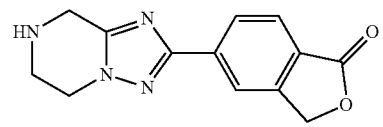 [SMILES: O=C1OCc2cc(-c3nc4n(n3)CCNC4)ccc21]

5-(5,6,7,8-tetrahydro-[1,2,4]triazolo[1,5-a]pyrazin-2-yl)isobenzofuran-1 (3H)-one Step A: tert-butyl 3-(1-oxo-1,3-dihydroisobenzofuran-5-carboxamido)-5,6-dihydropyrazine-1(2H)-carboxylate To a mixture of 1-oxo-1,3-dihydroisobenzofuran-5-carboxylic acid (894 mg, 5.02 mmol) and CDI (895 mg, 5.52 mmol) was added THF (10 ml) at rt. The mixture was refluxed for 1 h. To the above mixture was added tert-butyl 3-amino-5,6-dihydropyrazine-1(2H)-carboxylate (1.0 g, 5.02 mmol) in THF (10 ml), then refluxing was continued for additional 16 h. The mixture was partitioned between EtOAc and aq. NaHCO$_3$ (sat'd) and aqueous layer was extracted with EtOAc (3×). Combined organic layer was washed with brine, dried over MgSO$_4$, filtered. Concentration of filtrate followed by purification via silica gel column chromatography using (0-10)% MeOH/DCM gave the title compound as solid.

Step B: 2-(1-oxo-1,3-dihydroisobenzofuran-5-yl)-5,6,7,8-tetrahydro-[1,2,4]triazolo[1,5-a]pyrazin-7-ium chloride To a solution of tert-butyl 3-(1-oxo-1,3-dihydroisobenzofuran-5-carboxamido)-5,6-dihydropyrazine-1(2H)-carboxylate (596 mg, 1.658 mmol) in DCM (15 ml) was added O-(mesitylsulfonyl)hydroxylamine (357 mg, 1.658 mmol) at 0° C. After the removal of ice bath the mixture was stirred at rt for 1 h. Concentration of the reaction mixture gave a yellow solid, which was dissolved in MeOH (15 ml), DIPEA (0.32 ml, 1.824 mmol) was added to that and the resulting mixture was refluxed for 4 h. After concentration, the residue was partitioned between EtOAc and aq NaHCO₃ (sat'd) and the aqueous layer was extracted with EtOAc (3×). Combined organic phase was washed with brine, dried over MgSO₄, filtered, and purified by preparative TLC using 10% MeOH/DCM, giving the boc intermediate, tert-butyl 2-(1-oxo-1,3-dihydroisobenzofuran-5-yl)-5,6-dihydro-[1,2,4]triazolo[1,5-a]pyrazine-7(8H)-carboxylate, as solid. LC/MS: [M+H]⁺=357.0

The boc intermediate, tert-butyl 2-(1-oxo-1,3-dihydroisobenzofuran-5-yl)-5,6-dihydro-[1,2,4]triazolo[1,5-a]pyrazine-7(8H)-carboxylate, (40 mg, 0.112 mmol) was dissolved in 4N-HCl in 1,4-dioxane (5 ml) and the resulting solution was stirred at rt for 1 h. Concentration after 1 hr gave the title compound as a slightly brown solid. LC/MS: [M+H]⁺=257.0

Intermediate 27

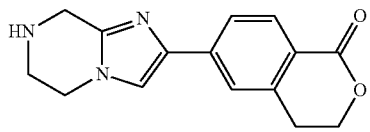 [SMILES: O=C1OCCc2cc(-c3cn4c(n3)CNCC4)ccc21]

6-(5,6,7,8-tetrahydroimidazo[1,2-a]pyrazin-2-yl)isochroman-1-one

Step A: 6-(5,6,7,8-tetrahydroimidazo[1,2-a]pyrazin-2-yl)isochroman-1-one

To a solution of 6-(2-bromoacetyl)isochroman-1-one (407 mg, 2.042 mmol) in 2-propanol (9 ml) was added tert-butyl 3-amino-5,6-dihydropyrazine-1(2H)-carboxylate (458 mg, 1.702 mmol) and the resulting mixture was microwaved for 30 mins at 100° C. The mixture was partitioned between EtOAc and aqueous NaHCO₃ (saturated) and the aqueous layer was extracted with EtOAc (2×). The combined organic phase was washed with brine, dried over anhydrous MgSO₄ and filtered. Concentration of filtrate was followed by purification by silica gel column chromatography Biotage system) using (0-100)% EtOAc/hexanes followed by (0-10)% MeOH/DCM to give the boc intermediate, tert-butyl 2-(1-oxoisochroman-6-yl)-5,6-dihydroimidazo[1,2-a]pyrazine-7(8H)-carboxylate, as an orange/tan solid. LC/MS: [M+H]⁺=370.2

The tert-butyl 2-(1-oxoisochroman-6-yl)-5,6-dihydroimidazo[1,2-a]pyrazine-7(8H)-carboxylate was dissolved in 4N HCl in 1,4-dioxane (10 ml) at rt. A few drops of MeOH was added to help with solubility. The resulting reaction mixture was stirred at rt for 2 h. The mixture was then concentrated to give 6-(5,6,7,8-tetrahydroimidazo[1,2-a]pyrazin-2-yl)isochroman-1-one as a tan/orange solid. LC/MS: [M+H]⁺=270.3

Intermediate 28

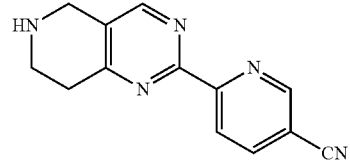 [SMILES: N#Cc1ccc(-c2ncc3c(n2)CCNC3)nc1]

6-(5,6,7,8-tetrahydropyrido[4,3-d]pyrimidin-2-yl)nicotinonitrile

Step A: tert-butyl 2-(5-bromopyridin-2-yl)-7,8-dihydropyrido[4,3-d]pyrimidine-6(5H)-carboxylate Na (580 mg, 25.2 mmol) was dissolved in EtOH (30 ml) under Ar, and then 5-bromopicolinimidamide (2.98 g, 12.6 mmol) was added and the mixture was stirred at rt for 5 minutes. (E)-tert-butyl 3-((dimethylamino)methylene)-4-oxopiperidine-1-carboxylate (3.84 g, 15.1 mmol) was added to the mixture at one portion and the resulting mixture was refluxed under Ar for 4 h. After cooled to rt, the mixture was concentrated and the residue was purified by silica gel column chromatography to give the title compound as yellow solid.

Step B: tert-butyl 2-(5-cyanopyridin-2-yl)-7,8-dihydropyrido[4,3-d]pyrimidine-6(5H)-carboxylate To a solution of tert-butyl 2-(5-bromopyridin-2-yl)-7,8-dihydropyrido[4,3-d]pyrimidine-6(5H)-carboxylate (500 mg, 1.28 mmol), ZnCN₂ (150 mg, 1.28 mmol), TMEDA (58 mg, 0.5 mmol), xantphos (14.5 mg, 0.03 mmol) in DMF (3 ml) was added Pd₂(dba)₃ (12 mg, 0.02 mmol), then the reaction was heated under microwave condition at 120° C. for 20 minutes. After cooling to rt, the mixture was poured into water (20 ml) and extracted with EtOAc (3×). The combined organic layers were washed with water, brine, dried and concentrated. The residue was purified by silica gel column chromatography to give the title compound as yellow solid.

Step C: 6-(5,6,7,8-tetrahydropyrido[4,3-d]pyrimidin-2-yl)nicotinonitrile

To a solution of tert-butyl 2-(5-cyanopyridin-2-yl)-7,8-dihydropyrido[4,3-d]pyrimidine-6(5H)-carboxylate (150 mg, 0.45 mmol) in DCM (5 ml) was added TFA (1 ml) at one portion and the reaction was stirred at rt for 1 hour. Reaction mixture was concentrated to get the title compound which was taken to the next step without purification.

Intermediate 29

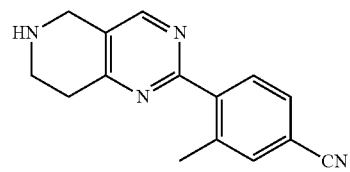 [SMILES: Cc1cc(C#N)ccc1-c1ncc2c(n1)CCNC2]

3-methyl-4-(5,6,7,8-tetrahydropyrido[4,3-d]pyrimidin-2-yl)benzonitrile

Step A: 4-bromo-2-methylbenzimidamide

To a solution of NH₄Cl (10 mmol) in dry toluene (10) was added AlMe₃ (5 mL, 10 mmol) dropwise under Ar at 0° C., and the solution was stirred at rt for 2 h. This was followed by the addition of 4-bromo-2-methylbenzonitrile (5 mmol) and the mixture was stirred at 60° C. 16 h. After cooling to 0° C., MeOH (10 ml) was added and the mixture was stirred at rt for 1 hour. The mixture was filtered, and the solid was washed with MeOH (50 ml). The filtrate was concentrated and the solid residue was washed with ether to give the title compound which was used for the next step without purification.

Step B: tert-butyl 2-(4-bromo-2-methylphenyl)-7,8-dihydropyrido[4,3-d]pyrimidine-6(5H)-carboxylate Na (250 mg, 10.2 mmol) was dissolved in EtOH (20 ml) under Ar and 4-bromo-2-methylbenzimidamide (5.1 mmol) was added to the mixture and stirred at rt for 5 minutes. This was followed by the addition of (E)-tert-butyl 3-((dimethylamino)methylene)-4-oxopiperidine-1-carboxylate (6.1 mmol) in one portion and the resulting mixture was refluxed under Argon for 4 h. After cooling to rt, the mixture was concentrated, and the residue was purified by silica gel column chromatography to give the title compound as yellow solid.

Step C: tert-butyl 2-(4-cyano-2-methylphenyl)-7,8-dihydropyrido[4,3-d]pyrimidine-6(5H)-carboxylate To a solution of tert-butyl 2-(4-bromo-2-methylphenyl)-7,8-dihydropyrido[4,3-d]pyrimidine-6(5H)-carboxylate (1.28 mmol), Zn(CN)₂ (150 mg, 1.28 mmol), TMEDA (58 mg, 0.5 mmol), xantphos (14.5 mg, 0.03 mmol) in DMF (3 ml) was added Pd₂(dba)₃ (12 mg, 0.02 mmol) and the resulting reaction mixture was heated under microwave condition at 120° C. for 20 minutes. After cooling to rt, the mixture was poured into water (20 ml) and extracted with EtOAc (×3). The combined organic layers were washed with water, brine, dried and concentrated. The residue was purified by silica gel column chromatography to give the title compound as yellow solid.

Step D: 3-methyl-4-(5,6,7,8-tetrahydropyrido[4,3-d]pyrimidin-2-yl)benzonitrile

To a solution of tert-butyl 2-(4-cyano-2-methylphenyl)-7,8-dihydropyrido[4,3-d]pyrimidine-6(5H)-carboxylate (0.45 mmol) in DCM (5 ml) was added TFA (1 ml) in one portion and the resulting mixture reaction was stirred at rt for 1 hour then concentrated to get the title product which was used directly to the next step.

Intermediate 30

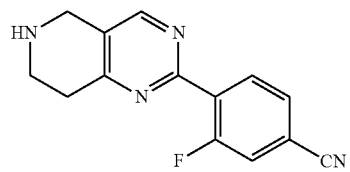 [SMILES: N#Cc1ccc(-c2ncc3c(n2)CCNC3)c(F)c1]

3-fluoro-4-(5,6,7,8-tetrahydropyrido[4,3-d]pyrimidin-2-yl)benzonitrile

The title compound was prepared in an analogous fashion to that described for 3-methyl-4-(5,6,7,8-tetrahydropyrido[4,3-d]pyrimidin-2-yl)benzonitrile, except in Step A, where 4-bromo-2-fluorobenzonitrile was used in the place of 4-bromo-2-methylbenzonitrile.

Intermediate 31

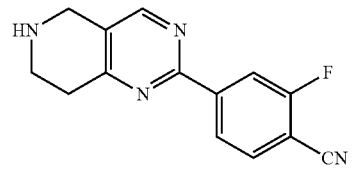 [SMILES: N#Cc1ccc(-c2ncc3c(n2)CCNC3)cc1F]

2-fluoro-4-(5,6,7,8-tetrahydropyrido[4,3-d]pyrimidin-2-yl)benzonitrile

The title compound was prepared in an analogous fashion to that described for 3-methyl-4-(5,6,7,8-tetrahydropyrido[4,3-d]pyrimidin-2-yl)benzonitrile, except in Step A, where 4-bromo-3-fluorobenzonitrile was used in place of 4-bromo-2-methylbenzonitrile.

Intermediate 32

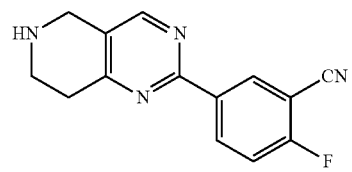 [SMILES: N#Cc1cc(-c2ncc3c(n2)CCNC3)ccc1F]

2-fluoro-5-(5,6,7,8-tetrahydropyrido[4,3-d]pyrimidin-2-yl)benzonitrile

The title compound was prepared in an analogous fashion to that described for 3-methyl-4-(5,6,7,8-tetrahydropyrido[4,3-d]pyrimidin-2-yl)benzonitrile, except in Step A, where 3-bromo-4-fluorobenzonitrile was used in the place 4-bromo-2-methylbenzonitrile.

Intermediate 33

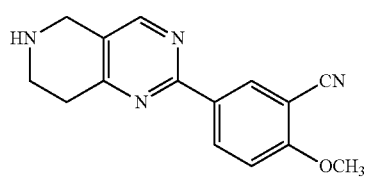 [SMILES: COc1ccc(-c2ncc3c(n2)CCNC3)cc1C#N]

2-methoxy-5-(5,6,7,8-tetrahydropyrido[4,3-d]pyrimidin-2-yl)benzonitrile

The title compound was prepared in an analogous fashion to that described for 3-methyl-4-(5,6,7,8-tetrahydropyrido[4,3-d]pyrimidin-2-yl)benzonitrile, except in Step A, 3-bromo-4-methoxybenzonitrile was used in the place of 4-bromo-2-methylbenzonitrile Intermediate 34

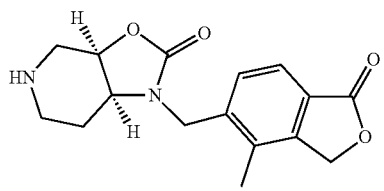 [SMILES: Cc1c(CN2C(=O)O[C@@H]3CNCC[C@@H]32)ccc2c1COC2=O]

(3aR,7aS)-1-((4-methyl-1-oxo-1,3-dihydroisobenzofuran-5-yl)methyl)hexahydrooxazolo[5,4-c]pyridin-2(1H)-one Step A: 1-benzyl-4,4-dimethoxypiperidin-3-ol A solution of $I_2$ (44.3 g, 174.4 mmol) in methanol (300 ml) was added dropwise at 0° C. to the mixture of 1-benzylpiperidin-4-one (30.0 g, 158.5 mmol) and KOH (21.3 mmol, 380.4 mmol) in methanol (300 ml). The resulting mixture was warmed to rt and stirred for 18 h. After concentration, the residue was partitioned between water and DCM. The DCM layer was dried over anhydrous $Na_2SO_4$, filtered and concentrated. The residue was refluxed in hexane (300 ml) and the insoluble solid was filtered off. The clear filtrate was stood for 16 h. The resulting precipitate was collected by filtration to afford the title compound as an orange solid. $^1$H-NMR (400 MHz, $CDCl_3$) δ ppm 7.21-7.27 (m, 5H), 3.71 (s, 1H), 3.53 (s, 2H), 3.21 (s, 3H), 3.19 (s, 3H), 2.81 (d, J=2.4 Hz, 1H), 2.62 (d, J=2.4 Hz, 1H), 2.45 (d, J=2.0 Hz, 1H), 2.04-2.11 (m, 1 h), 1.79-1.84 (m, 2H).

Step B: 1-benzyl-3-hydroxypiperidin-4-one

A mixture of 1-benzyl-4,4-dimethoxypiperidin-3-ol (4 g, 15.936 mmol) and 3 N HCl (20 mL) in EtOH (20 mL) was stirred at room temperature 16 h. The mixture was then poured slowly into aqueous $Na_2CO_3$ (saturated), and extracted with ethyl acetate (3×). The combined organic layer was washed with water and brine, dried and concentrated to obtain the title compound. $^1$H-NMR (400 MHz, $CDCl_3$) δ ppm 7.29-7.34 (m, 5H), 4.28-4.32 (m, 1H), 3.66 (s, 2H), 3.43-3.48 (m, 1H), 3.14-3.19 (m, 1H), 2.67-2.75 (m, 1H), 2.33-2.49 (m, 2H), 2.14 (t, J=10.6 Hz, 1H).

Step C: tert-butyl 3-hydroxy-4-oxopiperidine-1-carboxylate

A mixture of 1-benzyl-3-hydroxypiperidin-4-one (9.5 g, 46.341 mmol) and $Boc_2O$ (11.1 g, 50.975 mmol) in MeOH (100 mL) was heated at 50° C. under $H_2$ (50 psi) for 24 h. After filtration, the filtrate was concentrated to obtain the title compound.

Step D: (Z)-tert-butyl 4-((benzyloxy)imino)-3-hydroxypiperidine-1-carboxylate

To a mixture of $PhCH_2ONH_2$·HCl (3.3 g, 20.466 mmol) in pyridine (50 mL) was added tert-butyl 3-hydroxy-4-oxopiperidine-1-carboxylate (4 g, 18.605 mmol) at 0° C. The resulting mixture was stirred at rt 16 h, and then concentrated. The residue was purified by silica gel column chromatography to give the title compound.

Step E: (3S,4R)-tert-butyl 4-amino-3-hydroxypiperidine-1-carboxylate

A mixture of (Z)-tert-butyl 4-((benzyloxy)imino)-3-hydroxypiperidine-1-carboxylate (3 g, 9.375 mmol) and Raney Ni (1 g) in a solution of $NH_3$ in MeOH (50 mL) was stirred at rt under $H_2$ (2 MPa) for 12 h, then filtered and concentrated to obtain the title compound.

Step F: (3R,4S)-tert-butyl 3-hydroxy-4-(((4-methyl-1-oxo-1,3-dihydroisobenzofuran-5-yl)methyl)amino)piperidine-1-carboxylate To a mixture of (3S,4R)-tert-butyl 4-amino-3-hydroxypiperidine-1-carboxylate (2.5 g, 11.574 mmol) and 4-methyl-1-oxo-1,3-dihydroisobenzofuran-5-carbaldehyde (2 g, 11.364 mmol) in DCM (50 mL) was added $NaBH(OAc)_3$ (2.5 g, 11.792 mmol) at 0° C. The resulting mixture was stirred at rt 16 h, and then concentrated. The residue was dissolved in ethyl acetate, washed with water and brine, dried and concentrated. The crude product was purified by silica gel column chromatography to give the title compound.

Step G: (3aR,7aS)-tert-butyl 1-((4-methyl-1-oxo-1,3-dihydroisobenzofuran-5-yl)methyl)-2-oxohexahydrooxazolo[5,4-c]pyridine-5(2H)-carboxylate A mixture of (3R,4S)-tert-butyl 3-hydroxy-4-(((4-methyl-1-oxo-1,3-dihydroisobenzofuran-5-yl)methyl)amino)piperidine-1-carboxylate (350 mg, 0.931 mmol) and CDI (200 mg, 1.235 mmol) in THF (50 mL) was heated to reflux 16 h. The reaction mixture was concentrated and the residue was purified by preparative TLC to obtain the title compound.

Step H: (3aR,7aS)-1-((4-methyl-1-oxo-1,3-dihydroisobenzofuran-5-yl)methyl)hexahydrooxazolo[5,4-c]pyridin-2(1H)-one A mixture of (3aR,7aS)-tert-butyl 1-((4-methyl-1-oxo-1,3-dihydroisobenzofuran-5-yl)methyl)-2-oxohexahydrooxazolo[5,4-c]pyridine-5(2H)-carboxylate (80 mg, 0.199 mmol) and TFA (10 mL) in DCM (50 mL) was stirred at rt for 3 h and then concentrated to obtain the title compound.

Intermediate 35

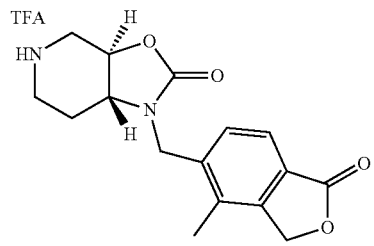 [SMILES: Cc1c(CN2C(=O)O[C@@H]3CNCC[C@H]32)ccc2c1COC2=O]

(3aR,7aR)-1-((4-methyl-1-oxo-1,3-dihydroisobenzofuran-5-yl)methyl)hexahydrooxazolo[5,4-c]pyridin-2(1H)-one

Step A: tert-butyl 7-oxa-3-azabicyclo[4.1.0]heptane-3-carboxylate

To a solution of tert-butyl 5,6-dihydropyridine-1(2H)-carboxylate (900 mg, 4.918 mmol) in DCM (150 ml) was added mCPBA (2.0 g, 9.836 mmol) slowly, in portions, at 0° C. The resulting mixture was warmed to rt and was stirred 16 h. The solution was washed with aqueous $Na_2SO_3$ until a KI test strip did not change colour. The organic layer was washed with brine and then concentrated. The residue was purified via preparative TLC to give the title compound. $^1$H-NMR (400 MHz, $CDCl_3$) δ ppm 3.82~3.93 (m, 1H), 3.43~3.69 (m, 2H), 3.10~3.28 (m, 3H), 1.87~2.04 (m, 2H), 1.45 (s, 9H).

Step B: (3R,4R)-tert-butyl 3-hydroxy-4-(((4-methyl-1-oxo-1,3-dihydroisobenzofuran-5-yl)methyl)amino)piperidine-1-carboxylate A mixture of tert-butyl 7-oxa-3-azabicyclo[4.1.0]heptane-3-carboxylate (570 mg, 2.864 mmol) and 5-(aminomethyl)-4-methylisobenzofuran-1(3H)-one (760 mg, 4.296 mmol) in EtOH (5 mL) was heated under microwave condition at 140° C. for 90 min. After cooling to rt, the resulting mixture was concentrated to dryness. The residue was purified by preparative TLC to give the title compound.

Step C: (3aR,7aR)-tert-butyl 1-((4-methyl-1-oxo-1,3-dihydroisobenzofuran-5-yl)methyl)-2-oxohexahydrooxazolo[5,4-c]pyridine-5(2H)-carboxylate A mixture of (3R,4R)-tert-butyl 3-hydroxy-4-(((4-methyl-1-oxo-1,3-dihydroisobenzofuran-5-yl)methyl)amino)piperidine-1-carboxylate (280 mg, 0.745 mmol) and CDI (145 mg, 0.894 mmol) in THF (50 mL) was heated to reflux 16 h, and then concentrated. The residue was purified by preparative TLC to obtain the title compound.

Step D: (3aR,7aR)-1-((4-methyl-1-oxo-1,3-dihydroisobenzofuran-5-yl)methyl) hexahydrooxazolo[5,4-c]pyridin-2(1H)-one A mixture of (3aR,7aR)-tert-butyl 1-((4-methyl-1-oxo-1,3-dihydroisobenzofuran-5-yl)methyl)-2-oxohexahydrooxazolo[5,4-c]pyridine-5 (2H)-carboxylate (40 mg, 0.100 mmol) and TFA (10 mL) in DCM (20 mL) was stirred at rt for 3 h and then concentrated to obtain the title compound.

Intermediate 36

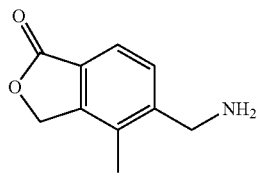

5-(aminomethyl)-4-methylisobenzofuran-1(3H)-one

Step A: 4-methyl-1-oxo-1,3-dihydroisobenzofuran-5-carbonitrile

To a solution of 5-bromo-4-methylisobenzofuran-1(3H)-one (1.01 g, 4.4 mol) in DMF (20 ml) was added $Zn(CN)_2$ (0.52 g, 4.4 mol) and $Pd(PPh_3)_4$ (0.5 g, 0.4 mmol) at one portion and the reaction was charged with Ar and heated to 100° C. for 10 h. The reaction was poured into EtOAc and filtered through a kieselguhr pad. The filtrate was washed with water, brine, dried and concentrated to a brown solid, which was purified by silica gel column chromatography to give the title compound as a white solid.

Step B: 5-(aminomethyl)-4-methylisobenzofuran-1(3H)-one

To a solution of 4-methyl-1-oxo-1,3-dihydroisobenzofuran-5-carbonitrile (0.72 g, 4.15 mmol) in AcOH (2 ml) was added Pd/C (100 mg) under Ar and the mixture was stirred at ambient temperature under $H_2$ atmosphere for 16 h. The reaction mixture was filtered and the filtrate was concentrated to give the title compound.

Intermediate 37

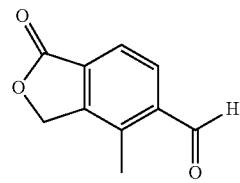

4-methyl-1-oxo-1,3-dihydroisobenzofuran-5-carbaldehyde

Step A: 4-Bromo-3-hydroxymethyl-2-methyl phenol

3-Hydroxymethyl-2-methyl phenol (113.9 g, 824.0 mmol) was dissolved in a mixture of acetonitrile (850 mL) and rifluoroacetic acid (750.0 mL, 9,735 mmol) in a 3-neck 5-L flask under nitrogen. The reaction mixture was cooled to −33° C. N-bromosuccinirolde (141 gs 791 mmol) was added over 15 minutes, with the temperature during addition in the range of −35 to −33° C. The reaction mixture was allowed to stir for an additional 15 min during which time the temperature decreased to −40° C. The cooling bath was removed and potassium carbonate (741.0 g, 5.358 mmol) was added with water until a total of 1.0 L was added. Off-gassing was observed and the temperature increased to 25° C. MTBE (1.5 L) was added and the reaction mixture was transferred to a separatory funnel. The layers were separated. The aqueous layer was diluted with water (500 mL) and extracted with MTBE (1 L)+EtOAc (500 mL) and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added and the suspension was heated to 40° C. to produce a homogeneous solution. The solution was allowed to cool to rt. Six volumes of heptane were added and the suspension was stirred 16 h. The suspension was filtered and the crystals were washed with 4:1 heptane: MTBE (500 mL), followed by heptane (500 mL). The solid was dried under vacuum, providing 4-bromo-3-hydroxymethyl-2-methyl phenol. $^1$H NMR (400 MHz, DLC/MSO-d$_6$): δ 9.52 (s, 1H), 7.21 (d, J=8.6 Hz, 1H), 6.71 (d, J=8.6 Hz, 1H), 4.88 (t, J=5.1 Hz, 1H), 4.59 (d, J=5.1 Hz, 2H), 2.23 (s, 3H).

Step B:
5-Hydroxy-4-methyl-3H-isobenzofuran-1-one

To a 2 L 3 neck flask equipped with overhead stirrer, N$_2$ inlet, and condenser were charged 4-bromo-3-hydroxymethyl-2-methyl phenol (100 g, 461 mmol), CuCN (83.0 g, 921 mmol), and DMF (500 mL). The solution was sparged with N$_2$ for 15 min, then was heated to 145° C. to obtain a homogeneous solution. The solution was aged at 145° C. for 2 h, then the reaction mixture was cooled to 95° C. 41.5 mL water was added (sparged with N$_2$), and the reaction aged for 20 h. The reaction was cooled to RT then the solids filtered through SolkaFloc® and the cake washed with 50 mL DMF. To a 3 L flask containing 1 L EtOAc was added the DMF filtrate. A precipitate coating formed in the bottom of the flask. The DMF/EtOAc suspension was filtered through SolkaFloc and the cake was washed with 250 mL EtOAc. The resulting filtrate was washed with 5% brine solution (3×500 mL). The aqueous layers were extracted with 500 mL EtOAc and the combined organics were dried over MgSO$_4$, filtered, and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one, 5-Hydroxy-4-methyl-3H-isobenzofuran-1-one. $^1$H NMR (400 MHz. DLC/MSO-d$_6$): δ 10.52 (s, 1H), 7.51 (d, J=8.3 Hz, 1H), 6.99 (d, J=8.3 Hz, 1H), 5.28 (s, 2H), 2.07 (s, 3H).

Step C:
4-methyl-1-oxo-1,3-dihydroisobenzofuran-5-yl trifluoromethanesulfonate

5-Hydroxy-4-methyl-3H-isobenzofuran-1-one (46.8 g, 285 mmol) was suspended in dichloromethane (935 mL) in a 2-L round bottom flask equipped with overhead stirrer under nitrogen. Triethylamine (59.5 mL, 427 mmol) was added and the reaction mixture was cooled in an ice bath to 3.8° C. Trifluoromethanesulfonic anhydride (67.4 mL, 399 mmol) was added via addition funnel over 50 min, keeping the temperature at; 10° C. After stirring the reaction mixture for an additional 15 min, the reaction mixture was quenched with water (200 mL), then stirred with DARCO® KB (activated carbon, 25 g) for 15 minutes. The biphasic mixture was filtered over SolkaFloc, washing with additional dichloromethane and transferred to a separatory funnel, whereupon it was diluted with additional water (300 mL). The layers were separated and the organic layer was washed with water (500 mL) and 10% brine (200 mL). The dichloromethane solution was dried over sodium sulfate, filtered and evaporated. The orange-red solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, the solid washed with heptane and dried under vacuum and nitrogen, providing trifluoromethanesulfonic acid 4-methyl-1-oxo-1,3-dihydroisobenzofuran-5-yl ester. $^1$H NMR (400 MHz, CDCl$_3$): δ 7.87 (d, J=8.4 Hz, 1H), 7.47 (d, J=8.4 Hz, 1H), 5.32 (s, 2H), 2.41 (s, 3H).

Step D: 4-methyl-5-vinylisobenzofuran-1 (3H)-one 4-methyl-1-oxo-1,3-dihydroisobenzofuran-5-yl trifluoromethanesulfonate (5.0 g, 16.88 mmol), potassium trifluoro (vinyl)borate (4.52 g, 33.8 mmol), and PdCl$_2$(dppf)-CH$_2$Cl$_2$ Adduct (0.689 g, 0.844 mmol) were placed in a reaction vessel, Ethanol (50 ml) was added to the mixture followed by triethylamine (4.71 ml, 33.8 mmol) and degassed with N$_2$. The resulting mixture was heated over night at 90° C. The reaction mixture was diluted with EtOAc and filtered through celite. The filtrate was evaporated to dryness and purified by silica gel column chromatography using (0-45)% EtOAc/Hexanes as mobile phase and the title product was isolated as white solid. LC/MS [M+H]$^+$=175

Step E: 4-methyl-1-oxo-1,3-dihydroisobenzofuran-5-carbaldehyde

The 4-methyl-5-vinylisobenzofuran-1(3H)-one (1.0 g, 5.74 mmol) was dissolved in Acetone (40 ml) and Water (40 ml), potassium osmate dihydrate (0.076 g, 0.207 mmol) was added to it and stirred for 5 min. Solid sodium periodate (4.90 g, 22.91 mmol) was added in 4 portions during 1 hour and the reaction temperature was maintained below 40° C. using an ice-bath. The resulting mixture was stirred for 1 hour at rt.

LCLC/MS at this stage showed complete consumption of starting material. The suspension (now) was filtered and the filtrate was concentrated to remove acetone and the aqueous layer was extracted with DCM (3×). The combined organic layers were washed with 10% Na$_2$S$_2$O$_3$ solution (2×), dried over anhydrous Na$_2$SO$_4$, filtered, and concentrated to get the product 4-methyl-1-oxo-1,3-dihydroisobenzofuran-5-carbaldehyde as a white solid. LC/MS: [M+H]$^+$=177

Intermediate 38

2-fluoro-4-(4,5,6,7-tetrahydro-1H-pyrazolo[3,4-c]pyridin-3-yl)benzonitrile

Step A: tert-butyl 3-(4-cyano-3-fluorophenyl)-4,5-dihydro-1H-pyrazolo[3,4-c]pyridine-6(7H)-carboxylate tert-butyl 3-oxopiperidine-1-carboxylate (1.0 g, 5.02 mmol) was dissolved in toluene (16 ml) and cooled to 0° C. under N$_2$. Lithium bis(trimethylsilyl)amide (11.04 ml, 11.04 mmol) was added quickly via syringe with stirring, and the formed anion (slurry) was allowed to sit for 1 minutes before the addition of 4-cyano-3-fluorobenzoyl chloride (921 mg, 5.02 mmol) in one portion. The flask was removed from the ice bath and allowed to stand for a couple of minutes and then acetic acid (3.014 g, 50.2 mmol) was added with stirring. EtOH (60 mL) and THF (25 mL) were added to form a homogeneous mixture (not a clear solution) followed by the addition of hydrazine (1.608 g, 50.2 mmol) (exothermic reaction but not boiling) and the resulting reaction mixture was stirred for 30 min. The reaction mixture was poured into 1N NaOH (aq.) and the aqueous layer was extracted with EtOAc (2×). The organic layer was washed with brine, dried over $Na_2SO_4$, concentrated to get the crude product which was purified by silica gel column chromatography using (10-20)% ACN/DCM to get the title product. LC/MS: $[M+H]^+=343.1$ Step B: 2-fluoro-4-(4,5,6,7-tetrahydro-1H-pyrazolo[3,4-c]pyridin-3-yl)benzonitrile To a solution of tert-butyl 3-(4-cyano-3-fluorophenyl)-4,5-dihydro-1H-pyrazolo[3,4-c]pyridine-6(7H)-carboxylate (120 mg, 0.351 mmol) in DCM (0.6 ml) was added trifluoro acetic acid (0.41 ml, 5.26 mmol) and the resulting mixture was stirred at rt for 2 h and then concentrated to get the title compound which was used in the next step with purification. LC/MS: $[M+H]^+=243.1$ Intermediate 39

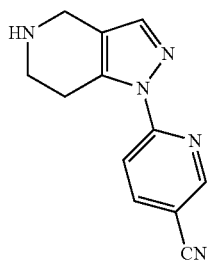 [SMILES: N#Cc1ccc(-n2ncc3c2CCNC3)nc1]

6-(4,5,6,7-tetrahydro-1H-pyrazolo[4,3-c]pyridin-1-yl)nicotinonitrile

Step A: tert-butyl 1-(5-cyanopyridin-2-yl)-6,7-dihydro-1H-pyrazolo[4,3-c]pyridine-5(4H)-carboxylate tert-butyl 6,7-dihydro-1H-pyrazolo[4,3-c]pyridine-5(4H)-carboxylate (931 mg, 4.17 mmol), 6-bromonicotinonitrile (2.29 g, 12.51 mmol), copper iodide (794 mg, 4.17 mmol), L-proline (576 mg, 5.0 mmol), and potassium carbonate (1.73 g, 12.51 mmol) were combined in DLC/MSO (25 ml) in a sealed tube and heated 16 h at 110° C. The solution was diluted with distilled $H_2O$ and extracted with EtOAc. The organic layer was separated, dried, filtered and concentrated to give the crude product as an oil which was purified by silica gel column chromatography (Biotage 100 g SNAP) using (12-100)% EtOAc/Hexanes as mobile phase to give the title product as a mixture of regioisomers (2:1 ratio). LC/MS: $[M+H]^+=326.1$ Step B: 6-(4,5,6,7-tetrahydro-1H-pyrazolo[4,3-c]pyridin-1-yl)nicotinonitrile tert-butyl 1-(5-cyanopyridin-2-yl)-6,7-dihydro-1H-pyrazolo[4,3-c]pyridine-5(4H)-carboxylate was dissolved in 4N-HCl in 1,4-dioxane (3.0 ml) and stirred at rt, concentrated to get the title product which was taken to the next step without purification.

Intermediate 40

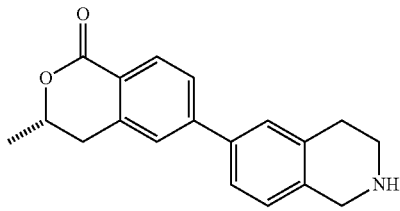 [SMILES: C[C@H]1Cc2cc(-c3ccc4c(c3)CCNC4)ccc2C(=O)O1]

(S)-3-methyl-6-(1,2,3,4-tetrahydroisoquinolin-6-yl)isochroman-1-one

Step A: (S)-tert-butyl 6-(3-methyl-1-oxoisochroman-6-yl)-3,4-dihydroisoquinoline-2(1H)-carboxylate (S)-3-methyl-6-(4,4,5,5-tetramethyl-1,3,2-dioxaborolan-2-yl)isochroman-1-one (598 mg, 2.075 mmol), tert-butyl 6-bromo-3,4-dihydroisoquinoline-2(1H)-carboxylate (648 mg, 2.075 mmol), palladium acetate (23.30 mg, 0.104 mmol), dicyclohexyl(2',6'-dimethoxy-[1,1'-biphenyl]-2-yl)phosphine (85 mg, 0.208 mmol) and potassium phosphate (723 mg, 4.15 mmol) were combined in THF (10 ml) and water (1 ml) in a microwave vial and heated at 120° C. under microwave conditions for 5 minutes. The reaction mixture was concentrated to dryness and purified by silica gel column chromatography using (10-100)% EtOAc/Hexanes and the title product was isolated as a yellow solid. LC/MS: $[M+H]^+=394.1$ Step B: (S)-3-methyl-6-(1,2,3,4-tetrahydroisoquinolin-6-yl)isochroman-1-one A solution of 4N HCl in dioxane (20 ml) was used to dissolve (S)-tert-butyl 6-(3-methyl-1-oxoisochroman-6-yl)-3,4-dihydroisoquinoline-2(1H)-carboxylate (365 mg, 0.928 mmol) and stirred for 2 hr. The solution was concentrated down to get the product, (S)-3-methyl-6-(1,2,3,4-tetrahydroisoquinolin-6-yl)isochroman-1-one, as solid and used without purification. LC/MS: $[M+H]^+=294.1$ Intermediate 41

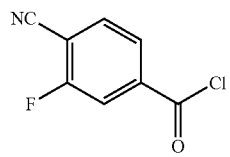 [SMILES: N#Cc1ccc(C(=O)Cl)cc1F]

4-cyano-3-fluorobenzoyl chloride

Step A: 4-cyano-3-fluorobenzoyl chloride 4-cyano-3-fluorobenzoic acid (2.5 g, 15.14 mmol) was suspended in DCM (80 ml), cooled in ice water bath, followed by addition of oxalyl dichloride (2.65 ml, 30.3 mmol) and 2 drops of DMF. The mixture was then stirred at rt for 1 h. The suspension turned to a clear solution. The mixture was quenched with 1 N HCl (50 ml) and extracted with EtOAc. The organic layer was washed with brine, dried over anhydrous Na$_2$SO$_4$, filtered, concentrated to get the crude title product which used for the next step with out further purification.

Intermediate 42

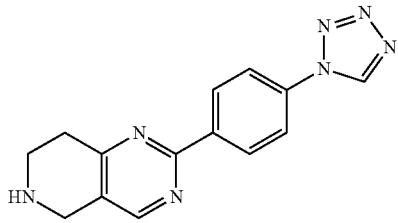 [SMILES: c1cc(-n2cnnn2)ccc1-c1ncc2c(n1)CCNC2]

2-(4-(1H-tetrazol-1-yl)phenyl)-5,6,7,8-tetrahydro-pyrido[4,3-d]pyrimidine

Step A: tert-butyl 2-(4-aminophenyl)-7,8-dihydro-pyrido[4,3-d]pyrimidine-6(5H)-carboxylate To a solution of (Z)-tert-butyl 3-((dimethylamino)methylene)-4-oxopiperidine-1-carboxylate (1 g, 3.93 mmol) in Ethanol (10 ml) was added 4-aminobenzamidine dihydrochloride (0.818 g, 3.93 mmol) followed by sodium carbonate (1.250 g, 11.80 mmol) and the resulting mixture was refluxed for 16 h. The mixture was then partitioned between EtOAc and water and the aqueous layer was extracted with EtOAc (3×). The combined organic phase was washed with brine, dried over anhydrous MgSO$_4$, and filtered. Concentration of filtrate gave the title product as bright yellow solid which was directly used in the next step without further purification. LC/MS: [M+H]$^+$=327.3

Step B: tert-butyl 2-(4-(1H-tetrazol-1-yl)phenyl)-7,8-dihydropyrido[4,3-d]pyrimidine-6(5H)-carboxylate To a solution of tert-butyl 2-(4-aminophenyl)-7,8-dihydropyrido[4,3-d]pyrimidine-6(5H)-carboxylate (400 mg, 1.226 mmol) and sodium azide (159 mg, 2.451 mmol) in acetic acid (6 ml) was added triethyl orthoformate (0.408 ml, 2.451 mmol) at rt. The reaction mixture was stirred at 100° C. for 1.5 h. The mixture was partitioned between EtOAc and water and the aqueous layer was extracted with EtOAc (3×). The combined organic phase was washed with brine, dried over anhydrous MgSO$_4$ and filtered. Concentration of filtrate was followed by purification by silica gel column chromatography using (0-100)% EtOAc/Hexanes as mobile phase to give the title compound as a yellow solid. LC/MS: [M+H]$^+$=380.3

Step C: 2-(4-(1H-tetrazol-1-yl)phenyl)-5,6,7,8-tetrahydropyrido[4,3-d]pyrimidine tert-butyl 2-(4-(1H-tetrazol-1-yl)phenyl)-7,8-dihydropyrido[4,3-d]pyrimidine-6(5H)-carboxylate (383 mg, 1.009 mmol) and HCl, 4M in 1,4-dioxane (90 ml, 360 mmol) were combined at rt and the mixture was stirred at rt for 2 h. The mixture was then concentrated to give the title compound which was used in the next step without further purification.

Intermediate 43

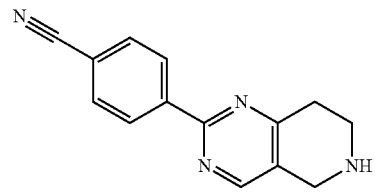 [SMILES: N#Cc1ccc(-c2ncc3c(n2)CCNC3)cc1]

4-(5,6,7,8-tetrahydropyrido[4,3-d]pyrimidin-2-yl)benzonitrile

Step A: tert-butyl 2-(4-carbamoylphenyl)-7,8-dihydropyrido[4,3-d]pyrimidine-6(5H)-carboxylate To a solution of (Z)-tert-butyl 3-((dimethylamino)methylene)-4-oxopiperidine-1-carboxylate (995 mg, 3.91 mmol) in EtOH (5 ml) was added 4-Carbamimidoyl-benzamide. hydrochloride (781 mg, 3.91 mmol) followed by sodium carbonate (829 mg, 7.82 mmol) and resulting mixture was refluxed for 16 h. The mixture was partitioned between EtOAc and water and aqueous layer was extracted with EtOAc (3×). Combined organic layer was washed with brine, dried over MgSO$_4$, filtered, concentrated to get the title compound as a slightly yellow solid. LC/MS: [M+H]$^+$=355.2

Step B: tert-butyl 2-(4-cyanophenyl)-7,8-dihydropyrido[4,3-d]pyrimidine-6(5H)-carboxylate To a heterogeneous mixture of tert-butyl 2-(4-carbamoylphenyl)-7,8-dihydropyrido[4,3-d]pyrimidine-6(5H)-carboxylate (854 mg, 2.41 mmol) and DIPEA (0.84 ml, 4.82 mmol) in DCM (15 ml) was added trifluoro acetic anhydride (0.37 ml, 2.65 mmol) at rt. After the addition of trifluoro acetic anhydride solution became clear. The reaction mixture was stirred at rt for 2 h. After concentration the residue was partitioned between EtOAc and aq NaHCO$_3$ (sat'd) and aqueous layer was extracted with EtOAc (3×) Combined organic layer was washed with brine, dried over MgSO$_4$, filtered, concentrated to get the title compound as a slightly yellow solid. LC/MS: [M-Bu$^t$]$^+$=355.2

Step C: 4-(5,6,7,8-tetrahydropyrido[4,3-d]pyrimidin-2-yl)benzonitrile

To a solution of tert-butyl 2-(4-cyanophenyl)-7,8-dihydropyrido[4,3-d]pyrimidine-6(5H)-carboxylate (1.39 g, 4.13 mmol) in MeOH (20 ml) and 1,4-dioxane (10 ml) was added 1.25 N—HCl in MeOH (230 ml) at rt and stirred for 3 h. The reaction mixture was concentrated to 4-(5,6,7,8-tetrahydropyrido[4,3-d]pyrimidin-2-yl)benzonitrile as white solid. LC/MS: [M+H]$^+$=237.3

Intermediate 44

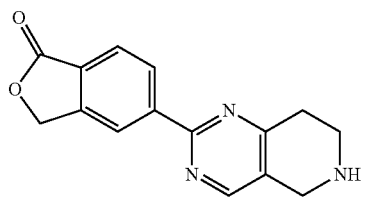 [SMILES: O=C1OCc2cc(-c3ncc4c(n3)CCNC4)ccc21]

5-(5,6,7,8-tetrahydropyrido[4,3-d]pyrimidin-2-yl)isobenzofuran-1(3H)-one

Step A: tert-butyl 2-(1-oxo-1,3-dihydroisobenzofuran-5-yl)-7,8-dihydropyrido[4,3-d]pyrimidine-6(5H)-carboxylate To a solution of (Z)-tert-butyl 3-((dimethylamino)methylene)-4-oxopiperidine-1-carboxylate (206 mg, 0.811 mmol) in ethanol (4 ml) was added 1-oxo-1,3-dihydroisobenzofuran-5-carboximidamide (186.3 mg, 0.811 mmol) followed by sodium carbonate (258 mg, 2.434 mmol). The reaction mixture was refluxed for 16 h. The mixture was then partitioned between EtOAc and water and the aqueous layer was extracted with EtOAc (3×). The combined organic phase was washed with brine, dried over anhydrous MgSO$_4$, filtered and concentrated. 10% MeOH/DCM was added to the residue and a solid impurity was filtered. The filtrate was then purified by preparative TLC using 10% MeOH/DCM as mobile phase to give the title product as white powder. LC/MS: [M+H]$^+$=368.3

Step B: 5-(5,6,7,8-tetrahydropyrido[4,3-d]pyrimidin-2-yl)isobenzofuran-1(3H)-one tert-butyl 2-(1-oxo-1,3-dihydroisobenzofuran-5-yl)-7,8-dihydropyrido[4,3-d]pyrimidine-6(5H)-carboxylate (51.4 mg, 0.140 mmol) was dissolved in HCl, 4M in 1,4-dioxane (10 ml, 40.0 mmol) at rt and the resulting reaction mixture was stirred at rt 16 h. The mixture was then concentrated to give the title compound as slightly pink/white powder which was taken to next reaction without purification.

Intermediate 45

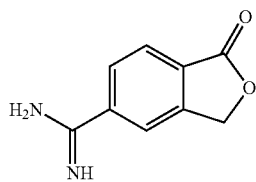

1-oxo-1,3-dihydroisobenzofuran-5-carboximidamide

Step A: methyl 1-oxo-1,3-dihydroisobenzofuran-5-carbimidate hydrochloride

A solution of 5-cyanophthalide (2.5 g, 15.71 mmol) in MeOH (50 ml) and Dioxane (50.0 ml) was placed in an ice bath and HCl gas was added to the flask for 3 min. The ice bath was then removed and the mixture was warmed to rt. No product precipitated out, so the mixture was left in the freezer for over the weekend. A white solid precipitated which was filtered and the filtrate was concentrated to get the title compound as white powder. LC/MS: [M+H]$^+$=192.3

Step B: 1-oxo-1,3-dihydroisobenzofuran-5-carboximidamide methyl 1-oxo-1,3-dihydroisobenzofuran-5-carbimidate hydrochloride (180 mg, 0.791 mmol) was dissolved in ammonia in MeOH (8 ml, 56.0 mmol) and stirred at rt 16 h. LC-LC/MS indicated the formation of desired product. The reaction mixture was concentrated to give the title product as slightly pink/white powder, which was directly used in the next step without purification. LC/MS: [M+H]$^+$=177.3

Intermediate 46

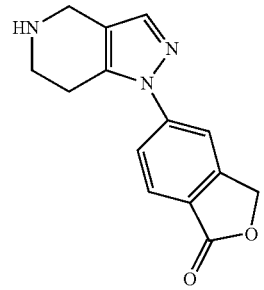 [SMILES: O=C1OCc2cc(-n3ncc4c3CCNC4)ccc21]

5-(4,5,6,7-tetrahydro-1H-pyrazolo[4,3-c]pyridin-1-yl)isobenzofuran-1(3H)-one

Step A: tert-butyl 1-(1-oxo-1,3-dihydroisobenzofuran-5-yl)-6,7-dihydro-1H-pyrazolo[4,3-c]pyridine-5(4H)-carboxylate To a solution of (Z)-tert-butyl 3-((dimethylamino)methylene)-4-oxopiperidine-1-carboxylate (505 mg, 1.986 mmol) in Ethanol (10 ml) was added 5-hydrazinylisobenzofuran-1(3H)-one (326 mg, 1.986 mmol) followed by sodium carbonate (421 mg, 3.97 mmol). The reaction mixture was refluxed for 16 h. The mixture was then partitioned between EtOAc and water and the aqueous layer was extracted with EtOAc (3×). The combined organic phase was washed with brine, dried over anhydrous MgSO$_4$, and filtered. Concentration of the filtrate was followed by purification by silica gel column chromatography using (0-100)% EtOAc/Hexanes as mobile phase gave the title product as viscous yellow oil. LC/MS: [M+H]$^{30}$=356.3

Step B: 5-(4,5,6,7-tetrahydro-1H-pyrazolo[4,3-c]pyridin-1-yl)isobenzofuran-1(3H)-one tert-butyl 1-(1-oxo-1,3-dihydroisobenzofuran-5-yl)-6,7-dihydro-1H-pyrazolo[4,3-c]pyridine-5 (4H)-carboxylate (577 mg, 1.624 mmol) was dissolved in HCl, 4M in 1,4-dioxane (100 ml, 400 mmol) at rt. Few drops of MeOH was added to help with solubility. The reaction mixture stirred at rt 16 h. The mixture was then concentrated to give the title compound as bright yellow solid which was taken to next reaction without purification.

Intermediate 47

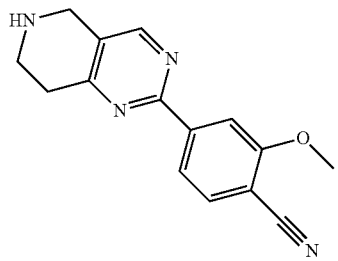 [SMILES: COc1cc(-c2ncc3c(n2)CCNC3)ccc1C#N]

tert-butyl 2-(4-cyano-3-methoxyphenyl)-7,8-dihydropyrido[4,3-d]pyrimidine-6(5H)-carboxylate Step A: tert-butyl 2-(4-bromo-3-methoxyphenyl)-7,8-dihydropyrido[4,3-d]pyrimidine-6(5H)-carboxylate To a solution of (Z)-tert-butyl 3-((dimethylamino)methylene)-4-oxopiperidine-1-carboxylate (0.9 g, 3.54 mmol) in EtOH (10 ml) was added 4-bromo-3-methoxybenzimidamide (1.0 g, 3.54 mmol) followed by sodium carbonate (750 mg, 7.08 mmol) and refluxed for 16 hr. The mixture was partitioned between EtOAc and water and aqueous layer was extracted with EtOAc (3×). Combined organic layer was washed with brine, dried over MgSO$_4$, filtered, concentrated to give the title compound as slightly yellow solid. LC/MS: [M+H]$^+$=420.3

Step B: tert-butyl 2-(4-cyano-3-methoxyphenol)-7,8-dihydropyrido[4,3-d]pyrimidine-6(5H)-carboxylate To a solution of tert-butyl 2-(4-bromo-3-methoxyphenyl)-7,8-dihydropyrido[4,3-d]pyrimidine-6(5H)-carboxylate (400 mg, 0.952 mmol) in DMF (5 ml) were added zinc cyanide (1.11 g, 9.52 mmol), tris(dibenzylideneacetone)dipalladium(0) (174 mg, 0.190 mmol), and 1,1'-bis(diphenylphosphanyl) ferrocene (106 mg, 0.19 mmol) sequentially and heated at 100° C. for 1 h under microwave condition. The mixture was partitioned between EtOAc and water and aqueous layer was extracted with EtOAc (3×). Combined organic layer was washed with brine, dried over MgSO$_4$, filtered, concentrated and purified by preparative TLC using 50% EtOAc/Hexanes as a solvent system to give the title compound as solid. LC/MS: [M+H]$^+$=367.3

To a heterogeneous solution of tert-butyl 2-(4-cyano-3-methoxyphenyl)-7,8-dihydropyrido[4,3-d]pyrimidine-6(5H)-carboxylate (61 mg, 0.166 mmol) in MeOH (1 ml) was added 2 ml of 4 N—HCl in 1,4-dioxane at rt and stirred for 4 h. The solution was concentrated to give the title compound as brown residue.

Intermediate 48

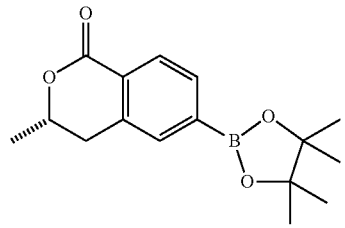

(S)-3-methyl-6-(4,4,5,5-tetramethyl-1,3,2-dioxaborolan-2-yl)isochroman-1-one

Step A:
6-Bromo-3-methyl-3,4-dihydro-1H-isochromen-1-one

A solution of diisopropylamine (13 ml, 93 mmol) in THF (155 ml) at −78° C. was treated with n-BuLi (1.6 M in hexanes; 58 ml, 93 mmol) over a period of 15 minutes using a syringe pump. In a separate flask, a solution of 2-methyl-4-bromo benzoic acid (10 g, 46 mmol) and HMPA (8.3 ml, 46 mmol) in THF (155 ml) was cooled to −78° C. Methyl lithium (29 ml, 46 mmol) was added slowly via syringe to the cooled solution in order to make the lithio carboxylate. The resulting solution was stirred for 10 minutes and then transferred via cannula to the LDA solution at −78° C. The resulting bright red solution was stirred at −78° C. for an additional 1 hour before being quenched with anhydrous acetaldehyde (7.9 ml, 140 mmol) (color changed from red to orange to clear yellow) and the reaction was then taken out of the dry ice acetone bath and allowed to stir for an additional 1 hour. The flask containing the reaction mixture was then resubmerged in the dry ice acetone bath before it was quenched with 4 M HCl in Dioxane (50 mL) followed by 25 mL of MeOH. The reaction was stirred at room temp for an additional 1 hour. The crude reaction was partitioned b/w 200 mL EtOAc and 200 mL water. The organic layer was washed with water, brine, dried with mag. sulfate, filtered and concentrated. Purification via MPLC (30-70% DCM/hexanes). 6-bromo-3-methyl-3,4-dihydro-1H-isochromen-1-one as an off white solid, yield 9.4 g, 84%. $^1$H NMR (500 MHz; CDCl$_3$): 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H). LC-LC/MS (IE, m/z): 241 [M+1]$^+$.

Step B: (3S)-6-Bromo-3-methyl-3,4-dihydro-1H-isochromen-1-one

Chiral separation of racemic 6-bromo-3-methyl-3,4-dihydro-1H-isochromen-1-one using ChiralPak AS 4.6×250 mm 10 u column, eluting with 60% IPA/Heptane. The faster eluting isomer was identified as the S-isomer. (3S)-6-Bromo-3-methyl-3,4-dihydro-1H-isochromen-1-one. $^1$H NMR (500 MHz, CDCl$_3$): 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H). LC-LC/MS (IE, m/z): 241 [M+1]$^+$.

Step C: (S)-3-methyl-6-(4,4,5,5-tetramethyl-1,3,2-dioxaborolan-2-yl)isochroman-1-one The mixture of potassium acetate (0.489 g, 4.98 mmol), BISPIN (1.264 g, 4.98 mmol), and (S)-6-bromo-3-methylisochroman-1-one (1 g, 4.15 mmol) in Dioxane (20 ml) was degassed by N₂ for 30 min followed by addition of PdCl₂ (dppf) (0.152 g, 0.207 mmol). The resulting mixture was heated at 80° C. 16 h. After filtration, the filtrate was concentrated and the residue was purified by silica gel column chromatography (80 g RediSep column) using (10-20)% EtOAc/hexane to give the title compound.

Intermediate 49

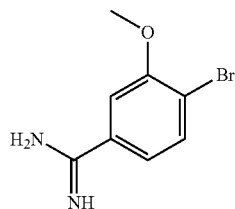

4-bromo-3-methoxybenzimidamide

Step A: 4-bromo-3-methoxybenzimidamide

HCl gas was bubbled through a solution of 4-bromo-3-methoxybenzonitrile (4.55 g, 21.46 mmol) in EtOH (20 ml) at 0° C. and stirred at 0° C. for 5 min. The solution was kept in the hood at rt for 24 h. Solid formed which was filtered and dissolved in 7N NH₃ in MeOH (35 ml) and stirred at rt for 2 days. The resulting mixture was concentrated to get the title product as solid. LC/MS: [M+H]⁺=230.2

Intermediate 50

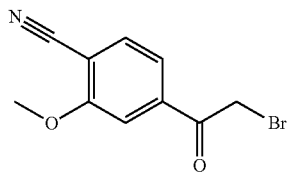

4-(2-bromoacetyl)-2-methoxybenzonitrile

Step A: 4-acetyl-2-methoxybenzonitrile

To a mixture of 4-bromo-2-methoxy benzonitrile (1 g, 4.72 mmol), butyl vinyl ether (2.362 g, 23.58 mmol), 1,3-bis(diphenylphosphino)propane (0.097 g, 0.236 mmol), palladium (II) acetate (0.053 g, 0.236 mmol) and 1-butyl-3-methylimidazolium tetrafluoro borate (0.533 g, 2.358 mmol) in DLC/MSO (4.72 ml) was added diisopropylamine (0.807 ml, 5.66 mmol) in a microwave vial. The reaction mixture was degassed with argon and stirred at 115° C. for 18 h. The mixture was partitioned between EtOAc and H₂O and the aqueous layer was extracted with EtOAc (3×). The combined organic phase was washed with brine, dried over anhydrous MgSO₄, and filtered. The residue was then dissolved in MeOH/DLC/MSO (25 ml/5 ml), then 3N HCl (20 ml) was added. The mixture was stirred at rt for 3 h. After concentration the residue was partitioned between DCM and water and the aqueous layer was extracted with DCM (3×).

The combined organic phase was washed with brine, dried over anhydrous MgSO₄, and filtered. The filtrate was concentrated and purified by silica gel column chromatography using (0-60)% EtOAc/Hexanes as mobile phase to give the title product as a pale yellow solid.

Step B: 4-(2-bromoacetyl)-2-methoxybenzonitrile

To a solution of 4-acetyl-2-methoxybenzonitrile (315 mg, 1.798 mmol) in THF (9 ml) was added copper (II) bromide (442 mg, 1.978 mmol) at rt and the mixture was stirred at rt for 18 h. The mixture was partitioned between EtOAc and H₂O and the aqueous layer was extracted with EtOAc (3×). The combined organic phase was washed with brine, dried over anhydrous MgSO4, and filtered. The filtrate was concentrated and purified by silica gel column chromatography using (0-60) EtOAc/Hexanes to give the title compound as very pale yellow powder.

Intermediate 51

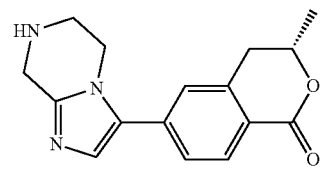 [SMILES: C[C@H]1Cc2cc(-c3cnc4n3CCNC4)ccc2C(=O)O1]

(S)-3-methyl-6-(5,6,7,8-tetrahydroimidazo[1,2-a]pyrazin-3-yl)isochroman-1-one

Step A: (S)-tert-butyl 3-(3-methyl-1-oxoisochroman-6-yl)-5,6-dihydroimidazo[1,2-a]pyrazine-7(8H)-carboxylate A mixture of tert-butyl 3-bromo-5,6-dihydroimidazo[1,2-a]pyrazine-7(8H)-carboxylate (109 mg, 0.361 mmol), (S)-3-methyl-6-(4,4,5,5-tetramethyl-1,3,2-dioxaborolan-2-yl)isochroman-1-one (208 mg, 0.721 mmol), Pd(PPH₃)₂Cl₂ (25.3 mg, 0.0036 mmol), Na₂CO₃ (2M, 361 ul) in dioxane (3.6 ml) was heated at 90° C. 16 h. The reaction mixture was diluted with H₂O and extracted with EtOAc(3×). Combined organic layer was washed with brine, dried over MgSO₄, filtered, concentrated and purified by flash chromatography (snap 25 g) using (7-60-100)% EtOAc/Hexanes as mobile phase to give the title product as white foam. LC/MS: [M+H]⁺=384.2

Step B: (S)-3-methyl-6-(5,6,7,8-tetrahydroimidazo[1,2-a]pyrazin-3-yl)isochroman-1-one (S)-tert-butyl 3-(3-methyl-1-oxoisochroman-6-yl)-5,6-dihydroimidazo[1,2-a]pyrazine-7(8H)-carboxylate (122 mg, 0.312 mmol) and 4N-HCl in dioxane (0.08 ml) was stirred at rt for 2 h and then concentrated to dryness. The residue was partitioned between 0.1N NaOH and IPA/CHCl₃(1/3) and the aqueous layer was extracted with IPA/CHCl₃(1/3) (3×), dried over MgSO₄, filtered and concentrated to give the title product as white solid. LC/MS: [M+H]⁺=284.13

Intermediate 52

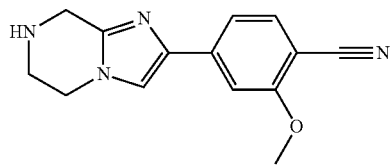

2-methoxy-4-(5,6,7,8-tetrahydroimidazo[1,2-a]pyrazin-2-yl)benzonitrile

Step A: tert-butyl 2-(4-cyano-3-methoxyphenyl)-5,6-dihydroimidazo[1,2-a]pyrazine-7(8H)-carboxylate To a solution of tert-butyl 3-amino-5,6-dihydropyrazine-1(2H)-carboxylate (184 mg, 0.921 mmol) in 2-propanol (5 ml) was added 4-(2-bromoacetyl)-2-methoxybenzonitrile (195 mg, 0.767 mmol) at rt, 3 ml of MeOH was added to help with solubility. The reaction mixture was microwaved for 30 mins at 100° C. The mixture was partitioned between EtOAc and aqueous NaHCO₃ (saturated) and the aqueous layer was extracted with EtOAc (2×). The combined organic phase was washed with brine and dried over anhydrous MgSO₄, filtered, concentrated and purified by preparative TLC using 10% MeOH/DCM as mobile phase to give the title compound as yellow powder. LC/MS: [M+H]⁺=355.28

Step B: 2-methoxy-4-(5,6,7,8-tetrahydroimidazo[1,2-a]pyrazin-2-yl)benzonitrile

The tert-butyl 2-(4-cyano-3-methoxyphenyl)-5,6-dihydroimidazo[1,2-a]pyrazine-7(8H)-carboxylate was dissolved in 4N HCl in 1,4-dioxane (10 ml) at rt, a few drops of MeOH was added to help with solubility. The reaction mixture stirred at rt for 2 h. The mixture was then concentrated to give 2-methoxy-4-(5,6,7,8-tetrahydroimidazo[1,2-a]pyrazin-2-yl)benzonitrile as tan/orange powder.

Intermediate 53

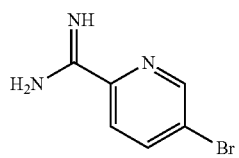

5-bromopicolinimidamide

Step A: ethyl 5-bromopicolinimidate

A mixture of 5-bromopicolinonitrile (1.0 g, 5.46 mmol) and MeONa (10.8 mg, 0.2 mmol) in MeOH (10 ml) was heated under microwave condition at 100° C. for 20 minutes. After cooling to rt, the solution was used directly to the next step.

Step B: 5-bromopicolinimidamide

To a solution of ethyl 5-bromopicolinimidate (5.46 mmol) in MeOH (10 ml) was added NH₄Cl (306.9 mg, 5.74 mmol) at one portion and the reaction was heated under microwave condition at 80° C. for 40 minutes. After cooling to rt, the mixture was concentrated and the residue was washed with ether to give the title compound as white solid. LC/MS: [M+H]⁺=202.0

Intermediate 54

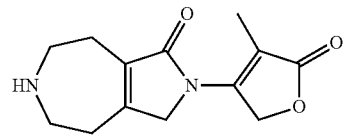 [SMILES: CC1=C(N2CC3=C(CCNCC3)C2=O)COC1=O]

2-(4-methyl-5-oxo-2,5-dihydrofuran-3-yl)-2,3,5,6,7,8-hexahydropyrrolo[3,4-d]azepin-1(4H)-one Step A: 1-tert-Butyl 4-methyl 4-(2-((tert-butoxycarbonyl)amino)-1-hydroxyethyl)piperidine-1,4-dicarboxylate To a solution of LDA (prepared by adding n-butyllithium (20 mL, 49.3 mmol) to diisopropylamine (5.16 mg, 51.0 mmol) in THF (40 mL) at 0° C., stir for 30 min) was added 1-tert-butyl 4-methyl piperidine-1,4-dicarboxylate (4.00 g, 16.4 mmol) in TMEDA (15 mL, 99 mmol) dropwise via syringe pump at −78° C. for 10 min. The mixture was stirred at the same temperature for 30 min. tert-butyl (2-oxoethyl)carbamate (8.11 g, 51.0 mmol) in THF (20 mL) was added slowly by syringe pump for 15 min. The mixture was stirred at −78° C. for 30 min, quenched with saturated NH₄Cl at −78° C., warmed up to rt and diluted with EtOAc (200 mL). The organic layer was separated, and the aqueous layer was extracted with EtOAc (100 mL). The combined organic layers were washed with brine, dried (MgSO₄), and concentrated. The residue was purified by column chromatography (80 g, silical gel, MeOH/DCM, gradien 0-10%, monitor at 210 nM) to afford 1-tert-butyl 4-methyl 4-(2-((tert-butoxycarbonyl)amino)-1-hydroxyethyl)piperidine-1,4-dicarboxylate. LC/LC/MS: [(M+1)]⁺=403

Step B: tert-Butyl 4-hydroxy-1-oxo-2,8-diazaspiro[4.5]decane-8-carboxylate

To the solution of 1-tert-butyl 4-methyl 4-(2-((tert-butoxycarbonyl)amino)-1-hydroxyethyl)piperidine-1,4-dicarboxylate (4000 mg, 9.94 mmol) in DCM (100 mL) was added TFA (23 mL, 298 mmol) at 0° C. and the resulting solution was stirred for 2 h. After removing the volatiles, it was put under high vacuum briefly to remove excess TFA, and the residue was dissolved in MeOH (100 mL), and potassium carbonate (13.7 g, 99 mmol) was added. The reaction mixture was heated at 60° C. for 2 h. After cooling to rt, aqueous NaHCO₃ (50 mL) was added to the reaction mixture. (Boc)₂O (6.51 g, 29.8 mmol) was added, and the reaction mixture was stirred at 16 h. The reaction mixture was extracted with DCM, dried with MgSO₄, and concentrated to give the crude product, which was purified by column chromatography (0-20% MeOH/DCM, monitor at 210 nM) to afford tert-butyl 4-hydroxy-1-oxo-2,8-diazaspiro[4.5]decane-8-carboxylate. LC/LC/MS: [(M+1)]⁺=271

Step C: tert-Butyl 4-hydroxy-2-(4-methyl-5-oxo-2,5-dihydrofuran-3-yl)-1-oxo-2,8-diazaspiro[4.5]decane-8-carboxylate To a round bottom flask was charged tert-butyl 4-hydroxy-1-oxo-2,8-diazaspiro[4.5]decane-8-carboxylate (400 mg, 1.48 mmol), 4-methyl-5-oxo-2,5-dihydrofuran-3-yl trifluoromethanesulfonate (546 mg, 2.22 mmol), $Pd_2(dba)_3$ (33.9 mg, 0.037 mmol), Xantphos (64.2 mg, 0.111 mmol), and cesium carbonate (964 mg, 2.96 mmol). The flask was equipped with a condenser, vacuumed and backfilled with $N_2$ and filled with Dioxane (6 mL). The reaction mixture was heated at 90° C. 16 h, and filtered through celite. The filtrate was evaporated to give the crude product, which was purified by column chromatography (0-10% MeOH/DCM) to give tert-butyl 4-hydroxy-2-(4-methyl-5-oxo-2,5-dihydrofuran-3-yl)-1-oxo-2,8-diazaspiro[4.5]decane-8-carboxylate. LC/LC/MS: $[(M+1)]^+=367$

Step D: tert-Butyl 2-(4-methyl-5-oxo-2,5-dihydrofuran-3-yl)-1-oxo-2,8-diazaspiro[4.5]dec-3-ene-8-carboxylate To a solution of tert-butyl 4-hydroxy-2-(4-methyl-5-oxo-2,5-dihydrofuran-3-yl)-1-oxo-2,8-diazaspiro[4.5]decane-8-carboxylate (500 mg, 1.365 mmol) in DCM (14 mL) at −78° C. was added triethylamine trihydrofluoride (445 µl, 2.73 mmol), triethylamine (190 µl, 1.36 mmol), and XtalFluor-E (469 mg, 2.05 mmol). The reaction mixture was stirred 16 h while warming up to rt, and quenched with aqueous $NaHCO_3$. The organic layer was separated and the aqueous layer was extracted with DCM (30 mL). The combined organic layers were dried ($MgSO_4$) and purified by column chromatography (80 g silica gel ISCO gold column, 0-100% EtOAc/hex) to give tert-butyl 4-fluoro-2-(4-methyl-5-oxo-2,5-dihydrofuran-3-yl)-1-oxo-2,8-diazaspiro[4.5]decane-8-carboxylate {LC/LC/MS: $[(M+1)]^+=369$}, and tert-butyl 2-(4-methyl-5-oxo-2,5-dihydrofuran-3-yl)-1-oxo-2,8-diazaspiro[4.5]dec-3-ene-8-carboxylate {LC/LC/MS: $[(M+1)]^+=349$}, and tert-butyl 2-(4-methyl-5-oxo-2,5-dihydrofuran-3-yl)-1-oxo-2,3,4,5,7,8-hexahydropyrrolo[3,4-d]azepine-6(1H)-carboxylate {LC/LC/MS: $[(M+1)]^+=349$}.

Step D: 2-(4-Methyl-5-oxo-2,5-dihydrofuran-3-yl)-2,3,5,6,7,8-hexahydropyrrolo[3,4-d]azepin-1(4H)-one tert-Butyl 2-(4-methyl-5-oxo-2,5-dihydrofuran-3-yl)-1-oxo-2,3,4,5,7,8-hexahydropyrrolo[3,4-d]azepine-6(1H)-carboxylate (80 mg, 0.230 mmol) in DCM (1.0 mL) was treated with TFA (0.53 mL, 6.89 mmol) at 0° C. to free Boc and give the TFA salt. Then a 2 g Bond Elut SCX ion exchange column was first rinsed with MeOH, then loaded with a sample in MeOH, washed with MeOH dropwise to remove TFA, and finally rinsed with 2N $NH_3$/MeOH to give the title compound as a free amine. LC/LC/MS: $[(M+1)]^+=249$

Example 1

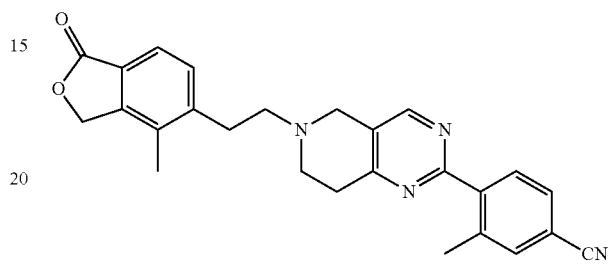

3-methyl-4-(6-(2-(4-methyl-1-oxo-1,3-dihydroisobenzofuran-5-yl)ethyl)-5,6,7,8-tetrahydropyrido[4,3-d]pyrimidin-2-yl)benzonitrile To a solution of 3-methyl-4-(5,6,7,8-tetrahydropyrido[4,3-d]pyrimidin-2-yl)benzonitrile (0.45 mmol) in DCM (10 ml) was added (4-Methyl-1-oxo-1,3-dihydro-2-benzofuran-5-yl)acetaldehyde (Intermediate 2, 85 mg, 0.44 mmol) followed by $NaCNBH_3$ (100 mg, 1.25 mmol) as one portion, and the reaction was stirred at rt for 12 hour. The mixture was poured into water and the aqueous layer was extracted with EtOAc (3×). The combined organic layers were washed with water, brine, dried, filtered and concentrated. The residue was purified by preparative TLC to give the title product. $^1$H-NMR (400 MHz, $CDCl_3$) δ ppm 8.48 (s, 1H), 7.77-7.79 (m, 1), 7.65-7.67 (m, 1H), 7.51-7.52 (m, 2H), 7.32-7.34 (m, 1H), 5.19 (s, 2H), 3.74 (s, 2H), 2.93-3.05 (m, 6H), 2.75-2.79 (m, 2H), 2.48 (s, 3H), 2.76-2.80 (m, 2H), 2.27 (s, 3H).

| Example | Intermediates | Structure & name | Characterization |
| --- | --- | --- | --- |
| 2 | 1 & 43 | 4-{6-[2-(1-oxo-1,3-dihydro-2-benzofuran-5-yl)ethyl]-5,6,7,8-tetrahydropyrido[4,3-d]pyrimidin-2-yl}benzonitrile | LC/MS [M + H]$^+$ = 396.2 |

| Example | Intermediates | Structure & name | Characterization |
|---|---|---|---|
| 3 | 1 & 18 | 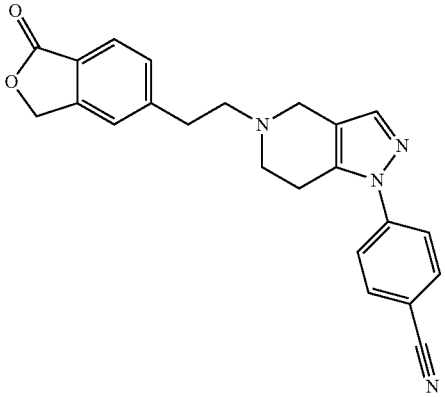 [SMILES: N#Cc1ccc(-n2ncc3c2CCN(CCc2ccc4c(c2)COC4=O)C3)cc1]<br>4-{5-[2-(1-oxo-1,3-dihydro-2-benzofuran-5-yl)ethyl]-4,5,6,7-tetrahydro-1H-pyrazolo[4,3-c]pyridin-1-yl}benzonitrile | LC/MS [M + H]$^+$ = 385.2 |
| 4 | 2 & 43 | 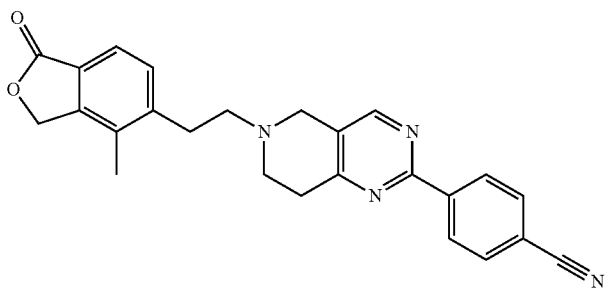 [SMILES: Cc1c(CCN2CCc3nc(-c4ccc(C#N)cc4)ncc3C2)ccc2c1COC2=O]<br>4-{6-[2-(4-methyl-1-oxo-1,3-dihydro-2-benzofuran-5-yl)ethyl]-5,6,7,8-tetrahydropyrido[4,3-d]pyrimidin-2-yl}benzonitrile | LC/MS [M + H]$^+$ = 411.3 |
| 5 | 1 & 20 | 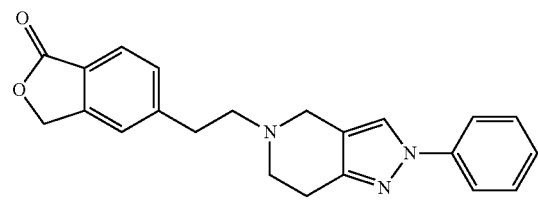<br>4-{5-[2-(1-oxo-1,3-dihydro-2-benzofuran-5-yl)ethyl]-4,5,6,7-tetrahydro-2H-pyrazolo[4,3-c]pyridin-2-yl}benzonitrile | $^1$H-NMR (500 MHz, CDCl$_3$) δ ppm 7.89 (d, 1H, J = 7.6 Hz), 7.78 (m, 4H), 7.56 (m, 2H), 5.3 (s, 2H), 3.72 (s, 2H), 3.08-3.05 (m, 2H) |

-continued

| Example | Intermediates | Structure & name | Characterization |
|---|---|---|---|
| 6 | 1 & 42 | 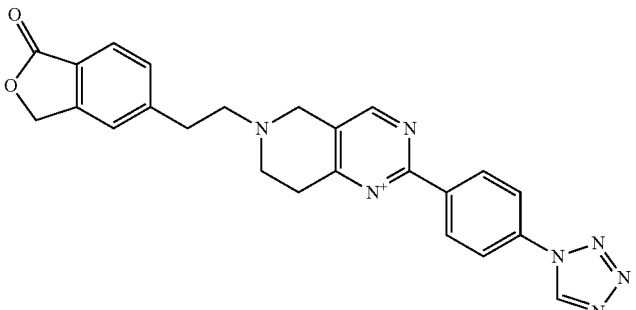<br>6-[2-(1-oxo-1,3-dihydro-2-benzofuran-5-yl)ethyl]-2-[4-(1H-tetrazol-1-34)phenyl]-5,6,7,8-tetrahydropyrido[4,3-d]pyrimidine-1,6-diium | $^1$H-NMR (500 MHz, CD$_3$OD) δ ppm 9.85 (s, 1H), 8.78 (s, 1H), 8.72(d, 2H, J = 8.7 Hz), 8.05 (d, 2H, J = 8.4 Hz),7.89 (d, 1H, J = 8.1 Hz), 7.63 (m, 2H), 4.63 (bs, 2H) |
| 7 | 2 & 42 | 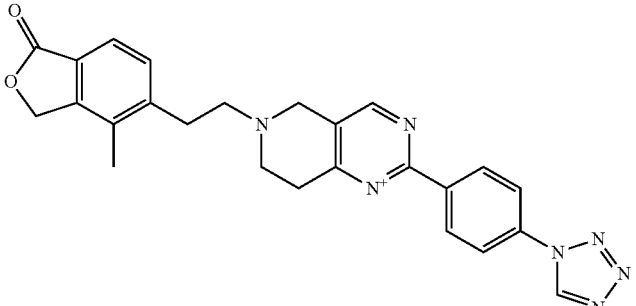<br>6-[2-(4-methyl-1-oxo-1,3-dihydro-2-benzofuran-5-yl)ethyl]-2-[4-(1H-tetrazol-1-yl)phenyl]-5,6,7,8-tetrahydropyrido[4,3-d]pyrimidine-1,6-diium | $^1$H-NMR (500 MHz, CD$_3$OD) δ ppm 9.86 (s, 1H), 8.77 (s, 1H), 8.70 (d, 2H, J = 8.7 Hz), 8.03 (d, 2H, J = 8.7 Hz), 7.70 (d, 1H, J = 7.8 Hz), 7.54 (d, 1H, J = 7.8 Hz) |

| Example | Intermediates | Structure & name | Characterization |
|---|---|---|---|
| 8 | 2 & 21 | 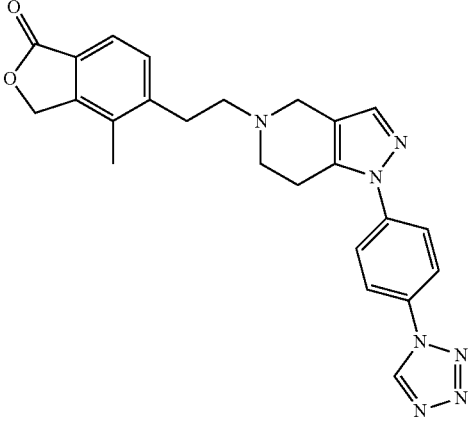 [SMILES: Cc1c(CCN2CCc3c(cnn3-c3ccc(-n4cnnn4)cc3)C2)ccc2c1COC2=O]<br>4-methyl-5-(2-{1-[4-(1H-tetrazol-1-yl)phenyl]-1,4,6,7-tetrahydro-5H-pyrazolo[4,3-c]pyridin-5-yl}ethyl)-2-benzofuran-1(3H)-one | LC/MS [M + H]$^+$ = 442.3 |
| 9 | 2 & 44 | 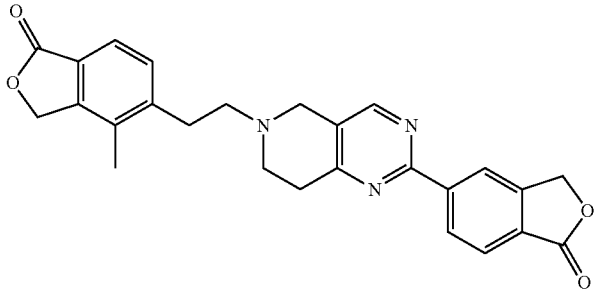 [SMILES: Cc1c(CCN2CCc3nc(-c4ccc5c(c4)COC5=O)ncc3C2)ccc2c1COC2=O]<br>4-methyl-5-{2-[2-(1-oxo-1,3-dihydro-2-benzofuran-5-yl)-7,8-dihydropyrido[4,3-d]pyrimidin-6(5H)-yl]ethyl}-2-benzofuran-1(3H)-one | LC/MS [M + H]$^+$ = 442.1 |
| 10 | 2 & 46 | 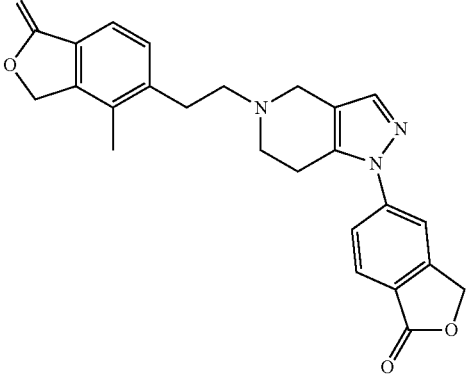<br>4-methyl-5-{2-[1-(1-oxo-1,3-dihydro-2-benzofuran-5-yl)-1,4,6,7-tetrahydro-5H-pyrazolo[4,3-c]pyridin-5-yl]ethyl}-2-benzofuran-1(3H)-one | LC/MS [M + H]$^+$ = 430.1 |

| Example | Intermediates | Structure & name | Characterization |
|---|---|---|---|
| 11 | 2 & 47 | 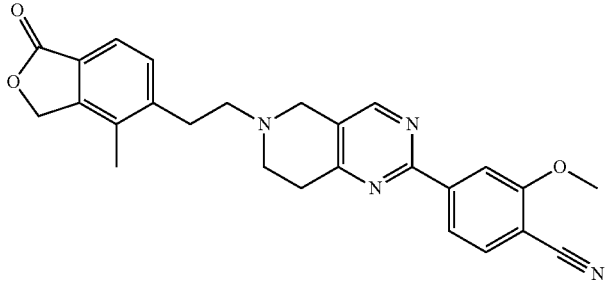 [SMILES: COc1cc(-c2ncc3c(n2)CCN(CCc2ccc4c(c2C)COC4=O)C3)ccc1C#N]<br>2-methoxy-4-{6-[2-(4-methyl-1-oxo-1,3-dihydro-2-benzofuran-5-yl)ethyl]-5,6,7,8-tetrahydropyrido[4,3-d]pyrimidin-2-yl}benzonitrile | $^1$H-NMR (400 MHz, CDCl$_3$) δ ppm 8.53 (s, 1H), 8.13-8.11 (m, 2H), 7.75 (d, 1H, J = 7.8 Hz), 7.68 (d, 1H, J = 7.8), 7.42 (d, 1H, J = 7.8), 5.28 (s, 2H), 4.08 (s, 2H), 3.81 (s, 2H), 3.15-3.08 (m, 5H), 2.87-2.84 (m, 2H), 2.36 (s, 3H) |
| 12 | 2 & 12 | 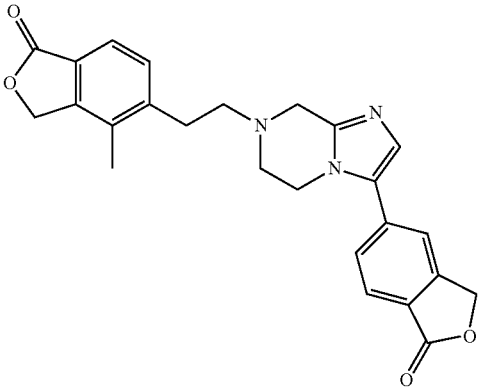 [SMILES: Cc1c(CCN2CCn3c(-c4ccc5c(c4)COC5=O)cnc3C2)ccc2c1COC2=O]<br>4-methyl-5-{2-[3-(1-oxo-1,3-dihydro-2-benzofuran-5-yl)-5,6-dihydroimidazo[1,2-a]pyrazin-7(8H)-yl]ethyl}-2-benzofuran-1(3H)-one | LC/MS [M + H]$^+$ = 430.3 |
| 13 | 2 & 13 | 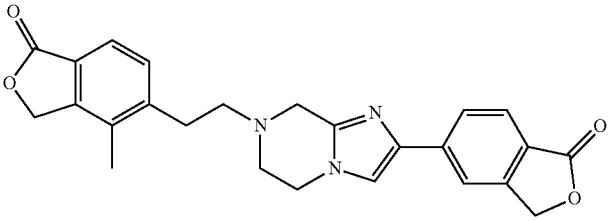 [SMILES: Cc1c(CCN2CCn3cc(-c4ccc5c(c4)COC5=O)nc3C2)ccc2c1COC2=O]<br>4-methyl-5-{2-[2-(1-oxo-1,3-dihydro-2-benzofuran-5-yl)-5,6-dihydroimidazo[1,2-a]pyrazin-7(8H)-yl]ethyl}-2-benzofuran-1(3H)-one | LC/MS [M + H]$^+$ = 430.3 |

-continued

| Example | Intermediates | Structure & name | Characterization |
|---|---|---|---|
| 14 | 2 & 22 | 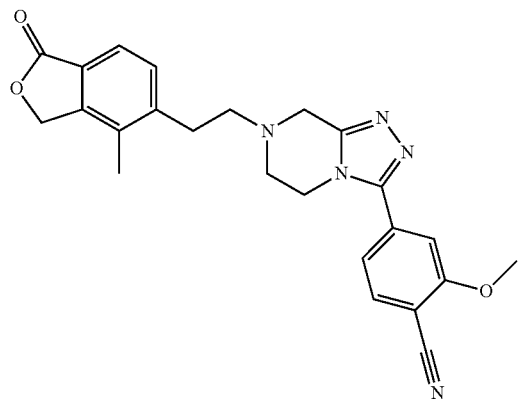 [SMILES: COc1cc(-c2nnc3n2CCN(CCc2ccc4c(c2C)COC4=O)C3)ccc1C#N]<br>2-methoxy-4-{7-[2-(4-methyl-1-oxo-1,3-dihydro-2-benzofuran-5-yl)ethyl]-5,6,7,8-tetrahydro[1,2,4]triazolo[4,3-a]pyrazin-3-yl}benzonitrile | LC/MS [M + H]⁺ = 430.4 |
| 15 | 2 & 52 | 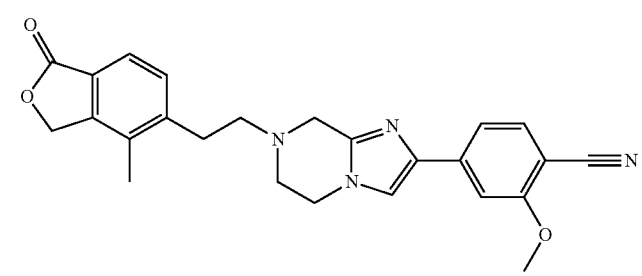 [SMILES: COc1cc(-c2cn3c(n2)CN(CCc2ccc4c(c2C)COC4=O)CC3)ccc1C#N]<br>2-methoxy-4-{7-[2-(4-methyl-1-oxo-1,3-dihydro-2-benzofuran-5-yl)ethyl]-5,6,7,8-tetrahydroimidazo[1,2-a]pyrazin-2-yl}benzonitrile | LC/MS [M + H]⁺ = 429.3 |
| 16 | 2 & 26 | 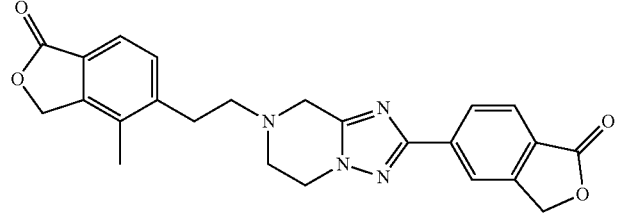 [SMILES: Cc1c(CCN2CCn3nc(-c4ccc5c(c4)COC5=O)nc3C2)ccc2c1COC2=O]<br>4-methyl-5-{2-[2-(1-oxo-1,3-dihydro-2-benzofuran-5-yl)-5,6-dihydro[1,2,4]triazolo[1,5-a]pyrazin-7(8H)-yl]ethyl}-2-benzofuran-1(3H)-one | LC/MS [M + H]⁺ = 431.1 |
| 17 | 2 & 27 | 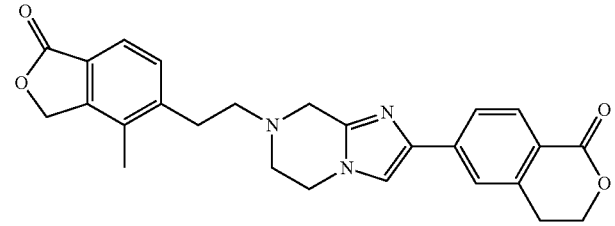 [SMILES: Cc1c(CCN2CCn3cc(-c4ccc5c(c4)CCOC5=O)nc3C2)ccc2c1COC2=O]<br>6-{7-[2-(4-methyl-1-oxo-1,3-dihydro-2-benzofuran-5-yl)ethyl]-5,6,7,8-tetrahydroimidazo[1,2-a]pyrazin-2-yl}-3,4-dihydro-1H-isochromen-1-one | LC/MS [M + H]⁺ = 444.3 |

| Example | Intermediates | Structure & name | Characterization |
|---|---|---|---|
| 18 | 2 & 15 | 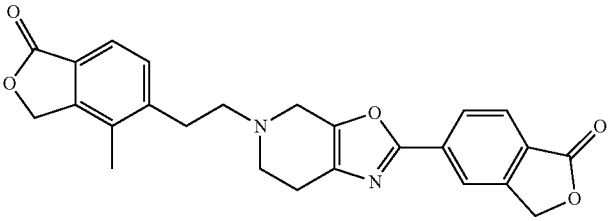 [SMILES: Cc1c(CCN2CCc3nc(-c4ccc5c(c4)COC5=O)oc3C2)ccc2c1COC2=O]<br>4-methyl-5-{2-[2-(1-oxo-1,3-dihydro-2-benzofuran-5-yl)-6,7-dihydro[1,3]oxazolo[5,4-c]pyridin-5(4H)-yl]ethyl}-2-benzofuran-1(3H)-one | LC/MS [M + H]⁺ = 431.2 |
| 19 | 7 & 13 | 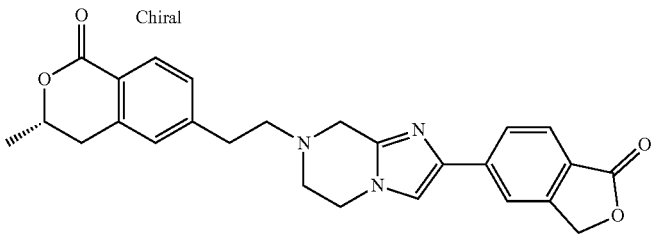 [SMILES: C[C@H]1Cc2cc(CCN3CCn4cc(-c5ccc6c(c5)COC6=O)nc4C3)ccc2C(=O)O1] Chiral<br>(3S)-3-methyl-6-{2-[2-(1-oxo-1,3-dihydro-2-benzofuran-5-yl)-5,6-dihydroimidazo[1,2-a]pyrazin-7(8H)-yl]ethyl}-3,4-dihydro-1H-isochromen-1-one | LC/MS [M + H]⁺ = 444.2 |
| 20 | 3 & 13 | 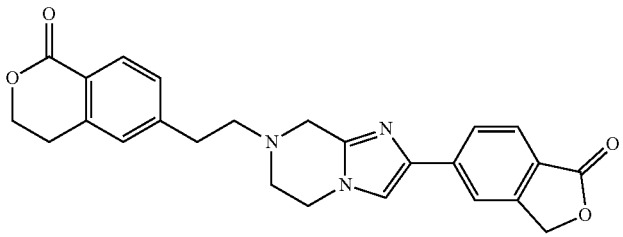 [SMILES: O=C1OCCc2cc(CCN3CCn4cc(-c5ccc6c(c5)COC6=O)nc4C3)ccc21]<br>6-{2-[2-(1-oxo-1,3-dihydro-2-benzofuran-5-yl)-5,6-dihydroimidazo[1,2-a]pyrazin-7(8H)-yl]ethyl}-3,4-dihydro-1H-isochromen-1-one | LC/MS [M + H]⁺ = 430.2 |
| 21 | 2 & 28 | 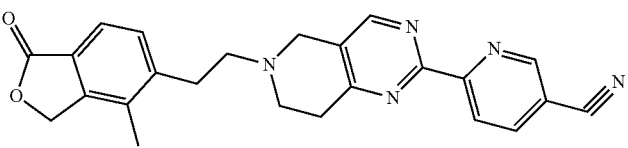<br>6-{6-[2-(4-methyl-1-oxo-1,3-dihydro-2-benzofuran-5-yl)ethyl]-5,6,7,8-tetrahydropyrido[4,3-d]pyrimidin-2-yl}pyridine-3-carbonitrile | $^1$H-NMR (400 MHz, CDCl$_3$) δ ppm 9.00 (s, 1 H), 8.56-8.60 (m, 2 H), 8.05 (d, J = 8.4 Hz, 1 H), 7.62 (d, J = 8.0 Hz, 1 H), 7.21-7.22 (m, 1 H), 5.18 (s, 2 H), 3.77 (s, 2 H), 3.13-3.15 (m, 2H), 2.93-3.12 (m, 4H), 2.76-2.80 (m, 2H), 2.27 (s, 3 H). |
| 22 | 2 & 32 | 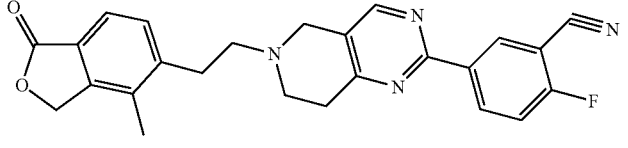<br>2-fluoro-5-{6-[2-(4-methyl-1-oxo-1,3-dihydro-2-benzofuran-5-yl)ethyl]-5,6,7,8-tetrahydropyrido[4,3-d]pyrimidin-2-yl}benzonitrile | $^1$H-NMR (400 MHz, CDCl$_3$) δ ppm 8.65-8.67 (m, 2 H), 8.46 (s, 1 H), 7.69-7.71 (m, 1 H), 7.24-7.39 (m, 2 H), 5.24 (s, 2 H), 3.76 (s, 2 H), 3.04-3.16 (m, 4 H), 2.87-2.98 (m, 2H), 2.79-2.83 (m, 2H), 2.32 (s, 3 H). |

| Example | Intermediates | Structure & name | Characterization |
|---|---|---|---|
| 23 | 2 & 33 | 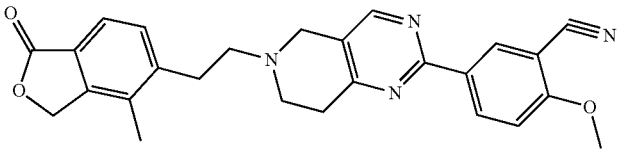<br>2-methoxy-5-{6-[2-(4-methyl-1-oxo-1,3-dihydro-2-benzofuran-5-yl)ethyl]-5,6,7,8-tetrahydropyrido[4,3-d]pyrimidin-2-yl}benzonitrile | ¹H-NMR (400 MHz, CDCl₃) δ ppm 8.52-8.64 (m, 3 H), 7.67-7.69 (m, 1 H), 7.27-7.29 (m, 1 H), 7.00-7.03 (m, 1 H), 5.19 (s, 2 H), 4.38-4.44 (m, 2 H), 3.96 (s, 3 H), 3.55-3.68 (m, 2 H), 3.27-3.43 (m, 6 H), 2.35 (s, 3 H). |
| 24 | 2 & 23 | 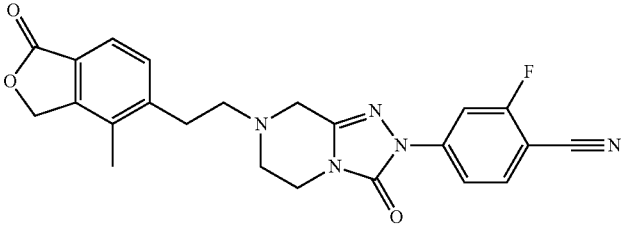 [SMILES: Cc1c(CCN2CCn3c(nn(-c4ccc(C#N)c(F)c4)c3=O)C2)ccc2c1COC2=O]<br>2-fluoro-4-{7-[2-(4-methyl-1-oxo-1,3-dihydro-2-benzofuran-5-yl)ethyl]-3-oxo-5,6,7,8-tetrahydro[1,2,4]triazolo[4,3-a]pyrazin-2(3H)-yl}benzonitrile | LC/MS [M + H]⁺ = 434.2 |
| 25 | 2 & 17 | 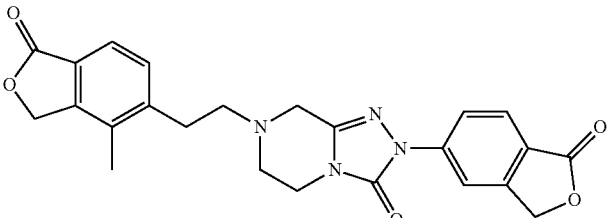<br>7-[2-(4-methyl-1-oxo-1,3-dihydro-2-benzofuran-5-yl)ethyl]-2-(1-oxo-1,3-dihydro-2-benzofuran-5-yl)-5,6,7,8-tetrahydro[1,2,4]triazolo[4,3-a]pyrazin-3(2H)-one | LC/MS [M + H]⁺ = 447.2 |
| 26 | 2 & 30 | 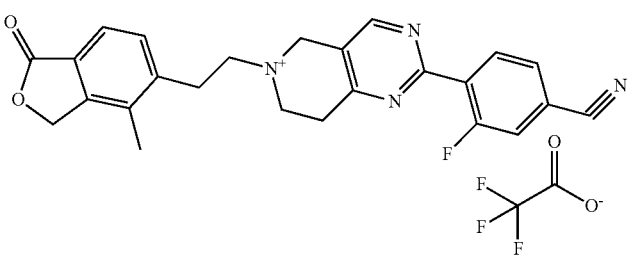<br>2-(4-cyano-2-fluorophenyl)-6-[2-(4-methyl-1-oxo-1,3-dihydro-2-benzofuran-5-yl)ethyl]-5,6,7,8-tetrahydropyrido[4,3-d]pyrimidin-6-ium | ¹H-NMR (400 MHz, CDCl₃) δ ppm 8.62-8.65 (m, 1 H), 8.14-8.20 (m, 1 H), 7.67-7.69 (m, 1 H), 7.51-7.53 (m, 1 H), 7.43-7.47 (m, 1 H), 7.27-7.29 (m, 1 H), 5.19 (s, 2 H), 4.44 (s, 2 H), 3.61(s, 2 H), 3.86-3.43 (m, 2H), 3.27 (s, 4 H), 2.27 (s, 3 H). |
| 27 | 2 & 31 | 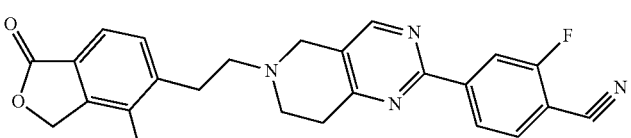<br>2-fluoro-4-{6-[2-(4-methyl-1-oxo-1,3-dihydro-2-benzofuran-5-yl)ethyl]-5,6,7,8-tetrahydropyrido[4,3-d]pyrimidin-2-yl}benzonitrile | ¹H-NMR (400 MHz, CDCl₃) δ ppm 8.45 (s, 1 H), 8.23-8.30 (m, 2 H), 7.63-7.67 (m, 2 H), 7.31-7.33 (m, 1 H), 5.19 (s, 2 H), 3.72 (s, 2 H), 2.90-3.06 (m, 6 H), 2.74-2.78 (m, 2 H), 2.27 (s, 3 H). |

-continued

| Example | Intermediates | Structure & name | Characterization |
|---|---|---|---|
| 28 | 2 & 34 | 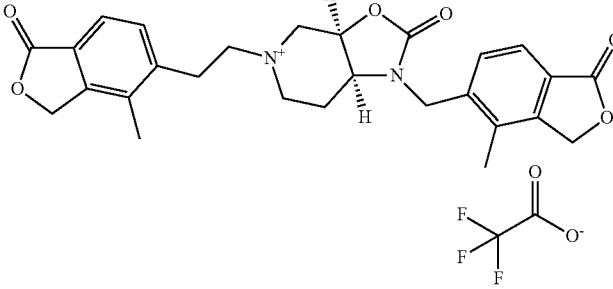<br>(3aR,7aS)-5-[2-(4-methyl-1-oxo-1,3-dihydro-2-benzofuran-5-yl)ethyl]-1-[(4-methyl-1-oxo-1,3-dihydro-2-benzofuran-5-yl)methyl]-2-oxooctahydro[1,3]oxazolo[5,4-c]pyridin-5-ium | $^1$H-NMR (400 MHz, MeOD) δ ppm 7.66-7.72 (m, 2H), 7.58 (d, J = 7.8 Hz, 1H), 7.45 (d, J = 7.8 Hz, 1H), 5.36 (d, J = 12.5 Hz, 4H), 4.42 (d, J = 15.6 Hz, 1H), 4.15-4.22 (m, 2H), 3.61-3.74 (m, 2H), 3.36-3.48 (m, 3H), 3.08-3.24 (m, 3H), 2.34-2.37 (m, 6H), 2.06-2.09 (m, 2H), 1.65-1.77 (m, 1H). |
| 29 | 2 & 35 | 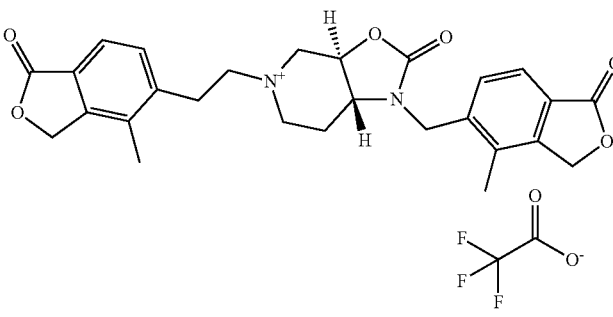<br>(3aR,7aR)-5-[2-(4-methyl-1-oxo-1,3-dihydro-2-benzofuran-5-yl)ethyl]-1-[(4-methyl-1-oxo-1,3-dihydro-2-benzofuran-5-yl)methyl]-2-oxooctahydro[1,3]oxazolo[5,4-c]pyridin-5-ium | $^1$H-NMR (400 MHz, MeOD) δ ppm 7.64-7.70 (m, 2H), 7.56 (d, J = 7.8 Hz, 1H), 7.43 (d, J = 7.8 Hz, 1H), 5.36 (d, J = 12.5 Hz, 4H), 4.42 (d, J = 15.6 Hz, 1H), 4.15-4.22 (m, 2H), 3.61-3.74 (m, 2H), 3.36-3.48 (m, 3H), 3.08-3.24 (m, 3H), 2.34-2.37 (m, 6H), 2.06-2.09 (m, 2H), 1.65-1.77 (m, 1H). |
| 30 | 2 & 19 | 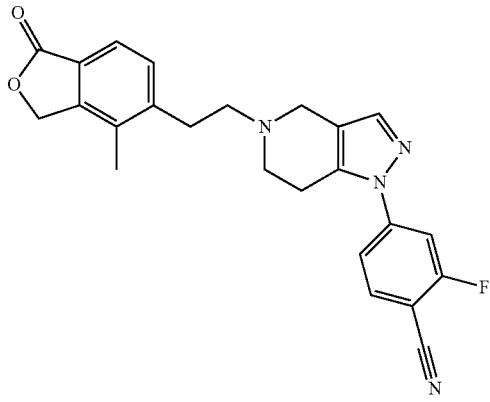 [SMILES: Cc1c(CCN2CCc3c(cnn3-c3ccc(C#N)c(F)c3)C2)ccc2c1COC2=O]<br>2-fluoro-4-(5-(2-(4-methyl-1-oxo-1,3-dihydroisobenzofuran-5-yl)ethyl)-4,5,6,7-tetrahydro-1H-pyrazolo[4,3-c]pyridin-1-yl)benzonitrile | |

Example 31

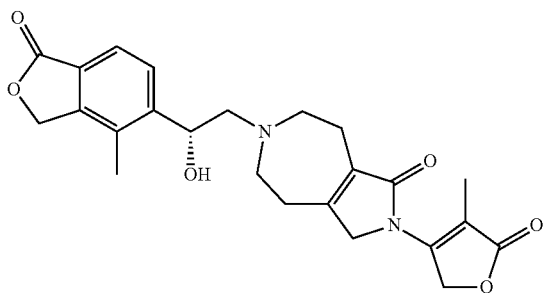 [SMILES: CC1=C(N2CC3=C(CCN(C[C@H](O)c4ccc5c(c4C)COC5=O)CC3)C2=O)COC1=O]

(R)-6-(2-Hydroxy-2-(4-methyl-1-oxo-1,3-dihydroisobenzofuran-5-yl)ethyl)-2-(4-methyl-5-oxo-2,5-dihydrofuran-3-yl)-2,3,5,6,7,8-hexahydropyrrolo[3,4-d]azepin-1(4H)-one To 2-(4-methyl-5-oxo-2,5-dihydrofuran-3-yl)-2,3,5,6,7,8-hexahydropyrrolo[3,4-d]azepin-1(4H)-one (25 mg, 0.101 mmol) in ethanol (0.50 mL) was added (R)-4-methyl-5-(oxiran-2-yl)isobenzofuran-1(3H)-one (28.7 mg, 0.151 mmol). The reaction mixture was heated at 90° C. 16 h. The reaction mixture was evaporated for purification by prep-TLC (2×2000 µM plates, 8% MeOH/EtOAc as eluent) to provide the title compound as a free base. LC/LC/MS: [(M+1)]$^+$=439

$^1$H NMR (500 MHz, CDCl$_3$) δ 7.16 (ABq, J=12.2 Hz, Δδ=8.1 Hz, 2H), 5.28 (s, 2H), 5.28-5.20 (m, 2H), 5.06 (dd, J=10.0, 3.1 Hz, 1H), 4.44 (s, 2H), 3.11-2.90 (m, 6H), 2.66-2.48 (m, 4H), 2.27 (s, 3H), 2.00 (s, 3H)

| Example | Intermediate | Structure & name | Characterization |
|---|---|---|---|
| 32 | 5 & 44 | 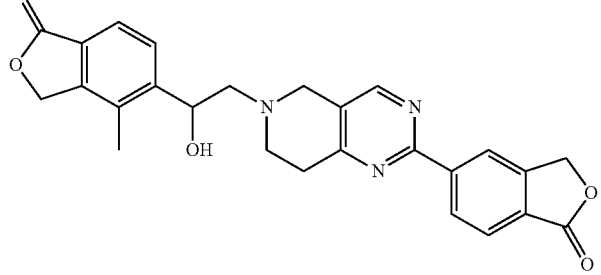<br>5-{1-hydroxy-2-[2-(1-oxo-1,3-dihydro-2-benzofuran-5-yl)-7,8-dihydropyrido[4,3-d]pyrimidin-6(5H)-yl]ethyl}-4-methyl-2-benzofuran-1(3H)-one | LC/MS [M + H]$^+$ = 458.3 |
| 33 | 5 & 46 | 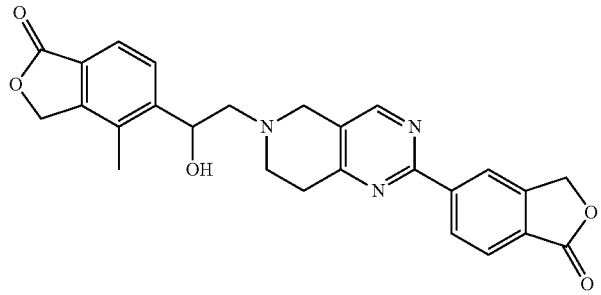<br>5-{1-hydroxy-2-[1-(1-oxo-1,3-dihydro-2-benzofuran-5-yl)-1,4,6,7-tetrahydro-5H-pyrazolo[4,3-c]pyridin-5-yl]ethyl}-4-methyl-2-benzofuran-1(3H)-one | LC/MS [M + H]$^+$ = 446.3 |

| Example | Intermediate | Structure & name | Characterization |
|---|---|---|---|
| 34 | 5 & 13 | 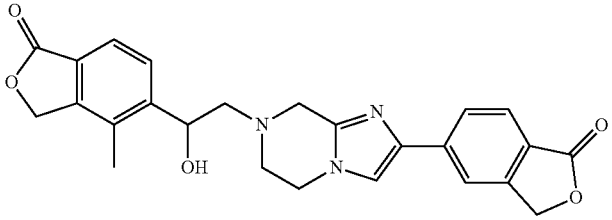 [SMILES: Cc1c(C(O)CN2CCn3cc(-c4ccc5c(c4)COC5=O)nc3C2)ccc2c1COC2=O]<br>5-{1-hydroxy-2-[2-(1-oxo-1,3-dihydro-2-benzofuran-5-yl)-5,6-dihydroimidazo[1,2-a]pyrazin-7(8H)-yl]ethyl}-4-methyl-2-benzofuran-1(3H)-one | LC/MS [M + H]$^+$ = 446.3 |
| 35 | 5 & 52 | 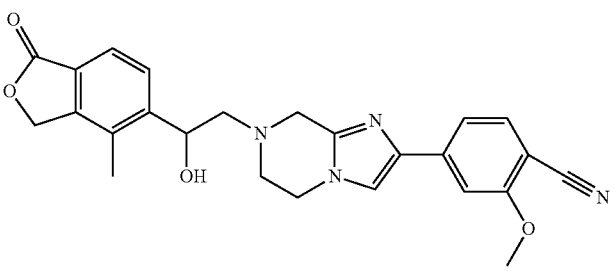 [SMILES: COc1cc(-c2cn3c(n2)CN(CC(O)c2ccc4c(c2C)COC4=O)CC3)ccc1C#N]<br>4-{7-[2-hydroxy-2-(4-methyl-1-oxo-1,3-dihydro-2-benzofuran-5-yl)ethyl]-5,6,7,8-tetrahydroimidazo[1,2-a]pyrazin-2-yl}-2-methoxybenzonitrile | LC/MS [M + H]$^+$ = 445.3 |
| 36 | 5 & 23 | 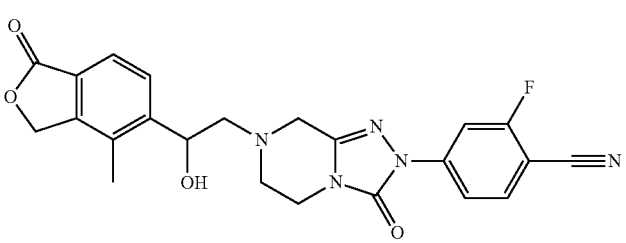 [SMILES: Cc1c(C(O)CN2CCn3c(nn(-c4ccc(C#N)c(F)c4)c3=O)C2)ccc2c1COC2=O]<br>2-fluoro-4-{7-[2-hydroxy-2-(4-methyl-1-oxo-1,3-dihydro-2-benzofuran-5-yl)ethyl]-3-oxo-5,6,7,8-tetrahydro[1,2,4]triazolo[4,3-a]pyrazin-2(3H)-yl}benzonitrile. | LC/MS [M + H]$^+$ = 449.9 |
| 37 | 5 & 17 | 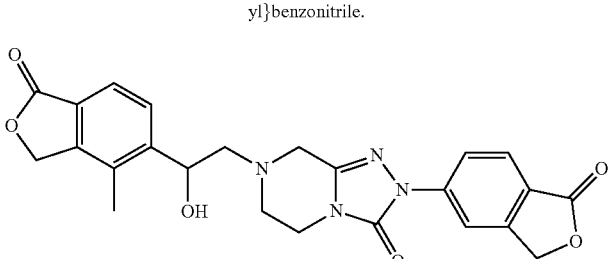<br>7-[2-hydroxy-2-(4-methyl-1-oxo-1,3-dihydro-2-benzofuran-5-yl)ethyl]-2-(1-oxo-1,3-dihydro-2-benzofuran-5-yl)-5,6,7,8-tetrahydro[1,2,4]triazolo[4,3-a]pyrazin-3(2H)-one | LC/MS [M + Na]$^+$ = 485.1 |
| 38 | 5 & 31 | 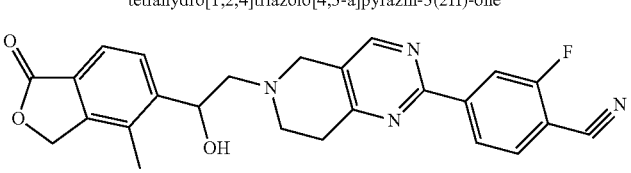<br>2-fluoro-4-{6-[2-hydroxy-2-(4-methyl-1-oxo-1,3-dihydro-2-benzofuran-5-yl)ethyl]-5,6,7,8-tetrahydropyrido[4,3-d]pyrimidin-2-yl}benzonitrile | |

-continued

| Example | Intermediate | Structure & name | Characterization |
|---|---|---|---|
| 39 | 5 & 29 | 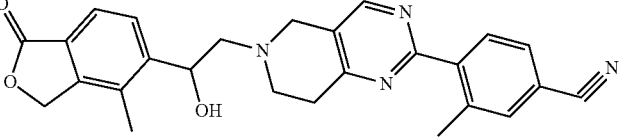<br>4-{6-[2-hydroxy-2-(4-methyl-1-oxo-1,3-dihydro-2-benzofuran-5-yl)ethyl]-5,6,7,8-tetrahydropyrido[4,3-d]pyrimidin-2-yl}-3-methylbenzonitrile | |
| 40 | 5 & 28 | 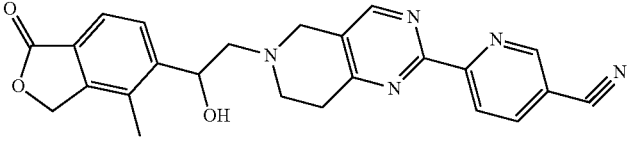 [SMILES: Cc1c(C(O)CN2CCc3nc(-c4ccc(C#N)cn4)ncc3C2)ccc2c1COC2=O]<br>6-{6-[2-hydroxy-2-(4-methyl-1-oxo-1,3-dihydro-2-benzofuran-5-yl)ethyl]-5,6,7,8-tetrahydropyrido[4,3-d]pyrimidin-2-yl}pyridine-3-carbonitrile | |
| 41 | 5 & 30 | 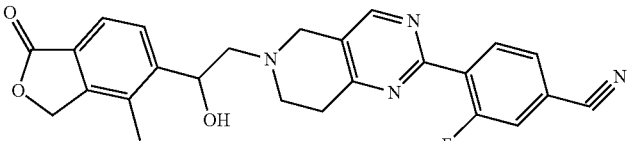<br>3-fluoro-4-{6-[2-hydroxy-2-(4-methyl-1-oxo-1,3-dihydro-2-benzofuran-5-yl)ethyl]-5,6,7,8-tetrahydropyrido[4,3-d]pyrimidin-2-yl}benzonitrile | |
| 42 | 5 & 38 | 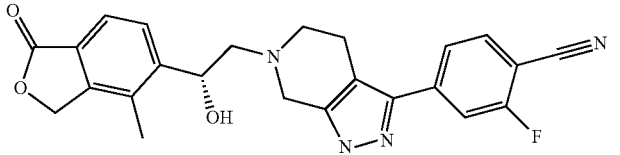 [SMILES: Cc1c([C@@H](O)CN2CCc3c(-c4ccc(C#N)c(F)c4)n[nH]c3C2)ccc2c1COC2=O]<br>3-(4-cyano-3-fluorophenyl)-6-((R)-2-hydroxy-2-(4-methyl-1-oxo-1,3-dihydroisobenzofuran-5-yl)ethyl)-4,5,6,7-tetrahydro-1H-pyrazolo[3,4-c]pyridine | LC/MS [M + H]$^+$ = 433.1 |
| 43 | 5 & 39 | 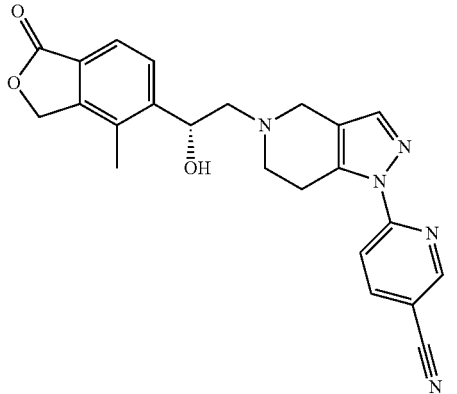 [SMILES: Cc1c([C@@H](O)CN2CCc3c(cnn3-c3ccc(C#N)cn3)C2)ccc2c1COC2=O]<br>6-{5-[(2R)-2-hydroxy-2-(4-methyl-1-oxo-1,3-dihydro-2-benzofuran-5-yl)ethyl]-4,5,6,7-tetrahydro-1H-pyrazolo[4,3-c]pyridin-1-yl}pyridine-3-carbonitrile | LC/MS [M + H]$^+$ = 416.0 |

| Example | Intermediate | Structure & name | Characterization |
|---|---|---|---|
| 44 | 5 & 51 | 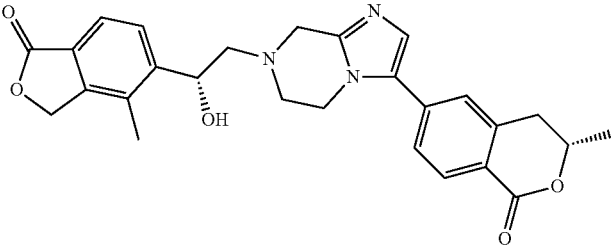 [SMILES: Cc1c([C@@H](O)CN2CCn3c(-c4ccc5c(c4)C[C@H](C)OC5=O)cnc3C2)ccc2c1COC2=O]<br>(3S)-6-{7-[(2R)-2-hydroxy-2-(4-methyl-1-oxo-1,3-dihydro-2-benzofuran-5-yl)ethyl]-5,6,7,8-tetrahydroimidazo[1,2-a]pyrazin-3-yl}-3-methyl-3,4-dihydro-1H-isochromen-1-one | LC/MS [M + H]$^+$ = 474.1 |
| 45 | 5 & 25 | 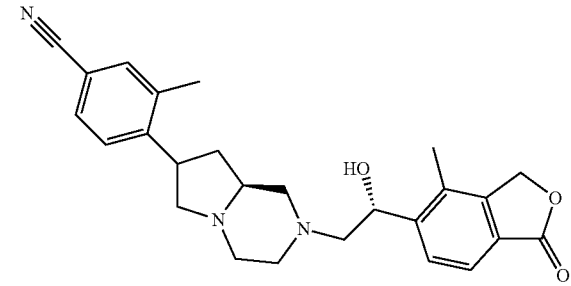 [SMILES: Cc1cc(C#N)ccc1C1C[C@H]2CN(C[C@H](O)c3ccc4c(c3C)COC4=O)CCN2C1]<br>4-{(8aS)-2-[(2R)-2-hydroxy-2-(4-methyl-1-oxo-1,3-dihydro-2-benzofuran-5-yl)ethyl]octahydropyrrolo[1,2-a]pyrazin-7-yl}-3-methylbenzonitrile | LC/MS [M + H]$^+$ = 432.1 |
| 46 | 5 & 24 | 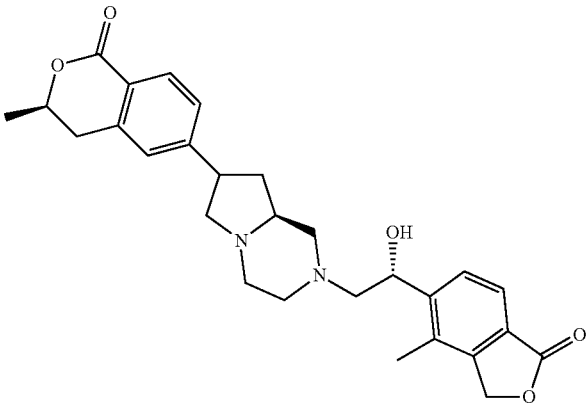 [SMILES: Cc1c([C@@H](O)CN2CCN3CC(c4ccc5c(c4)C[C@@H](C)OC5=O)C[C@H]3C2)ccc2c1COC2=O]<br>(3R)-6-{(8aS)-2-[(2R)-2-hydroxy-2-(4-methyl-1-oxo-1,3-dihydro-2-benzofuran-5-yl)ethyl]octahydropyrrolo[1,2-a]pyrazin-7-yl}-3-methyl-3,4-dihydro-1H-isochromen-1-one | LC/MS [M + H]$^+$ = 477.2 |

| Example | Intermediate | Structure & name | Characterization |
|---|---|---|---|
| 47 | 5 & 40 | 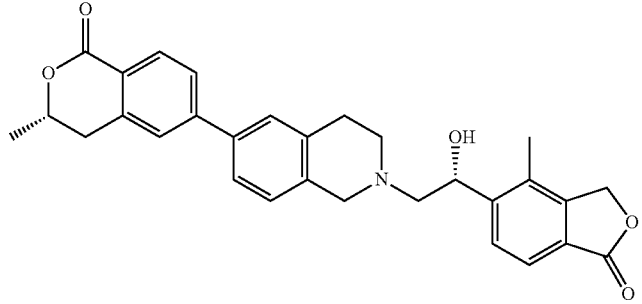 [SMILES: Cc1c([C@@H](O)CN2CCc3cc(-c4ccc5c(c4)C[C@H](C)OC5=O)ccc3C2)ccc2c1COC2=O]<br>2-[(2R)-2-hydroxy-2-(4-methyl-1-oxo-1,3-dihydro-2-benzofuran-5-yl)ethyl]-6-[(3S)-3-methyl-1-oxo-3,4-dihydro-1H-isochromen-6-yl]-1,2,3,4-tetrahydroisoquinoline | LC/MS [M + H]⁺ = 484.2 |

The following Thallium Flux Assay was performed on each of the final product compounds in the Examples. When the final product of an Example was an HCl salt, the salt was run in the Assay.

Thallium Flux Assay

Cell Culture Conditions—

HEK293 cells stably expressing hROMK (hK$_{ir}$1.1) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL Calcium/Magnesium-free PBS. Add 5 mL of 1× trypsin (prepared in Ca/Mg Free PBS) to T-225 flask and return flask to 37° C./$CO_2$ incubator for 2-3 minutes. To dislodge the cell, gently bang the side of the flask with your hand. Triturate the cells completely and then transfer the cells to 25 mL complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D)—Lyophilized sample is kept at −20° C. Water soluble, 100× after solubilization in 1 mL water. Store at 4° C.
  FluxOR™ Chloride-free Buffer (Component E)—5× Concentrate
  Potassium sulfate ($K_2SO_4$) Concentrate (Component F)—125 mM in water. Store at 4° C.
  Thallium sulfate ($Tl_2SO_4$) Concentrate (Component G)—50 mM in water. Store at 4° C.
  DMSO (dimethyl sulfoxide, Component H)—1 mL (100%)

Reagent Preparation: FluxOR Working Solutions
  1000× FluxOR™ Reagent: Reconstitute a vial of component A in 100 μl DMSO; Mix well; Store 10 μl aliquots at −20° C.
  1× FluxOR™ Assay Buffer: Dilute Component B 10-fold with water; Adjust pH to 7.4 with Hepes/NaOH; Filter and store at 4° C.
  Probenecid/Assay Buffer: 100 mL of 1× FluxOR™ Assay Buffer; 1 mL of reconstituted component D; Store at 4° C.
  Loading Buffer (per microplate): 10 μl 1000× FluxOR™ Reagent; 100 μl component C; 10 mL Probenecid/Assay Buffer
  Compound Buffer (per microplate): 20 mL Probenecid/Assay Buffer; 0.3 mM ouabain (10 mM ouabain in water can be stored in amber bottle/aluminum foil at room temperature); Test compound
  1× FluxOR™ Chloride-Free Buffer: Prepare 1× working solution in water. Can be stored at room temperature
  Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use.

Assay Protocol—

The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 μl at 20,000 cells/well) in 384-well PDL coated Microplates
2. Allow cells to adhere overnight in humidified 37° C./10% $CO_2$ incubator
3. Completely remove cell growth media from microplate and replace with 25 μl loading buffer
4. Incubate Microplate at room temperature, protected form light, for 90 min
5. Remove loading buffer and replace with 25 μl 1× Assay Buffer±test compound.
6. Incubate microplate at room temperature, protected from light, for 30 min 7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—

The fluorescence intensity of wells containing 3 µM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—

Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1 µM.

Data collected for compounds in the Examples of the present invention using the Thallium Flux Assay are shown in Table 10 below. The data for Examples 2, 3, 4, 8, 9, 10, 15 and 32 were obtained using the $^{86}Rb^+$ Efflux Assay, described in WO2013/062892 at pages 79-80. These data points are marked in the data table with "(Rb)." All of the tested final product compounds in the Examples (diastereomeric mixtures and individual diastereomers) had $IC_{50}$ potencies less than 1 µM in the Thallium Flux Assay or the $^{86}Rb^+$ Efflux Assay.

TABLE 10

| Example No. | Thallium Flux $IC_{50}$ (µM) |
|---|---|
| 1 | 0.4771 |
| 2 | 0.3059 (Rb) |
| 3 | 0.5006 (Rb) |
| 4 | 0.3043 (Rb) |
| 5 | 0.0438 |
| 6 | 0.074 |
| 7 | 0.168 |
| 8 | 0.3799 (Rb) |
| 9 | 0.09614 (Rb) |
| 10 | 0.066 (Rb) |
| 11 | 0.08383 |
| 12 | 0.1239 |
| 13 | 0.1341 |
| 14 | 0.08504 |
| 15 | 0.1972 (Rb) |
| 16 | 0.08904 |
| 17 | 0.6541 |
| 18 | 0.07474 |
| 19 | 0.1983 |
| 20 | 0.1919 |
| 21 | 0.449 |
| 22 | 0.441 |
| 23 | 0.2078 |
| 24 | 0.1768 |
| 25 | 0.09278 |
| 26 | 0.3143 |
| 27 | 0.07015 |
| 28 | 0.113 |
| 29 | 0.201 |
| 30 | 0.02746 |
| 31 | 0.06401 |
| 32 | 0.06987 (Rb) |
| 33 | 0.067 |
| 34 | 0.09936 |
| 35 | 0.1536 |
| 36 | 0.163 |

TABLE 10-continued

| Example No. | Thallium Flux $IC_{50}$ (µM) |
|---|---|
| 37 | 0.2914 |
| 38 | 0.082 |
| 39 | 0.3372 |
| 40 | 0.1547 |
| 41 | 0.463 |
| 42 | 0.1729 |
| 43 | 0.5916 |
| 44 | 0.3014 |
| 45 | 0.1311 |
| 46 | 0.08143 |
| 47 | 0.2486 |

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I

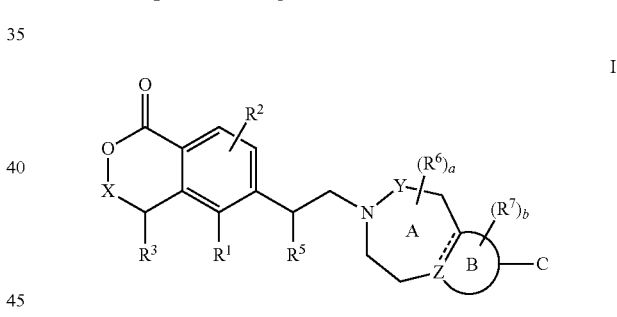

or a pharmaceutically acceptable salt thereof wherein:

X is $CHR^4$ or a bond;

$R^1$ and $R^2$ are each independently of one another H, —OH, halogen, —$C_{1-4}$alkyl optionally substituted with 1-9 halogens, —$C_{3-4}$cycloalkyl, or —$OC_{1-4}$alkyl optionally substituted with 1-9 halogens;

$R^3$ is H or —$C_{1-4}$alkyl;

$R^4$ is H, —$C_{1-4}$alkyl, or —$OC_{1-4}$alkyl;

R is —H, —OH, oxo, fluoro or —$C_{1-4}$alkyl which is optionally substituted with 1-9 halogens;

Y is —$CH_2$— or a bond;

the dashed line between rings A and B represents an optional double bond where rings A and B are fused;

A is a 6 or 7-membered heterocyclic ring having 1 or 2 —N-atoms and optionally 1 double bond;

Z is a nitrogen atom or a carbon atom, where the carbon atom is unsubstituted when the A and B rings are fused by a double bond, or the carbon atom is substituted with —H when the A and B rings are fused by a single bond;

$R^6$ represents optional substituent groups on ring A which are each independently selected from the group consisting of —$C_{1-3}$alkyl optionally substituted with 1-7 halogens, and —$OC_{1-3}$alkyl optionally substituted with 1-7 halogens;

$R^7$ represents optional substituent groups on ring B which are each independently selected from the group consisting of -halogen, —$C_{1-3}$alkyl optionally substituted with 1-7 halogens, and —$OC_{1-3}$alkyl optionally substituted with 1-7 halogens a and b are each independently 0 or an integer from 1-3;

B is selected from phenyl, pyrimidine, pyrazole, imidazole, imidazoline, 1,2,4-triazole, 1,2,4-triazolone, 1,3-oxazole, oxazolidinone, pyrrolidine, pyridine, pyrazine, pyridazine, piperidine, isoxazole, and pyrrolidinone optionally having a double bond;

C is a cyclic or bicyclic group selected from
  (a) phenyl substituted with one group —CN or -tetrazole and optionally with 1-3 groups independently selected from halogen, —$C_{1-3}$alkyl optionally substituted with 1-7 halogens, and —$OC_{1-3}$alkyl optionally substituted with 1-7 halogens;
  (b) pyridyl, pyrimidyl, pyrazinyl, pyridazolyl or thiazolyl substituted with one group —CN or -tetrazole, and optionally substituted with 1-3 groups independently selected from halogen, —$C_{1-3}$alkyl optionally substituted with 1-7 halogens, and —$OC_{1-3}$ alkyl optionally substituted with 1-7 halogens;

(c)

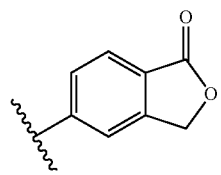

which is optionally substituted with 1-3 groups independently selected from halogen, —$C_{1-3}$ alkyl optionally substituted with 1-7 halogens, and —$OC_{1-3}$alkyl optionally substituted with 1-7 halogens;

(d)

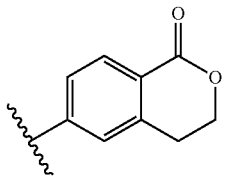 [SMILES: *c1ccc2c(c1)CCOC2=O]

which is optionally substituted with 1-3 groups independently selected from halogen, —$C_{1-3}$alkyl optionally substituted with 1-7 halogens, and —$OC_{1-3}$alkyl optionally substituted with 1-7 halogens; and (e)

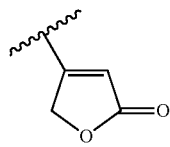

optionally substituted with 1-2 groups selected from —$CH_3$, —$OCH_3$, and halogen.

2. The compound of claim 1 having Formula II

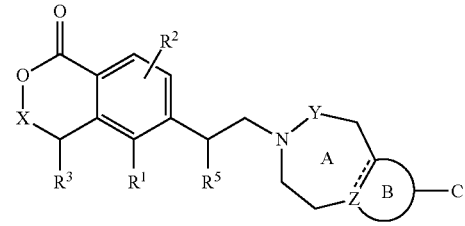

or a pharmaceutically acceptable salt thereof wherein:

X is $CHR^4$ or a bond;

$R^1$ and $R^2$ are each independently H, F, —$C_{1-2}$alkyl optionally substituted with 1-5 F, or —$OC_{1-2}$ alkyl optionally substituted with 1-5 F;

$R^3$ is H or —$C_{1-2}$alkyl;

$R^4$ is H or —$CH_3$;

$R^5$ is —H, —OH, F or —$CH_3$;

Y is —$CH_2$— or a bond;

the dashed line between rings A and B represents an optional double bond where rings A and B are fused;

A is a 6 or 7-membered heterocyclic ring having 1 or 2 —N-atoms and optionally one double bond;

Z is a nitrogen atom or a carbon atom, wherein the carbon atom is unsubstituted when the A and B rings are fused by a double bond, or the carbon atom is substituted with —H, when the A and B rings are fused by a single bond;

B is selected from phenyl, pyrimidine, pyrazole, imidazole, imidazoline, 1,2,4-triazole, 1,2,4-triazolone, 1,3-oxazole, oxazolidinone, pyrrolidine, pyridine, pyrazine, pyridazine, piperidine, isoxazole, and pyrrolidinone optionally having a double bond;

C is a cyclic or bicyclic group selected from
  (a) phenyl substituted with one group —CN or -tetrazole, and optionally with 1-2 groups independently selected from —$CH_3$, —$OCH_3$, and halogen;
  (b) pyridyl substituted with one group —CN or -tetrazole and optionally with 1-2 groups independently selected from —$CH_3$, —$OCH_3$, and halogen;

(c)

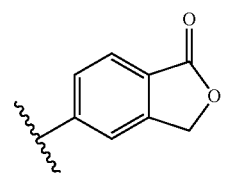

optionally substituted on the phenyl ring with 1-2 groups selected from —$CH_3$, —$OCH_3$, and halogen;

(d)

[structure: isochroman-1-one with wavy bond]

optionally substituted on the lactone ring with 1-2 groups selected from —CH₃, —OCH₃, and halogen; and (e)

[structure: furan-2(5H)-one with wavy bond]

optionally substituted with 1-2 groups selected from —CH₃, —OCH₃, and halogen.

3. The compound of claim 1, or a pharmaceutically acceptable salt thereof, wherein:
R¹ and R³ are each H or —CH₃;
R² is H;
R⁴ is H or —CH₃;
R⁵ is —H or —OH;
A is a 6 or 7-membered heterocyclic ring having 1 or 2 —N-atoms and optionally one double bond; and
C is a cyclic or bicyclic group selected from
   (a) phenyl substituted with one group —CN or -tetrazole, and optionally with 1-2 groups independently selected from —CH₃, —OCH₃, and halogen;
   (b) pyridyl substituted with one group —CN, and optionally with 1-2 groups independently selected from —CH₃, —OCH₃, and halogen;

(c)

[structure: isobenzofuran-1(3H)-one with wavy bond]

optionally substituted on the phenyl ring with one group selected from —CH₃, —OCH₃, and halogen;

[structure: isochroman-1-one with wavy bond]

optionally substituted on the lactone ring with one group —CH₃; and (e)

[structure: furan-2(5H)-one with wavy bond]

optionally substituted with one group —CH₃.

4. The compound of claim 1, or a pharmaceutically acceptable salt thereof, wherein Ring B is selected from phenyl, pyrimidine, pyrazole, imidazole, 1,2,4-triazole, 1,2,4-triazolone, 1,3-oxazole, oxazolidinone, pyrrolidine, and pyrrolidinone optionally having a double bond.

5. A compound having a structure selected from the structures below, or a pharmaceutically acceptable salt thereof:

[structures of four compounds]

103
-continued
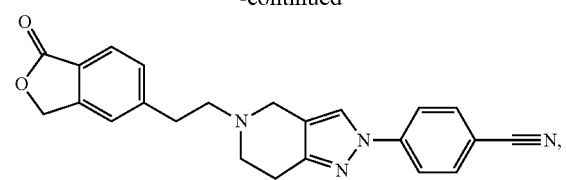
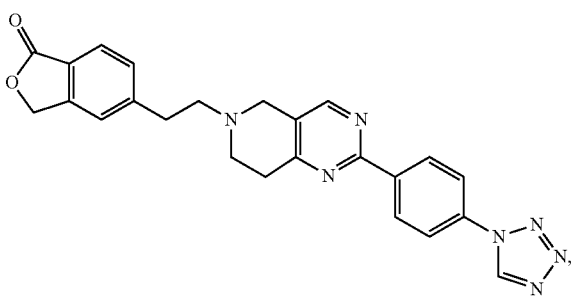
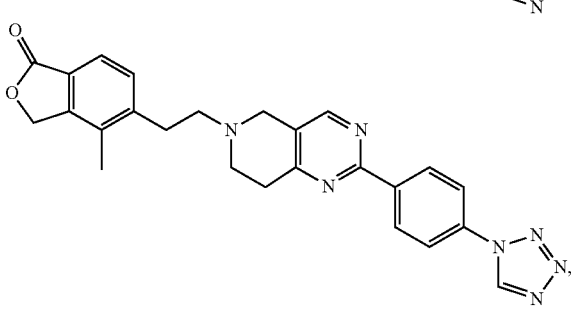
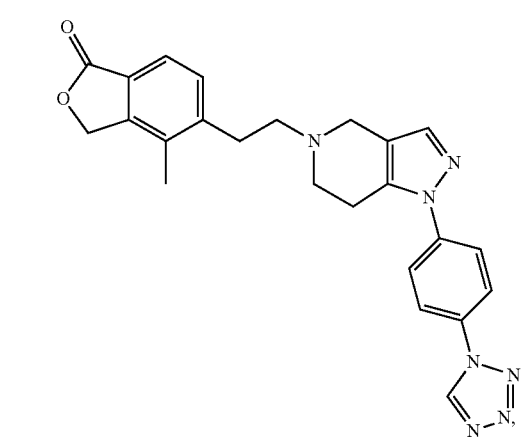
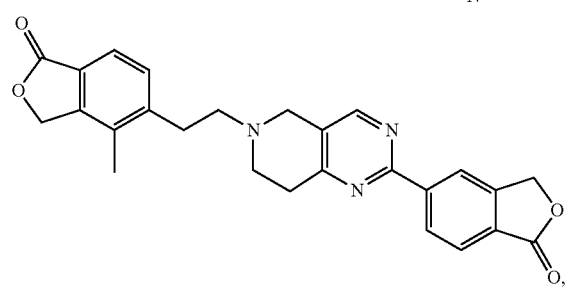
104
-continued
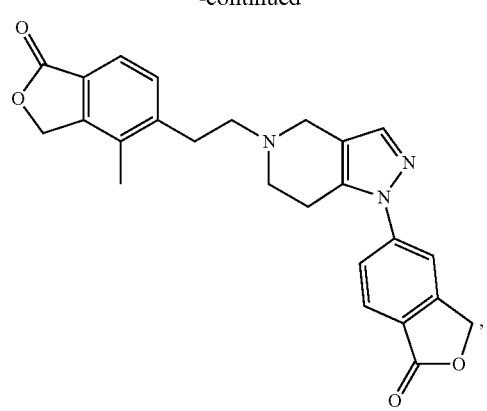
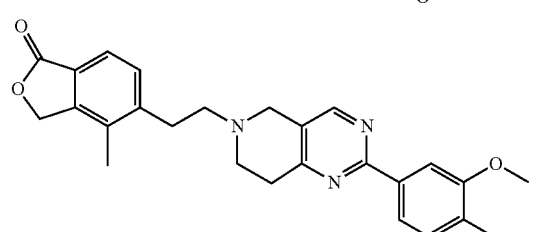
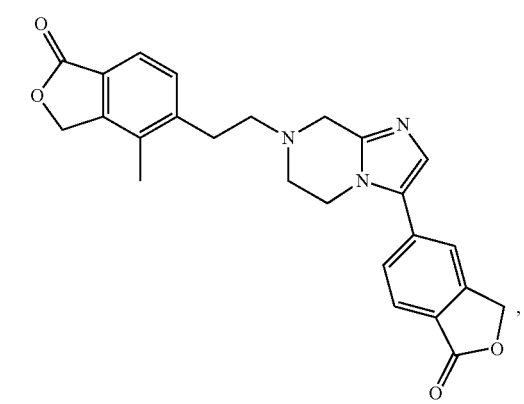
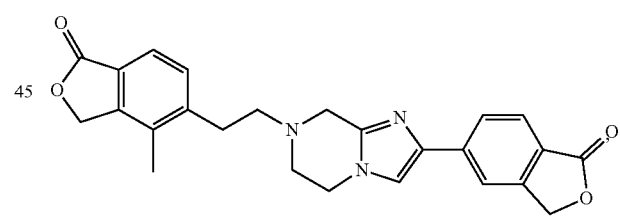
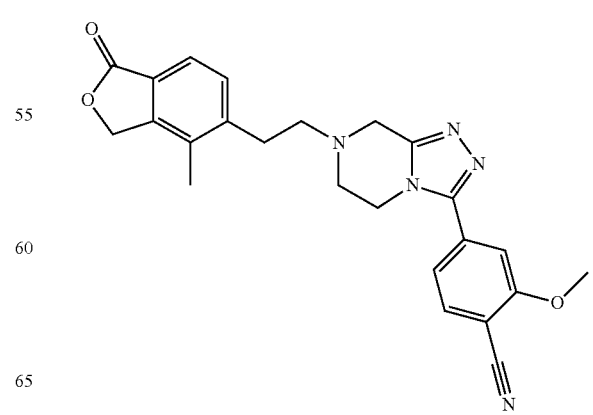

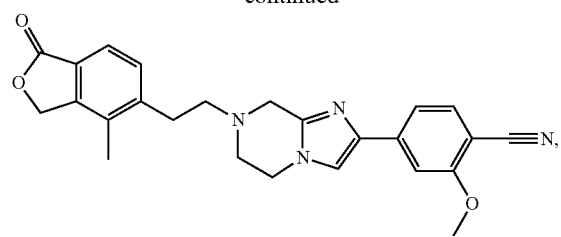
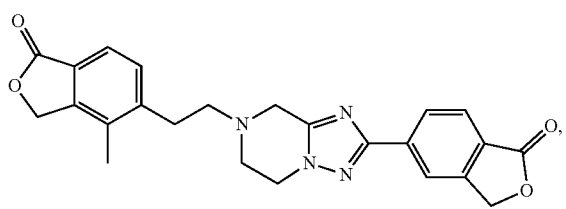
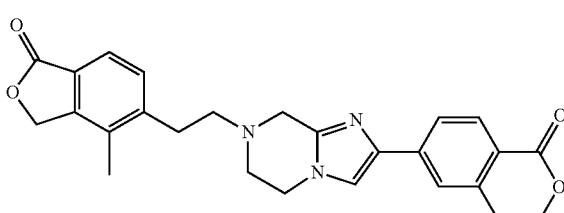
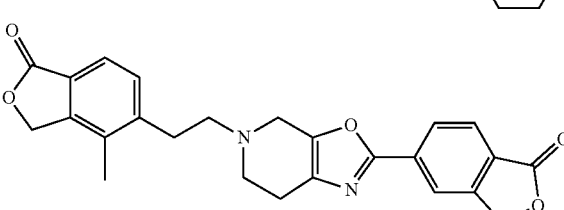
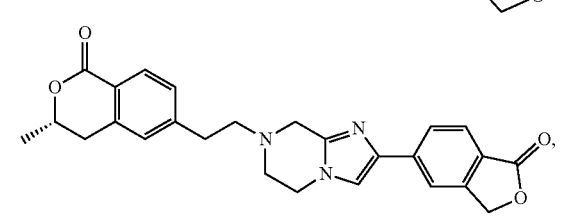
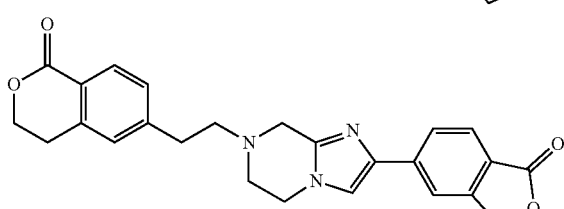
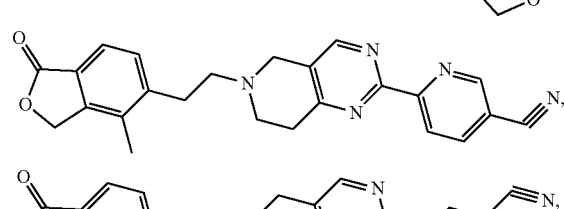
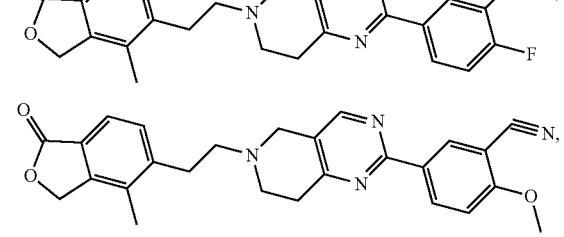
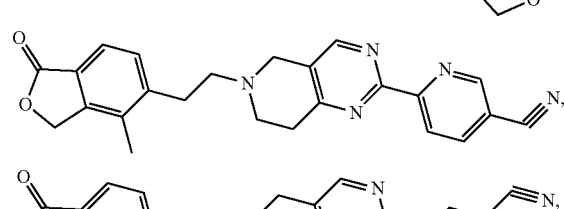
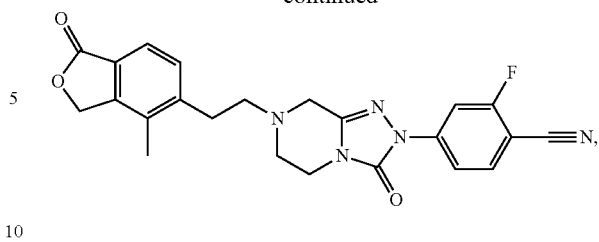
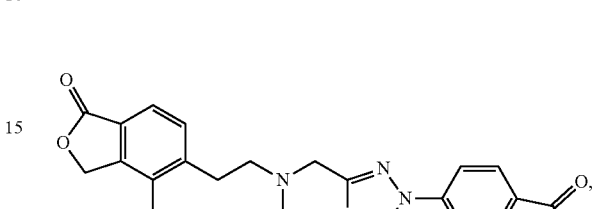
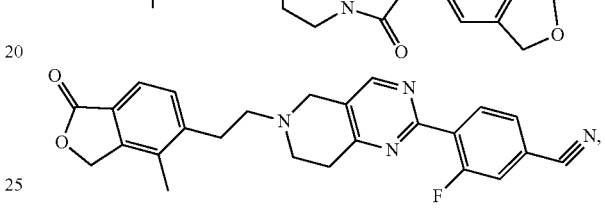
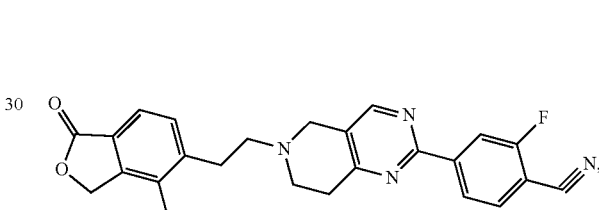
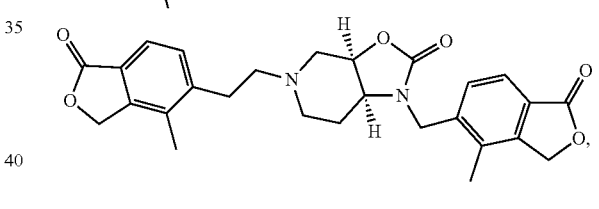
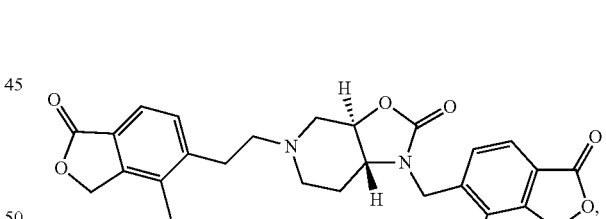
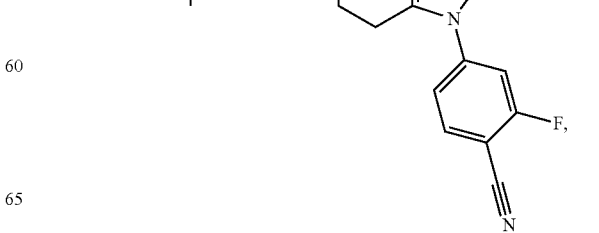

107
-continued
108
-continued
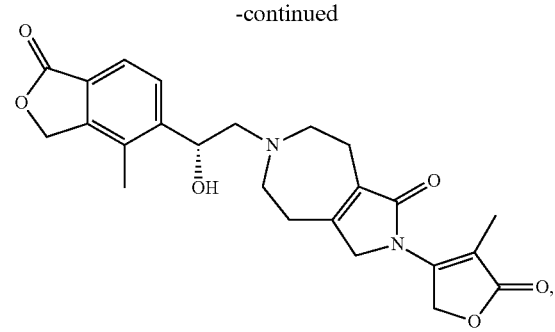
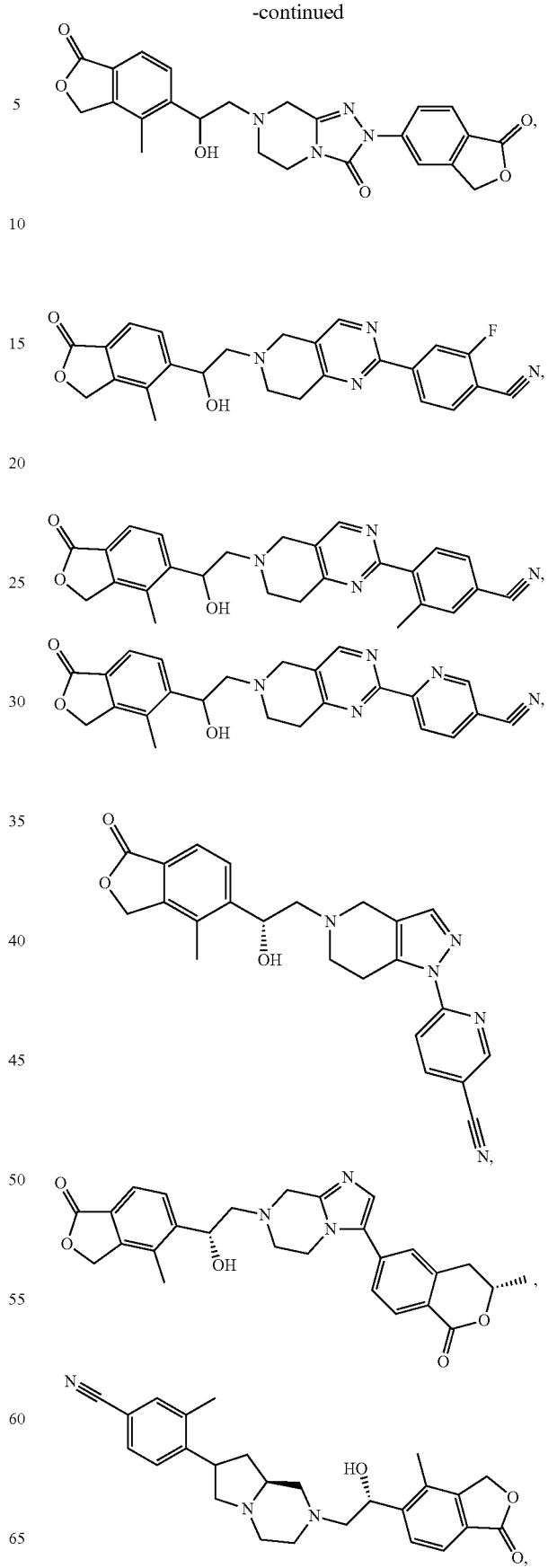

-continued

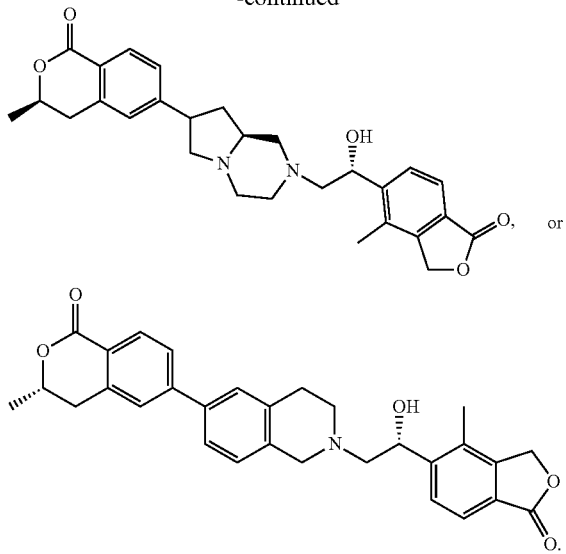

6. A pharmaceutical composition comprised of a compound of claim 1 or a pharmaceutically acceptable salt thereof and a pharmaceutically acceptable carrier.

7. The pharmaceutical composition of claim 6 further comprising an additional active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, epleranone or triamterene, or a pharmaceutically acceptable salt of any of the foregoing.

8. A method for causing diueresis, natriuresis or both, comprising administering a compound of claim 1 or a pharmaceutically acceptable salt thereof in a therapeutically effective amount to a patient in need thereof.

9. A method for the treatment of hypertension comprising administering a compound of claim 1 or a pharmaceutically acceptable salt thereof in a therapeutically effective amount to a patient in need thereof.

* * * * *